US011230738B2

(12) United States Patent
Rixe et al.

(10) Patent No.: US 11,230,738 B2
(45) Date of Patent: Jan. 25, 2022

(54) METHODS FOR DETECTION AND QUANTIFICATION OF EGFRVIII IN THE PERIPHERAL BLOOD OF GBM PATIENTS

(71) Applicant: University of Cincinnati, Cincinnati, OH (US)

(72) Inventors: Olivier Rixe, Cincinnati, OH (US); El Mustapha Bahassi, West Chester, OH (US)

(73) Assignee: UNIVERSITY OF CINCINNATI, Cincinnati, OH (US)

( * ) Notice: Subject to any disclaimer, the term of this patent is extended or adjusted under 35 U.S.C. 154(b) by 0 days.

(21) Appl. No.: 16/154,917

(22) Filed: Oct. 9, 2018

(65) Prior Publication Data

US 2019/0093177 A1 Mar. 28, 2019

Related U.S. Application Data

(62) Division of application No. 14/675,400, filed on Mar. 31, 2015, now Pat. No. 10,131,954.

(60) Provisional application No. 61/972,461, filed on Mar. 31, 2014.

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/156* (2013.01); *C12Q 2600/158* (2013.01)

(58) Field of Classification Search
CPC ............ C12Q 1/6886; C12Q 2600/118; C12Q 2600/156; C12Q 2600/158
See application file for complete search history.

(56) References Cited

U.S. PATENT DOCUMENTS

| | | | | |
|---|---|---|---|---|
| 6,225,093 | B1 | 5/2001 | Grant et al. | |
| 2009/0202999 | A1* | 8/2009 | Morley | C12Q 1/6858 435/6.11 |
| 2013/0210645 | A1 | 8/2013 | Volgelstein et al. | |

FOREIGN PATENT DOCUMENTS

| | | | |
|---|---|---|---|
| WO | 2008119562 | A1 | 10/2008 |

OTHER PUBLICATIONS

Frederick et al., "Analysis of genomic rearrangements associated with EGFRvIII expression suggests involvement of Alu repeat elements," Neuro-Oncology, July, pp. 159-163. (Year: 2000).*

Caye et al., "Breakpoint-specific multiplex polymerase chain reaction allows the detection of IKZF1 intragenic deletions and minimal residual disease monitoring in B-cell precursor acute lymphoblastic leukemia," Haematologica, vol. 98, No. 4, pp. 597-601. (Year: 2013).*

Mohammad A. Salkeni et al, Detection of EGFRvIII mutant DNA in the peripheral blood of brain tumor patients; J Neurooncol (2013) 115: 27-35.

Rebecca J. Leary et al, Development of Personalized Tumor Biomarkers Using Massively Parallel Sequencing; Sci Transl Med. Feb. 24, 2010; 2(20): pp. 1-15.

Jill L. Reiter et al, Comparative Genomic Sequence Analysis and Isolation of Human and Mouse Alternative EGFR Transcripts Encoding Truncated Receptor Isoforms; Genomics 71, 1-20 (2001).

Lori Frederick et al, Analysis of genomic rearrangements associated with EGFRvIII expression suggests involvement of Alu repeat elements; Neuro-Oncology Jul. 2000, pp. 159-163.

Lori Frederick et al, Diversity and Frequency of Epidermal Growth Factor Receptor Mutations in Human Glioblastomas, Cancer Research 60, 1383-1387, Mar. 1, 2000.

* cited by examiner

*Primary Examiner* — Young J Kim
(74) *Attorney, Agent, or Firm* — Dinsmore & Shohl LLP

(57) ABSTRACT

Methods and kits for detection and quantification of EGFRvIII in the peripheral blood for monitoring the therapy of GBM patients.

12 Claims, 10 Drawing Sheets

Specification includes a Sequence Listing.

WT SEQUENCE

EXON 1 EXON 2

(SEQ ID NO: 33) GGAGGAAAAGAAAG_TTTGCCAAGGCACG

EXON 7 EXON 8

(SEQ ID NO: 34) TGAAGAAGTGTCCCC_GTAATTATGTGGTG

EGFRvIII SEQUENCE

EXON 1 EXON 8

(SEQ ID NO: 35) GGAGGAAAAGAAAG_GTAATTATGTGGTG

WT

A A G A A A G G T A A T T A

80 x vIII

A.
Exon 1
Intron 1 (123 kb)
Intron 7 (1.7 kb)
Exon 8
Forward primer (set A)
Forward primer (set B)
Reverse primer
B.
WBC
Patient 1
C.
WBC
Patient 7
D.
EGFR-int1
SEC61G
(SEQ ID NO: 36)
EGFR-exon8
SEPT14
(SEQ ID NO: 37)

Patient 7

Patient 1

SEQUENCE LISTING

```
<160> NUMBER OF SEQ ID NOS: 35

<210> SEQ ID NO 1
<211> LENGTH: 24
<212> TYPE: DNA
<213> ORGANISM: Homo sapien
<220> FEATURE:
<221> NAME/KEY: misc_feature
<223> OTHER INFORMATION: EGFR exon 1 forward primer (9449-9472)

<400> SEQUENCE: 1

gtcgggctct ggaggaaaag aaag                                              24


<210> SEQ ID NO 2
<211> LENGTH: 24
<212> TYPE: DNA
<213> ORGANISM: Homo sapiens
<220> FEATURE:
<221> NAME/KEY: misc_feature
<223> OTHER INFORMATION: EGFR exon 8 reverse primer (145985-146008)

<400> SEQUENCE: 2

cttcctccat ctcatagctg tcgg                                              24


<210> SEQ ID NO 3
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 1) -
      (12373-12396)

<400> SEQUENCE: 3

gagtcgaatt cccaactgag ggag                                              24


<210> SEQ ID NO 4
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 2) -
      (22461 - 22484)
```

<400> SEQUENCE: 4
gtggaggcta aatgggcctt aagg 24

<210> SEQ ID NO 5
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 3) - (32458-32481)

<400> SEQUENCE: 5
ctgattgaac cttcccagag ctgg 24

<210> SEQ ID NO 6
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 4) - (39336-39359)

<400> SEQUENCE: 6
gtatctgccc agaaagctct accg 24

<210> SEQ ID NO 7
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 5) - (42376-42399)

<400> SEQUENCE: 7
ctgccttgca tgagacacac attc 24

<210> SEQ ID NO 8
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 6) - (52517-52540)

<400> SEQUENCE: 8
cccccatgta cccctttctt aacc 24

<210> SEQ ID NO 9
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 7) - (72411-72434)

<400> SEQUENCE: 9
ctacatgccc ctccctttcc tttc 24

<210> SEQ ID NO 10
<211> LENGTH: 24
<212> TYPE: DNA

<213> ORGANISM: Homo sapiens
<220> FEATURE:
<221> NAME/KEY: misc_feature
<223> OTHER INFORMATION: EGFR (Set A forward primers - 8) - (82388-82411)

<400> SEQUENCE: 10
gtatttgaga agcccaggag tgcc 24

<210> SEQ ID NO 11
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 9) - (92309-92332)

<400> SEQUENCE: 11
gacccctact ggaaagattc ccac 24

<210> SEQ ID NO 12
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 10) - (102263-102286)

<400> SEQUENCE: 12
ccagcttaga cagcagttct gcag 24

<210> SEQ ID NO 13
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 11) - (112426-112449)

<400> SEQUENCE: 13
gcctcacatc gttagtgttc cctc 24

<210> SEQ ID NO 14
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set A forward primers - 12) - (122310-122333)

<400> SEQUENCE: 14
catcttgggc taggggtgga tatg 24

<210> SEQ ID NO 15
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 1) - (18526-18549)

<400> SEQUENCE: 15
ccttaaggac aggcaaaggt gtcc 24

<210> SEQ ID NO 16
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 2) - (27420-27443)

<400> SEQUENCE: 16
ctgaccccta aggagcctgt aatc 24

<210> SEQ ID NO 17
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 3) - (38416-38439)

<400> SEQUENCE: 17
ccctgctcag aatgtaggcc ttac 24

<210> SEQ ID NO 18
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 4) - (58623-58646)

<400> SEQUENCE: 18
gaagattgct tgtgtctgcg tgtc 24

<210> SEQ ID NO 19
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 5) - (68243-68266)

<400> SEQUENCE: 19
gtgttcctgt cctggggtat ttgg 24

<210> SEQ ID NO 20
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 6) - (78406-78429)

<400> SEQUENCE: 20
cccatgaaag agtgcacagt ccag 24

<210> SEQ ID NO 21
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 7) -

(88182-88205)

<400> SEQUENCE: 21
cctctcatac agaccccaga gttg 24

<210> SEQ ID NO 22
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 8) - (98393-98416)

<400> SEQUENCE: 22
tgttcggaac tgtccatgtt cacg 24

<210> SEQ ID NO 23
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 9) - (108003-10826)

<400> SEQUENCE: 23
tgatgctggg aagactggac ttag 24

<210> SEQ ID NO 24
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 10) - (118642-118665)

<400> SEQUENCE: 24
tacgacgtgt gttctgtgac tcac 24

<210> SEQ ID NO 25
<211> LENGTH: 24
<212> TYPE: DNA
<213> ORGANISM: Homo sapiens
<220> FEATURE:
<221> NAME/KEY: misc_feature
<223> OTHER INFORMATION: EGFR (Set B forward primers - 11) - (128343-128366)

<400> SEQUENCE: 25
gaagtcctaa ctcatagggc ctgc 24

<210> SEQ ID NO 26
<211> LENGTH: 177998
<212> TYPE: DNA
<213> ORGANISM: Homo sapiens
<220> FEATURE:
<221> NAME/KEY: misc_feature
<223> OTHER INFORMATION: Homo sapiens PAC clone RP5-1091E12 from 7p11.2-p21, complete sequence, GenBank: AC009977 version AC006977.3

<400> SEQUENCE: 26
ttctttttag cacagaataa caatccattg tccacatgta ccatggttta tttatccact 60
catccacatg aagacatctt agttgattct aagttaggga agttatgaat aaagctgtta 120

```
taaatattca tgagcagatt tatgtggaca acagtgttca actcatttgg gtaagtatca    180
aggagagaaa tcattggatc atatggtaag agtatgtaca cttttatagg aaactgctaa    240
gctgcattcc taagtggctg taccattgtg ccttcccatc agcaatgaat gagacttcct    300
attgttccac atcctcatca gaatttggtg ttgtcactga tctgaatttt ttccattgta    360
acagatgtgt agtggtatct cactgttgtt ttaatttgca atttcctaat gacatatgat    420
gttgaacatc tttttatatg cttacttgcc atcagtgtat cctctgatga ggtgtttgtg    480
tagggctttg gcccattttt aaatcaggtt atttatcctc ttattattaa cttttaagag    540
tttagttctt tgcatatttt ggataacaat cctttatcac atatttcttt tgcaaatttt    600
tctccagtat atggcttgtc ttcttctcct ggcattgtcc ttctcagagc agaagttttt    660
aattttaata aactccagct tataaattat ttatttcatg gattgtgcct ttggttttgt    720
acttaaaaag tcattgtcat acctaaggtc atctaggttt tctcctacgt tatctcctag    780
gtgttttata gttttgcatt ttacatttat atgtatgatc agttttgagt taatttttat    840
gaagtgtgta aggtttgtat ctacattcat tttttgcatg tggatgtcca tttgttccag    900
caatatttgt tgaaaagact atacttgctc tattgtattg tgtttctttt ttgtcaaaga    960
tcaattgact aaatttatgt gcgtcagttt ctgatctctc tggtccattg atatatttgt   1020
ctattctttc accaatacca catagtctag actactgtag ttgtatatgt cttgaagtca   1080
ggtagtgttg atcctccaat tttgttctcc aatattgagt tggctattgt gggtcttttg   1140
cttgcccata gaatcaatta gtcaatattt acaaaataac ttgctcgaac tttgactggg   1200
attaatctat aaatcaagtt gggaataagt gacattttga cattatggag tctttctgac   1260
catgaacaca aactattgat ccatttattt agttatttga tatctttcac cagagttttt   1320
ttgttttttt cttatagatc ttatacatat tttcttatat tcatacctca gtattccatt   1380
tcagggtgtt aatgtaaatg gtaatgtgtt tttaatttca aattccctta gttctttgct   1440
ggtatatagg aaagtgattg gcttttgtat gttaacgttg tatcctgctc acttgctata   1500
actgcttatt agttccagga gctttttat tgtttctttt ggattttcta agagacaatt   1560
acattatcag tgaacaaaca cgatttattt cttccctccc aatcagtatt cattttattt   1620
atttattgtg tgttattgca ttagctagga cttctaatac aatgttgaaa agcattggtg   1680
aaaggaaaca tccttgcttt gttcctgatt ttagctatag gtttttgtag ctgttcttta   1740
ttaagttgag gatatccttc tctattctta gtttgctgag aatttttatc atgaataggt   1800
gtaggatttt gcctaatgtt ttcttctgta tctattgata tgatcatgta atttttcttt   1860
atctattgat atgatctgtt gatgtgatga actacattaa ttgagttttc aaatgttgaa   1920
ccagtcttgc atatctggaa taaatcggag ttggtcatca tgtataactt tgttacactt   1980
tgttgcattt gattttgtaa tattttcttg agaattttta catctatgtt cataaaagat   2040
atcggtctac agttttcttt cctttcttgt aatatctctg tctggttttg ctattaaggt   2100
aattctggct tcacaaaatt aattatggag tcttccctct acttctagtt tctggaagag   2160
attgtagaga atggatgtaa tttctttctt aaatgtttga cgaaaatcag cactgatctc   2220
atctgggctt ggtgctttct gttttggaag gttattaatt atttattcaa tttctatagt   2280
ggatataggc ctatattgat tggcaatttc ttcttgtatg acttttggta cattctattt   2340
caaggaattg gttcatttca tgtaggttgt taaattcgtg ggtatagctg ttcataatat   2400
tcatttatta tcctttcaat gttcatgaga tcagtagtga tgttccttct ttcatttctg   2460
atattcataa tttgtgtatt ctctctttgt ttcttagcct ggtgagaggc ttataaattt   2520
```

```
tattgatttt ttgaagaatc actttttggt tttgctgatt ttcttgctgg gattataggc   2580
gtgagccacc acactcttgc tcattttttc tatttttgtt ttccacactt tttctgcctc   2640
tgtggatttt acacagcatt ttgtataatt cgatttcctc tttttagcat agcaattatt   2700
ttagtcttta actttttaaa atcagttgcc ctagattttt ttctcccaac attttgggag   2760
gccaagggga gaggatcact tcaagccagg agtttgagac cagcctgagc aacatagcaa   2820
ggcactatct atacaaacat aattttaaaa agtccaggca ttagctagga ctgtgcctgt   2880
agtcccagct actcaggagg ctgagatgag aagatcaccg gagcctagaa atttgaggct   2940
gcagtgggct gtgatcatgt cacttcactc ctgcctagaa gacagttaga ccctgcctct   3000
aaaataaaca agcaaataaa taaaaagaaa ggaagaaaag aagagcaagg gcagcaaata   3060
gaaaatagta ataaatatgg tagctattaa tccaactatg tcaataatta ccttaaatgt   3120
tagtggtcta aatatactgc aatggactga atgtttatgt ctcctcaaaa tgtatatgat   3180
gaaatgtaag ctcccaaaat gatgttatca ggggagagtg tttttgggag ggattatgt    3240
catgagggtg gaggccttac aaatggggtt agtgctataa aagagaccac agagagctgc   3300
cttggtcctt ctgccatgtg agggcactgt gaaattatgg ccatctatga agaagtgggc   3360
ccttattaga catcaaatct gcaaatacct tgatcttgaa tttcccagcc tccagaacta   3420
tgggaaataa atttctgttg tttacaagta aatcatttta tgttattttg ttacagaagc   3480
ccaaaaagat gaagacatac accagatcac tccattctct tcttgcttgc atggtttctg   3540
aggatacgtt ggatgtaatt ctaatattct ctataggtat tttctttatg gctcctctac   3600
aggtaaggtg tttttccct ttggcttcat ttaagaattt ttcgttaacc tttgattttc   3660
tgaagtgtga atatgttatg cctaggtatc atttgtttgt ttgggttttc ttggcatata   3720
tcttcctgat gttctctgaa cttccagaat ctgtgatttg ttgtctgaca ttaatttgga   3780
ggaattttg gtattattgc tttaaatatt gcttctgctc ctttttctct ttctttgact    3840
tacagtattc ccattacatg taattatctc acagttcttg aaagttttgt tttgttcttt   3900
ttgttagtcg tttttcttc tgtttttcag ttttggcagt ttctgtttac gtatcttcaa    3960
tctcagaaat tctttcctca agcatgttca gcccactaat gtgtacttca aaagtattct   4020
acatttcttt tacagtgttt ttgatctcta gaatttttaa attctttctt aaaactttca   4080
tctctcagga attcaagact agcctgggca acatagtgaa actctatctc tacaaaacat   4140
tagccaggta tggtgatgca tgcctgtagt cagagctact caggaggcta aggtgggagg   4200
atcacctgag cctgggaagt tgaggttgca gtgagccaag gtcacgccac tgcactctgg   4260
attgggcaac agagccagac cctgtctcaa aaaaaagaaa aattccatgg ctctgcttac   4320
attatccatc tgatcttaca tgttgcctat tttttccatt aaaactccta gcctattaat   4380
catagttttt ttataattaa tactccgatg tgataatgtc ttagtccaat tactgtggtt   4440
ataacagaat gccacaaact gggtgattta taaacaaaag aagctgattt aggctgattt   4500
agaggctggg gagtccaaga gcttggtgct agcatctgat gagtgtcttc ttgcttcatc   4560
ataacatggg agagggcatc acgtgtgaag agagcttact cttataacat agccactccc   4620
acaagaatta acccaccgcc atgagagcca tgtgaattca ttcatgagga cagcgggtta   4680
agtttccaat atatggactt ttcggggaca cattcaaacc acagcagtta gttgtaacgt   4740
tcgtgtcatg tctcattctg gttctgatgc ttgtgcagtc tcttcaaact gcgtctttgc   4800
cttttagtgt gccttgcaat gtggaaatga tatactgggt aagaggagct gtagtaaaga   4860
```

-continued

```
ggcttctagt gacgtagtga caagctgtgg ggagagggag tgttgcacag tcctgccgca   4920
tgtcacagtc ttccagtgag cctgtgtccc tggactgtga acttcatgct tgcttctcag   4980
cttccccagc cccttagatg gtacagaact gttggagggg ggtggagttg tatatttccc   5040
ttgctctggg taggtcaccc tctgataaaa caccaggtta ggcctctggt gaaataattt   5100
ctcctgaggg cagaccttct attaataata gaatgttcca acctatttca aaatggttcc   5160
tcttctcctt ccactgccag aagcataatg agattttccc cctaatattc gtggtaagga   5220
cctagcagag ctccaggagg taacactctc aagtgtctca tactaccctg caccatgact   5280
gggctctgct ggagttctta atttgcagaa ctgcccacac tgagcctccc gcaatttctc   5340
aattacaggg caaactttcc cagccggcac tgggtccttg gaggtttctg tctgctggtt   5400
tcttcctctg gaggttgtgc ttctgtgttt gcctgtctct ccaatttggg gggcagtggt   5460
ttgcccaatg acctcaattc tctgaaagag ctaagaagag gtgttaattt ttcggtttgc   5520
tcagctttct acttgttgct agaatggagc gccaatagtg cctcctatag tgacatgtaa   5580
ccctcaactc tagagatgat gaagcatact aatgacaaag gagaaatgct tcagcagttt   5640
tctgtcagca cattacccct tgaaaaagct gcttcttcca cattctgcaa gagatgggtc   5700
tcaactcaga gctcaaggca aatgacttcc ttcaaggaga aggaataaac agtctcagaa   5760
accatgaaag cctgccccca ggagtgtccc tgaacctcag caggggccac acttaccttg   5820
cagaaatagg tgaggcatgc tcctggtaca aaatcccaat ggtacagaag gacaaattga   5880
aaaacaagtc tccctctaaa cccctgaccc cgagctacct agttctcctc cctagaggca   5940
aagctgttac cagattcttg tatctcctta acatatatcc ttagaagagc tgtcaagtga   6000
acacatgttt aagtgaaaac ctattttaga agtgcatttt cttaaggaac tttagggttg   6060
gaaggaacct gtgtcagtcc ttaattcaca acctccatta gtacttattg ttcttgcaca   6120
aaaatctttc tcaaaaaagc cctttccact ctgacatagc ttattctact tttacttagc   6180
tccaataact tataaaacat atttttgaaa gtctaaaatc tgccactatg tttttttttc   6240
ctaatcaatc tttactttga cctctaagcc agagaaaaca ggtggtcaaa tgccttttgc   6300
ctaagatgga acttagaata tttgaagacc tcagatcttc accctgccaa ataacgtgtt   6360
tctcctcccc tttcacagag catttggttt taggaaattc agagccacat tccttataga   6420
caagactaaa ctcttattca acatactcag aaacttcttc taagaggata accactcatc   6480
agaggaaaaa agtttctcat gtacagctgg caaagggatg gaaccatctg tgttattaaa   6540
attgacagac gcttatgaga tttattaagg gaaatactag agtcttagta catacttgct   6600
aatatagcat acatgaaggc tttatctata atttttttgg ccaagcagaa attttggtat   6660
tactcaccct aacaaatttc caagacatta tgaaatagaa ttttaggtcc tgacatcacc   6720
atttgtctca ggttttgaag cgttgctgga caagaggggt aaaacacggc tctgccttgg   6780
attcaaagtt ggcctctcat actagcaagt ataccttggt atcctggtca cttctcccgg   6840
ccacagcatc acattgctat aaaaggcaga tacaagtatt aaccagctca caggttatca   6900
gataagctta gtctgaccaa tgcttaacac agcaactggg ccactattgt cattcctgtg   6960
gtggtggcac acacacccag cctctgtccg ggccatggtc taggaccacc ctccacagag   7020
gctgtgagct agagccctaa ctgtgcaggg ccctaactat gccaggctac ttatctctct   7080
taagaggact tcattagtgc ctgctcggcc atacagtttt ttacttacca agtaacacag   7140
ttatcagcac actccaggta ctagccaagg actacaaaat caacgtgaat gtcagctttt   7200
gtatcaaaag ctcaaaggag aaactcaaac tttacataga tgtcccatga agatgttcag   7260
```

-continued

```
caaacccatt cttctctgtt ccctggaatc catcccagta ttgtgctatg tgtgtgtcta   7320
gtaattcttt acaaaaagct ctgtttcttg tgatgctatc agatcacatt gaagaatata   7380
caagccgtac tatgaaggct gttgtctcat atagtcctaa cgtagtgaga actgatgttc   7440
ttacatgctg tctttttggg cactcaaaga aattcctgta cagtcttaca aatcagttgt   7500
agcttaaatt gatttgtgtt gtgacttgta cacacaggtc acattccctt gacagaaaat   7560
atagtttaaa accaaatttg cagcccttgt taagtgaatg cacaggactt tattgtattc   7620
aggtctttta ttgtaagact cactcctgtc ttcattttat gttccactgt tgtgcttccc   7680
atttgccttt ctctagtttt gttttctgtg tttctacgga ctgctctcag cccaggtgtg   7740
caggaagcac acacatgcct gcagagcctt catggcctct gcattcaggg catgacttca   7800
acgcacagtg gctgtactga tttgttaaaa caaaggaaca gattacttct cctaattcac   7860
agggaagttc caggttgtgc gggcagtgag cagacctgtg tctgtctgcg cttgccctgg   7920
tgaaaaaccc caccgttcag gctgcagggt gcgagaccca ggcacaaaca ttttgctgga   7980
tgaggaggaa agatgtaagg ttgctcccct tcagagacag caaagggcag gtctgtagct   8040
tcacttactt caggattgtg atttttgaca gagccgagag atcagggttg ttgaaccagg   8100
cctgaaggtc ctagtgaatc tcgtgaagag aggaggggtc tggctgtaac atggacctag   8160
aggacatttt tactgcagga gaaggaacag tggggatggg gtggacttgc caaaggaata   8220
tagctcaagt tcctgcagcc caaaaaagct cagtttcttt tggccaaagc ttccgcgagt   8280
ttccctggca tttctcctgc gggagctaca ggggcagtgg gacacttagc ctctctaaaa   8340
gcacctccac ggctgtttgt gtcaagcctt tattccaaga gcttcacttt tgcgaagtaa   8400
tgtgcttcac acattggctt caaagtaccc atggctggtt gcaataaaca ttaaggaggc   8460
ctgtctctgc acccggagtt gggtgccctc atttcagatg atttcgaggg tgcttgacaa   8520
gatctgaagg accctcggac tttagagcac cacctcggac gcctggcacc cctgccgcgc   8580
gggcacggcg acctcctcag ctgccaggcc agcctctgat ccccgagagg gtcccgtagt   8640
gctgcagggg aggtggggac ccgaataaag gagcagtttc cccgtcggtg ccattatccg   8700
acgctggctc taaggctcgg ccagtctgtc taaagctggt acaagtttgc tttgtaaaac   8760
aaaagaaggg aaagggggaa ggggaccctg gcacagattt ggctcgacct ggacataggc   8820
tgggcctgca agtccgcggg gaccgggtcc agaggggcag tgctgggaac gcccctctcg   8880
gaaattaact cctcagggca cccgctcccc tcccatgcgc cgccccactc ccgccggaga   8940
ctaggtcccg cgggggccac cgctgtccac cgcctccggc ggccgctggc cttgggtccc   9000
cgctgctggt tctcctccct cctcctcgca ttctcctcct cctctgctcc tcccgatccc   9060
tcctccgccg cctggtccct cctcctcccg ccctgcctcc ccgcgcctcg gcccgcgcga   9120
gctagacgtc cgggcagccc ccggcgcagc gcggccgcag cagcctccgc cccccgcacg   9180
gtgtgagcgc ccgacgcggc cgaggcggcc ggagtcccga gctagccccg gcggccgccg   9240
ccgcccagac cggacgacag gccacctcgt cggcgtccgc ccgagtcccc gcctcgccgc   9300
caacgccaca accaccgcgc acggcccccct gactccgtcc agtattgatc gggagagccg   9360
gagcgagctc ttcggggagc agcgatgcga ccctccggga cggccggggc agcgctcctg   9420
gcgctgctgg ctgcgctctg cccggcgagt cgggctctgg aggaaaagaa aggtaagggc   9480
gtgtctcgcc ggctcccgcg ccgcccccgg atcgcgcccc ggaccccgca gcccgcccaa   9540
ccgcgcaccg gcgcaccggc tcggcgcccg cgcccccgcc cgtcctttcc tgtttccttg   9600
```

-continued

```
agatcagctg cgccgccgac cgggaccgcg ggaggaacgg gacgtttcgt tcttcggccg   9660
ggagagtctg gggcgggcgg aggaggagac gcgtgggaca ccgggctgca ggccaggcgg   9720
ggaacggccg ccgggacctc cggcgccccg aaccgctccc aactttcttc cctcactttc   9780
cccgcccagc tgcgcaggat cggcgtcagt gggcgaaagc cgggtgctgg tgggcgcctg   9840
gggccggggt cccgcacgtg cgccccgcgc tgtcttccca gggcgcgacg gggtcctggc   9900
gcgcacccga ggggcgggcg ctgcccaccc gccgagactg cactgtttag ggaagctgag   9960
gaaggaaccc aaaaatacag cctcccctcg gaccccgcgg gacaggcggc tttctgagag  10020
gacctccccg cctccgccct ccgcgcaggt ctcaaactga agccggcgcc cgccagcctg  10080
gccccggccc ctctccaggt ccccgcgatc ctcgttcccc agtgtggagt cgcagcctcg  10140
acctgggagc tgggagaact cgtctaccac cacctgcggc tcccggggag gggtggtgct  10200
ggcggcggtt agtttcctcg ttggcaaaag gcaggtgggg tccgacccgc cccttgggcg  10260
cagaccccgg ccgctcgcct cgcccggtgc gccctcgtct tgcctatcca agagtgcccc  10320
ccacctcccg gggaccccag ctccctcctg ggcgcccgcg ccgaaagccc caggctctcc  10380
ttcgatggcc gcctcgcgga gacgtccggg tctgctccac ctgcagccct tcggtcgcgc  10440
ctgggcttcg cggtggagcg ggacgcggct gtccggccac tgcagggggg gatcgcggga  10500
ctcttgagcg gaagccccgg aagcagagct catcctggcc aacaccatgg tgtttcaaaa  10560
tggggctcac agcaaacttc tcctcaaaac ccggagactt tctttcttgg atgtctcttt  10620
ttgctgtttg aagaatttga gccaaccaaa atattaaacc tgtcttacac acacacacac  10680
acacacacac acacacacac cggattgctg tccctggttc aagtgtgcca agtgtgcaga  10740
cagaacatga gcgagtctgg cttcgtgact accgaccata aacccacttg acaggggaaa  10800
catgccttgg aaggtttaat tgcacaattc caaccttgag ctgcgcgggt tccaagagcc  10860
aggcccgtac ttgctgttga tgtcattggc ttggggagtt ggggtttggt gcccagcgcg  10920
gtcgttgggg gaggggcaag gcatagaaca gtggttccca gaccttgctg cacattggaa  10980
ttacctggga ttaaaaaaaa aaaaatcaaa acaaaaacca gtgtctggct cccgccccca  11040
gacattctga tttaattggc atggggcaag acctggactt gggatttttt ttaatgctct  11100
tcatgtgatc tgttgggcag ccagatttgg ggatcactag acggaagaag gattgttaaa  11160
gtctccggag atgttacttg ccaatgctaa gagctctttg aggacatctg gaattgttac  11220
aatattgcca aatataggaa agagggaaaa ggtagagtgt gattccaata ataaaggatt  11280
ccgcttttca ttgaaggaac tggtggaaag gtttcttctc tgctgagcct gcaggcccgt  11340
cctgcctgcc tggggtgccc gggagacgcg ggcctgctcc ggagactgct gactgccggt  11400
cctgttagtc aggtgtcagc cctgtctctg ccgaagagac tcttctcttt attttaaatt  11460
aaaccctcag agcaccacca aagcatcact tttctccctc cattggtgtt ctcattcttt  11520
gatgttactt gtttgaacac cactattagt agttggagat ttgttcctga gaaaaatata  11580
aataccactt aatttgcctg tttgtcccgc attcactcaa aacagaatgc tcctgaagac  11640
aagagagaga gtaggagaac agacgctatt ccattacagt aacataaaag actggatttt  11700
caggggcaaa ttattaaaat aggagatgag ctcttttaac agaaatttgt ttaaggcctg  11760
tgtctatcaa attcagtgga ttttattcaa gatgcacttt gtttagtggg agttttgttt  11820
ggttctggga catgctaact tctagacttg ctgctcttag aggtaatgac tgccagacac  11880
catttcatga gtcctaatcc ccacattaag cataagaggt gcacactctc ctcctatggg  11940
ggaaactgag gtacgaagaa ctaaagtgac tttcccacag ctggtgggag gcagacggga  12000
```

```
aattcacacc aggggcttcc aactccagat ccctctctca acttccaaac tccactgcct  12060
tgtccgagtt ctggtttcag gagatccaaa tcaggtgtgt gcaaatgtct aatgtcagag  12120
ctggcaaggg gaaagggccc agggagccgg ctcatgacga tgagcctgtc tgaagcttca  12180
acgcgggctg tccggcagtc tgcattcctg ccgagttcct cagccctctg ttgggtcacc  12240
ttccatagag gcagcttagt cctcagttca gtgagcatgg agtggagact gcttgagggg  12300
tgctgagcaa agccctgcct cttacaggat gaaggtgctc tccagaaggg acactggaaa  12360
gtattccaag gcgagtcgaa ttcccaactg agggagcttt gtggaaataa gcccgcccag  12420
ccccacttct ggagacgttc ccattcagta ggtccgagct gtcttaaaga gaaaccaaag  12480
tggggatatt aatggtatcc aaagtgagat ctaccccacc ctccctcctc aaaggaggtc  12540
agatcaagaa agcccaagcc cggcctggca attgggacct ttcttctcac tccagcccag  12600
ggtgaaggtg gacaagtcac tttgaccctt caggcttctg agctgttgtt tctgaattca  12660
gtgaatattt actgagtgca tagaatatgc tagatattct gggctaaagg ttgaaggggg  12720
ggtgagtttt aagggtttct gctcttgctt ccagattgct ttcaaatctg gaaaggacac  12780
cagtggtttg tgtgttagac ccacactgcc gtagcacaga atacaagaaa ctggctgaga  12840
gctccaatag gcttttaaca gtaatttctg gcttcacgta tttagtttca taactcatga  12900
tttttcaaaa acttctggtt tgaagacacc gattgccgaa agtccattgt gctgcataat  12960
tacacttggt ccacgtgaca gcactaacat gttctgaaat gtttttagaa gtagtctcag  13020
caaagatgaa ggattcctcc ctgtttgaaa agaaaatatt ctttgttttt tctttgatct  13080
aagctctaag actagcagct agcatctgaa actttttttga cgagagtgac aaaccaactc  13140
taatattaaa ggcaattgat gattatgggc actgaaggga aggtaacccc aggctggtgc  13200
cccggaatag ggatgggtca caatgttgag gacatttcgc ctgttgcaga acccacctgc  13260
aacacagtgt ggcccttgcc atgtgacttg tgtgtgtgcc tgtgtgtctg tgtgtgcgtg  13320
ttttaatttt gacttcataa gtactctagt tatgagctta tttaacattg ggttttacta  13380
ataggggtat gtgttgagaa aatttcaaag ttttagaata tggttcaccc acatgttgct  13440
tccctgtaaa tataattttt aaaaccagat tctgggccgg gcatggtggc tcacctctat  13500
aatcccaaaa cgttgggagg ccgaggcagg cgaatcatga agccaggagt ttgagaccag  13560
gctgaccaac acggtgaaac ccagtctcta ctaaaaatac aaaaaaaatt agctgggcgt  13620
ggtggcaggt gcctgtaatc ccagctactc aggaggctga ggcaggagaa ttgcttgaac  13680
ccaggaggca gaggttgcag tgagccaaga tcgcaccatt gcactccagc ccgcgcgaca  13740
gtgtgagact ccatctcaaa aaaaaaaaaa aaaaaacaga ttctgttcct cagatccatt  13800
ccatttttgt tttcctttat cacttatgga catttgaaat tatggtaata aacattgtta  13860
gtctcagtta attattactg gtttattctt gaaccactaa tccatagaga atagagtgta  13920
aatcttaact tgttcctgta ggccatcccc attaaacatc atagtgtttt ctcattcgtt  13980
ctttttcgtt ttcctcctac aggaatgaat tttctaagaa aattccagca gttggctctt  14040
tggacgacat ctctagattg tcctccattg ggcccatagg cacaagctgg ccagtttgaa  14100
tttgggcaag aatccaggca ttggaactta ttcaaataac tagtttgcct gtaattttca  14160
ctttttcaga gtcatctgat aaagctttct tgctacacat ttagatagat acactcaatc  14220
cagttgtcta gaaagttccc tgagccagct gggagcagga ggggtagttg gggccaggaa  14280
tattgggggt gtgtttactg agcccctaga aagtaagtgc tagatttgac atttcaatcc  14340
```

```
ctgaaggccc tgaagttcag tatcaaatga ctggtcctgt ggactgagca tctgtgaatt  14400
gcatatgctt agagtaaatt ttactcctac cagtttcagc agcttgcttt agcaagcagt  14460
atggaaacac taacatgggg gagtagaatt tctctctctg atccaagttt tatctcattc  14520
tggtgggttt tcaaggagag actcggagtc caagtgtcct ttctgaatat atctggaact  14580
tctcattaac aaaagactca agttataatt taggggacaa ggcacccaat gagaatgcct  14640
tgcaggcagc cctaagtaca cctgcaatta caccattact agcgcggcag cacacatggc  14700
cctgacttag tttaaataat tacgtaagtc aaccatgatt gtttgccctt tgcatagaag  14760
ggcaagtatt ggtacctgtt acaacttagg cttttttttc tttatgtttg agccatgatg  14820
agtgatttac actgttgcat ccatatgttg agatgtaaga ataaattaga cttggtaatt  14880
gcccttaagt gtctggaagt caactgggga aagagagcta gagataataa gtgtgaaaca  14940
atgtcacaga atcaatgacg gaactcttcc caggacaaag gatgactttt gagttcagtc  15000
tttgccttta attctacatg gggaggagag cacgtttagc cacaaatgga agggattact  15060
catttgagct atttggttat atgattattt ccccagagaa taggatgtgc agggcattac  15120
acaagcagtg ccaatagcag caaagttctt gagagtgcta gtaattcaaa tggcaggaag  15180
agaaggaata aatggtaagg ctacctacag ttcacagaga gctccatcct cactgtggct  15240
ttggattttg tcctgtgtga aagagaagtg actgtgaact gacatgctgt gtttggtgtt  15300
ttagaaagat ggctgcagca gcggtttggg gaatggactg caggagtggc attggaaaca  15360
ggaaggttca tgactattgc cagagacaga ggatgaagca ggagcaagga agattcagga  15420
caggggactc cggggctgat caggaggcag aactggttga taagtatatg tagcagcata  15480
agaaagaaag aatcccagat tgacacccag gcttctcact tggaagcctg gatagatact  15540
gaatgcaatc acaaaggctg ggaagtcaat gggactgcag ggaagggaag ggaagggagg  15600
agaagaggaa gggcaggagg gtccaatatc aatattcagc ttttagatgt gttgagcttg  15660
aagtgctcag atggagaagt ccaggaggca gtagaatacg gtggtccaga gcacaggaga  15720
gcaatgtggc ttgagttgtc atttgctcac atatttccgt gtcagttact tgtcttagat  15780
cacagaacaa gttctcctct cacagtttcc tggctccacc tgtctcatgc tcaccgtcag  15840
catcgaaatt gagccacacc aggggttctg gataccagct tctctctagg tgaggctgct  15900
atagtcagca gctgattagt tgcagttatc agcaactggt aatataatat attgtgcata  15960
taagtgtacc agaagtcatg tttatatatt gctgcaaata ctcggaatgg ggatctcttg  16020
ttccctgctt aagaccacat cacattactt ggttttgtac gctagtggct gaaccaaaaa  16080
aagtaggaga tgattttttt tctttttttct taaagcagta gcttttgaac cttgaccatg  16140
ctttctaacc agctgagggg cttttgaaaa agagggtgcc ttactgtgcc ccagaccagg  16200
acaatcagta tttctgggga atggagcctg gcacacacac atttcttaaa gctcccttgg  16260
caattctgag gagtggatta catgttgtat gtagctcgta acgaaagaaa tcttgtcttt  16320
gctctcagac cccccatttct tactcatctc atgagctcct tcgagatcca gaaacagttg  16380
catatttcat tagtaaatca gttccagagt cacattttat ttcacaagtt agtccattaa  16440
aagtttcctg cagtgaggaa atagccagaa agaacactcc acccctcctc ctttttataa  16500
ctatagggtc tggctcgaca gagcaggagc atcgccatct tggacaagcc cctcattcta  16560
aagttcacct taataaaaaa ctgcctaaat tcaaactgca tcagcctaat ggctaaggtc  16620
agcatgacca taaaccacaa ataacatctc caaccggaaa cattcgaaac tcctcctcga  16680
ccagagacat gctagtcccg agataacccc cctccagcag ggaagatgcc agtctcggga  16740
```

```
taacctctct ctggccggaa agatgcctgc cccaagataa acttgcctcc tcccagagat  16800
attccaaccc tgccataaaa cttctccctc aaacaggaac attccaaaat tctgataatc  16860
tccctcaccc taaaaccaat atatactcct agtctgtaag agaaagcgct cttgaccaaa  16920
attcaccagg agtgcctccc aggttttaac taaagaaaac ctctctttaa ctgccaaaaa  16980
aaaaaaggga aaaaaaaaag ctttctgcag tggctttcag cgggcccagc atggcagcag  17040
cacctgagaa cctgttggag atgcacactc ttggacccca ccctggcctc tgagtaagac  17100
actggaaggg caggccccgg tctgtgcaca caagtcctca gggagattct gactgatgca  17160
tgccagattt tgagaactgc tgatatactc caggcacatc gcatgctggg atctagatac  17220
accaagggaa caaaataact gcacttgtcc tctgaggacc gacttacctt ttggaagggc  17280
tgagaaagag agacacatac aagatcactc cctgtaatgc aatgttttat aacagatgtg  17340
atttgggatt tcagtgggag cccaaaagag ggactgacta attcagcctc tgtgacaagg  17400
ggagtttctc agaaacagaa tgcttagctg ggcctccagg cacagggaca ggaatgagga  17460
aatacttgta ggccctgtgc tccttcagca aaaccctcag tttcttgtta tttttataaa  17520
tgcaaacatc ttattaaagt agatgctaag gcattagaat ttcctgcttt atttttctaa  17580
atgaccatga ggaaacctgg aatgtcaaag ataaagtgca acacattctg catttaaaaa  17640
ttaaaatgat ccttttttaaa agtagcaacc agatgtgaaa aattggactg gagtccaggt  17700
tatagttgat agctttaact ttctccccaa cagcaacagc acaattttcc ctaaaatgtg  17760
ttatgaataa gtaaaatgac tacttcacat cctttaactc ttcctacaga aatctaagag  17820
agaaatgaaa caaaagtttg cacagttcta gacacgataa atacatgtga aatcacacaa  17880
ctcagaaaat gtcccttaaa ttaattgagc cattggtact tgtgaattag aagagacatc  17940
tatgttctga tccactgttg aaagctgtac aatgttacct atttatttgc agacatcctt  18000
tggaaacaaa taggtagatt tgcaacaaat aaagagtgga gtacagctgc tgacattacc  18060
ttgtatattc atgcctttat gtaaaaaaaa aaaaaaaaat atatatatat atatatatat  18120
atatatatat atacacacac acacacatat ggaggtaaag accactgctt gctttgcagt  18180
tgttttaaga gcattcatga aggattttat tttataagca gaaatgtgat atctgacgat  18240
tttaccacta catgcttgca ggccagtgca cagcagatga cgtcatgatt gttttagcag  18300
tcctatcgtt ttacttatga tgtcattaca accctttgct aaaatttctt tcctttactc  18360
caggttttgg ataaaattga tgcattgcac atagtctctc tgataagaca aactggcatt  18420
tgtatgtgaa aaactgtgca tgttttagtg tctctgctga tactcaaatt atccattatt  18480
ttagtgctgg aataaaaaca aaccacttag tgaatttgtg caggtcctta aggacaggca  18540
aaggtgtcct gagattttct gatcattgta taccaaattt tagaaacttt ttcaaaaaca  18600
ttttttaat ttcaaaaacc tggttttgtt tatttaccag caatcattga atacctgaaa  18660
gctttcagga gattttatta caatggtttc tattcactta caaaattatc tcctagttca  18720
ttctcataca ctgtaagcca ttgtaaatgc ttcaaattgt gccgaacaag ataaactaga  18780
caaactattt taagtttgtt ctagtgctaa cttgcaagat ctaatggctc caactagatt  18840
tttaaaataa agtatatttt aatatattat tagaaagtta agcaattatc tgtttatagg  18900
taacaaaaac cctggaaccc caatgtcaga tgtcatccac ttttgattaa gtccaaacat  18960
atgacagata aacaaaagat ggttggctgg gctcagtggc tcatgcctgt aatctcagca  19020
ctttcagagg ccgaggcggg cggatcacaa ggtcaggagt ttgagacttg cctgaccaac  19080
```

-continued

```
atggtgaaac ccgcctctac taaaaataca aaaaaaacag ctgggtgcgg tggcacgtgc  19140
ctgtagtccc agctactcag gaggctgagg caggagaatc acttaaacct ggaaggcagg  19200
ggttgcagtg agctgagatc acaccactac actccagcct aggcgacaga gcaagactca  19260
gtcaaaaaac aaaaaaaaag tggtcattgg agaattattg tgtcacctgt tgtttttttaa  19320
tgtactaatt ttgagaggct tttaaataga gtgcactata gaactttttc ttggcttcaa  19380
tttgctacaa tgttaataga gaatcagaaa ccttatcctt atagatgttt cttgattttt  19440
ttaatttctg gtgacattta tgagtgagaa tagtgtattg ccctgttttc tttcttactc  19500
ccctttcttc ttccttcctt gctttctttc ttcttccctt ccttctttct cttcctcgct  19560
ccttcttttt tacaagctgt tatgaattag ccttcacaga gaaagaaaaa tttttataaa  19620
taactggaaa tgaaactttg caaaggactg cagatgaaaa actttgtcaa atgactgtaa  19680
aaatatacta tataattttc aaaagttaga aagtaccaaa cacactcagt attcatggtt  19740
atacaagtat gcatacacat gtattgctcc ctgaaaagtg gtgttgttaa gggagttttt  19800
cttagtacgc ggcttaacat atttttttct gtaatttgtt gttagttata atggggagag  19860
aaaacaggtt agagtctccc ctctcagttt caccttccat aaaacagcta aactagacga  19920
tcgtcagact ccttccagct gaaaacatct gtaaaattaa aaacaaatct aaatgtatgc  19980
aagatatgta tttaaacatg ctggtaataa gtgtgctgtc cctataattt agatgctaaa  20040
acattgatgt cataataata acaacacctc gcatttgtac agcacctcat agtttacaca  20100
atgccttaac attcttctct ctcagcctcc tacaacccca caggattggg atagctttcc  20160
agattgggag gtgagggacc caggctcaga gcgattctgc tgttgtccgt aatcaccagg  20220
ctggtgatca gtgggcactg ggtgctctcc tgctacacag cactgtctct caacatgcag  20280
gtcaaggtta cttattcctc cttcaagacg tcattgggtt ttttagctat ggatgcccca  20340
tcacttttag ttctatttgt gaatcaaagg ctaaataaag tattcctcaa aatttgttat  20400
acttctgtta ctaatgctta atgtccctca caatttctgt atatttctgt gtatttctgc  20460
tctgttttgg ttcctttccc aggtttcttt tttgttatga agtagttttt agactcaagt  20520
ctcttctgta tgtgttataa ctgcccattc cataagatac agggcagtga atttgtgagc  20580
cttgaaaata tttactttag aaatgagaag tatgactttt caacgttgtg tcatcaactt  20640
ctgtaaattt tccagaccta taaatacttg cagaaaaaaa atgaaaggag aaggcaactt  20700
gatttagcag ttgggtcagt tagcaatgcc tatggcaagc tgtagtaatt cccttacata  20760
gatttgtaag actcatttct atgatttaaa tgaaggcata cacttaacct ctttagggtg  20820
tgaaacagct tttacaaaaa gagacaaact taagaaacag tgtggccctc caagagtgtt  20880
cattttccat atcataccat ttgtaataag ctattctggc tgggatttac ttgcaagcat  20940
tggcttttaa gaagagatgg tttcacacat caaattattc acttggaggc actttctggg  21000
ttgaaggaat ggaatggaga gtgcggcagt gagtagatct ctcagtgacg gtgatgtgcc  21060
tctcccagaa gaaatttcaa aatgcagtgt tcattttcct ccacaagaaa ggaagaaact  21120
gttttgttat tgtttattcc taacatagtg gaaacttttc agtactctgg cagaaatttc  21180
ccaaaagcaa ttttctattt catgattata aagtagcaaa ggaaaaagtc ctgcactcca  21240
gctgagcaat ggatctccag ttgttatcta ggtgctgcag gtttagagag gattgccagg  21300
agaacacatc gatttttcag gcctgtgatg acgtatctct tgttgaataa gtaaaccctt  21360
ccagtaaaca gacagttagt atattgattt cagggtggct ttagccactg aacctgtaag  21420
tcttgcaaag gttacttggg caaaagcatc attattttac cttcagtcaa caaaaatcta  21480
```

```
cctggccaag gcagaacaga aagttcagca atttgatgaa gtgggacaac atgaagaatc  21540
aggtgagttg cctacttttt cacttcactt tccaccttta gagattcttg tttagatgca  21600
gagtagtgac gtgcctggtg tcagggagag agttgaatga gaaaagtccc agaagggcag  21660
aagacttggg tgattatctg agtccatctt tccttatcac atgacagagt tcttgaagtc  21720
ttggctagga attctaggct tttagattct ttgggcaatg gctactaaat gttcataatg  21780
ttgctcagtt gcaaaaacaa gacattcaaa ctatagccag ggagataagt agtcacgaac  21840
tcaaggccta aattctgctg atggagccga tgagaattgg gtgctaaggc aaagagagtt  21900
gccaatatta tattcttcgg ggttttttgt ttttattcgc attttggaaa aggaaaatat  21960
tagcattcct ctgacttaat attgagaaga cattgggcac tctttttcct cccacacttg  22020
tcttctttca ctaggtgaca agggaagagg tagcatgagg tggtggtcac aggtgagagg  22080
ggctgttgtg agcacaggca tgttgactgc acattggtca cctagtagaa gttttgcagg  22140
cttggtgact tctgaacact gttttcaagg ttgattttta gttgagagaa cctctaggta  22200
ccacgtaatg ttattaacag tagtactgat ctcacaatcg ccctatgtcc cattcacaag  22260
atgttctgcc aagccataaa aggcccagtt aagtttaaga gaagtctcaa aagtaacaga  22320
tgataactaa ttaataccca gtgattttga aatgtagaca tcaaacatac caattcagtg  22380
gtatcatcct tagaggcaga cagaggatga ttaaatcatt cagcccatct ctgtctgagg  22440
acgcagctta gcacagcatg gtggaggcta aatgggcctt aagggaaaaa atgatatctg  22500
aagatgcaat ttatttcaaa aagagtttgc tcccgtgaat tttcactctc tatgtagaac  22560
ggcaccagca cacacttttc ctgagccttt gcatgtgtgg caggcagcgg cctggcatcc  22620
tggggaactg aatgaggacg cagatgaccc ggacgtgttc acagtttgac acatctgact  22680
cccagatcag ggacagctag ctttgctggc tggttaagtt gatgattcca tctttgcctg  22740
gttctctgac tgtctcatgc tttctgttat tactattttg cagcagatat ttctgctcat  22800
ttttcaatca tatatgcatc ctggatggca tagagttgat tctcctaaca aatcagtgtc  22860
cctttgtatt tttttctggc cataagatag aatatatatg tcatttatta aaaatggaga  22920
aaatgttcag gagtttcttg actcagagag ggaaaaggga tactcagggc actttttcag  22980
ccaggaattt actacctttg cagggtaaag gggactcacc acgctggaag tcaaaataag  23040
ccaccagtgc caagtgttca aagcccttag aatcacaatg ctcttaaagc aaagtcttca  23100
acaatgcttg aaaacttcca ctggttctca gtatgtccaa aattgtcatg tctatgaatg  23160
attttctcaa tctgaaaatt tttatagcag gctaaagaat gagataggtc agtgtgattc  23220
tagaactaat cattaacatt caatagatga ctattttatt ctagaaaaag cagcaacttt  23280
ctatttactc tctattttga gggtaaattc tctgtaagta gaaaaagcaa aatgtggaca  23340
tgggactaac atatgaatat acaaagcaaa tgtaccgaaa aaatcttaag acctgccttg  23400
tggtgttttt tgttttgttt tgttttcatt aaagtgactt gttagcctct tgctccctgt  23460
gaagcacagg gaggtgacgt gatgtgcaca gggcagactc tgccatatgc cctggccttg  23520
aactcagggc cccctgggga ctgcagggga tgctggccat gctgagcaat gcctgtgggt  23580
gtcagtttcc tcatctgcag aatgagggta ggcctggtgc ttatttcata gggtcgcaga  23640
ggggattcag tgacagggtg gtgtagaggc tggagcgtgc cccatgtgtg cacgacagcc  23700
ttccaactag gggaggcggg cctgggctct caccagagag cctgtgttct ccatggctac  23760
atgactttgc cccagacgtc cttcccgtgg tctggaccct gggaagtcgc caagagccag  23820
```

acaggagaaa ggctccactt ggctctcctc tttggtgacc atcccttgcc tccatggcgg 23880
gactctcagg tgacatccca ccaaccctca ctttgcttcc ctggtgggtc tcactttccc 23940
tcaagagtgt tgctttttttg tttcctgcat agtcctgggc cagttttgat aaccctcttc 24000
atttcacttc agaaaccctg atgatttctt cctgtgctct ttttacctta ggacttttac 24060
tatgacgact gtgactggcc catttcttgt ttttttctc ttgctctgct ttctccccca 24120
tcatcactaa agcagacatg gcaatgatgg ccatgcacac tttccaaggg tccagctgta 24180
gatcttcatg gttccccagg tgcctggacc atcttgtgag gagggaggca aacacaccct 24240
gcctggagca cttggccctt tcggcaatgt tttggcttcc tcaagtgaga aaagaatgga 24300
tttgtattcc ccctctgcat tattgttttt gttttgtttg tttgttttgt tttgtattga 24360
gacagagtct cactttttttc cccaggctgg agtgcagtgg cccgacctcg gctcactgca 24420
acctccacct tccgggttca agtgattctc ctgtctcagc cccctgagta gctgggacta 24480
caggtgcccg ccaccacacc tgactaattt ttgtatgttt tgtagagaca gggtttcacc 24540
atgttggcca ggtgcccatt attatttgat ctggaattaa ctgagctact gcaggaattg 24600
cttgattcac tgatgactgg tgttgagcca gtacacaccc acacccaagg actgtgactg 24660
tcttctgagg tccatcctca gaaattcctg tctcttcacc tagtgtgtaa taaggcctgc 24720
gcgtgttata tggaactgta aaaaatgcgc caaccatctg tccttcctct ttatctgatt 24780
acttatcatt gttctctaag ttgcaagtta atagactgat cataaattaa tgcatgctgg 24840
agacttgctg tttcctacta gcagcatata aaagttattt ttaaagttgt tttaaatctg 24900
tgagtaaaaa taaattgctt tgctgcaaga aacaccaaac atggaaaagc taacggttca 24960
aagttaataa tttatcttat ggacatcact agtggcatag ttgctttaaa cagtgagagg 25020
atttaataga tatttgattt gcaagtggga tgaagggtgg tctaaccttt gtcctgtgtt 25080
taccttccat gagatcctag aggttgtaca gcacagtagt ggcatgtgac acacttgaga 25140
gtgcctgttc tgtttggaaa cctggaaact atgaagggaa gtggccttcg agcttaacac 25200
ataagacttg ggaggcaaaa ccttttattc tctttaaata ttcactttag gataagcatt 25260
tttttaggtg ttaggaacag ggaaaactgt gtggttagga aggaagaaag aagaaagtta 25320
actgttgtac attccctagg taatgttttt aagcattgtt attcactttc aaaacacatt 25380
ttatttattt ggacttaata ttttgatctt attttttcaa tttcttttaa tttaacagac 25440
aggatgagtt tttttatagt tgtattactt agaaattata ctaaaaatgg ccgagtgtgg 25500
tggctcacac ctgtaatccc agcactttgg gaggccaagg caggtggatc acttggatca 25560
cttgaggttg ggagttcaag accagcctgg ccaacatagc aaaaccccgt cttcactaaa 25620
aaaaaaaaac aaaaaaaaaa ctagccacgc atggtggcag gtgtgcctgt aaccctatct 25680
actagggaga ctgagacata agaatcactt gaatccagga agcagaggtt gcagtgagca 25740
gagattgcac cactgcactt cagcctgggt gacagagcaa gactctgtct cggaaaaaaa 25800
aaaaaaaaag gataaagaaa tcatactaaa aacaaaacag aatgctgacc accttataga 25860
aatagaaata gtggtttgct gtgatagcaa attttcttgt taactttta tttttaaaga 25920
attgcacatt cacaggaagt tgcaaaaaat ctactgggag gtcctatccc ccttccccca 25980
acctcctcca gtagtaacat cttagtagca aagttttgta tatttatttt gatatcatta 26040
tctaagtttg acatcattat ctaatattaa cctaagccaa aagcccacta ttttaattat 26100
ctagtgatgc agtgttatag aactcatagc ctttcacagc attatttgga agttaatttt 26160
cttaagtgaa atgtttttgg tctttaaggt ttggaggcca tggaggcatg aggagaaatg 26220

```
ggatgaggga gagagagcta agatagataa agacagagat ggggagatcc actgattcgt  26280
tgaacaaacc agatacttcc ttatagtttt tggattaact tacatgagct aagtttatat  26340
tctgttcaga tcacaagtgg tcaagtttgt gtgtgtgtgg gggggggggg gtgggtgtgt  26400
gtgtgtacca ctctacccat cctatattta ttgtcctgta tttggtctgt tctgccttct  26460
ttattttcag gataggtgtc ctaaatgagg gtctttggaa agctggtgag gccatgttgc  26520
ccgtttcagg tgttccgtgc tcaaatgtat tcatttcttg aaaaattcag ggagtgcaca  26580
cttttgtaca ttttcctatg tgtatatgat accattatat aaatcttaaa aatatatatg  26640
gttcacctga atccccagcc atttggtaga gaagatagaa aacctacaga ggaggctaag  26700
attttattag aaaattcagc ttctcgacgg aggtattggc tttaaagtca aggcaatgca  26760
tctattcttt cttttgatat aactagctaa aagatctctt aaattcaaag tggccctcat  26820
cttactgtta ctgcaattta ctcttaatta caaattatat aaaaataggt tttgaaatac  26880
tgtagcgaca aagtaacata cctctgctcc attacacaga taaaacctct aaggaacacc  26940
tcctctctta acaggcatta accaactgca gaaactgcag aaggacaggg ctatttggga  27000
ataacacagc tcccttcctt gtctgttccc tcccattgtc aggcttctgt ggagccatat  27060
tcagagcaac atagggaggg ggaagagaaa atcaacccct tggtgaagga aagctcccaa  27120
ttcacagagc aaacatgggt actcttgttt gtgggagctc ccagggcctc ccagctcacc  27180
gagcattctg agccctgatc cttacactaa ttgtattatg caaccataaa tgatgtctgc  27240
tgtaccagcg gggacagttt attttaatag attggtataa cttggcagaa tcttatctgc  27300
atgtttcatc ttggattttt agctcaattc aactcaatag gcatgtgtca aatgtctact  27360
gcagactgag cactgaaaag ctgctgggta cagggttaca tggatagaaa acgtagcctc  27420
tgacccctaa ggagcctgta atccagatcc ccattctttc catcccattc tcccaagcaa  27480
gaatttacct aatgtggttt gcgagaattt aagagctgga aaggtggtca cgagaagccg  27540
gaatgggttc gctaaaatgt gtctatatga ttaagcataa cgtagctttg cagcactctt  27600
cacagcttcc tcagagcctt ccgcacgcgg tgtctcattt gaatacttgt gtgaggatag  27660
cctcataccc ctcagtgagc tcttcatgga gtgatgcagt agacagcaag cctcacactt  27720
ctatgctcac ggaagaccaa atttgccttg aaaaatcttt atagtctctt cacatttcta  27780
agttgacatc aaaaatcggt taccataaaa tcctaatagt tgaagagatg taatttcaat  27840
tatttggtaa acctgacctt cattgtcaaa gcaattagtc aactcagatt tactttctcc  27900
cagataatag attctgactt cttttttttct gattaaaaaa cttaacacct tcctcaggag  27960
atctatctca gttctgaatg ctgattctaa ctaagaagga tatttggcta catgctggga  28020
agaggggtac tgaggcacgc cgcgattcca ctccagcatt tccagttagt cgggtgcctc  28080
tgcactcccg gtgttccggc gcccagttag ttgtgtactc tgggctgtcc ctatactgga  28140
gtcctaaaac acttacgact gcagataggg ggaggttttt caaaaccttg gtctgaaaag  28200
ccatagaagg gagataggaa agcggggggg tggagccaca gtacattcag gtggatccgt  28260
ttttggaaat agtacaaact ggaggtgaaa ccctggaaat tgatctgtcg ttcacatgct  28320
tcatgccgag tccttgtgga cccacagaga cacactcgcc ccagtttgaa ggctgctaac  28380
ttgattctga ggacaccagt gaggtggtag tgtgcaaatg atgtgtgagg aaactttgga  28440
ggagtctcac cctgcctgga gcacgtggcc cctaaaacag cgcagcctcc caaagacaga  28500
agatgtggac tagtgagaag ccaggtatgg tgactgctgc tggatgaagc ttgtcccacc  28560
```

-continued

```
agaggctcgc ttgtttcatt gagcacctac tgtgtgcttg tgggatgcaa acacacgtgt  28620
ggtccctgcc ctcaggttaa taggcagggg tggaacagtt atgaaactgc tctaaagtca  28680
ttttctcaaa ctgggagtga caaatgtatc cacttggaaa agattgagaa ttttataaga  28740
tttttaaatt tttgtttatt cacattgagg agaatctaaa ttcttttgaa cttatgtata  28800
gatttcacca ttttatagta ataaatcagt cctcctgtgt gtgtgtgtgt atgtgtgtgt  28860
gtgtgtatgt aaacctcacc ttgcaatatt attattttaa atagccactt gcatcttaag  28920
gaaattaaga ggacaaaaga aaagctgctg ttttgtatgt atccacatat ttaccagctg  28980
cttccctgcc ggcaggtgct ctggttctgc actgcctgtt gtcccttgcc tgaaaatggt  29040
tgcctccaat attttgctca gttttctgat tgtttacagt ggcagaggag ggtagatctg  29100
gtaccagtta gtaattgcca gaggtggaag tctgtggatg aaatttgtat aacatggaac  29160
gttagttcca cagttaatgc tactcaattg gaacccatgg aaattatttt ttggtgaaaa  29220
gggcccatgc gttatgaaat ttgagatcca tcactttaag tgaatgtagg ccctggatac  29280
agtgggagct cagaagagca aatcagttgg tcaccttgct caacgtattt tactaagggc  29340
atcagtaagg ctttctatga cctgctcctt caatgcttgg ttgacatttg gggagcaaag  29400
ataaactaag gattctaagt tctgtcctgt gatgctgtaa ggggaatctc aaacctctag  29460
gtggaggagt gcagagatga ccaggatggt ggaagcctgc aggagagctg aacacctgaa  29520
gacacccagt gggaagacca ggacctttaa cgcccatatc tgctgctcaa gactggcaga  29580
gagaagaggg tttgtgatga gaaaaggtgg tgaaaggcac aaggaggcac agagcatgtc  29640
aggtcccata tcccaaaagg aatgtgcttg ggtgagggag agctcctcca tggctggagg  29700
cattcagaga ccaggcagtc gcttgtgggt ttgtgattag agtgaggttc ttttataaag  29760
ggagtgagaa gagaaggtct gtggatactt gagtgtatcg gtaattaaga aataaattgt  29820
gtacatccca tttctttcca cattttcctg ggctgtcaca gtggctgcaa agaaagcagt  29880
ccgtgaactg aactgtgatc ccagacaggc aagcacacca ggaatctctt ctcagctgtt  29940
gataatgagg gagcgctggg gagagaaatg gggtcctctt tgagtttcct ctgtgccgat  30000
acctttctct ttgttaaaac agctaattaa acactgaagc agtatagctc tcttactata  30060
cactggtagt catagttctc ttactgttct cttcactgac agttctctta ctatacactg  30120
atggtgacgc agaaattcag aattccccgc atgtgtcccg gtttgaaagc cactgtgctt  30180
tgctgtggat taggatcaga cagttgagtc ttgttccaac aaggaaagtt gcttattgga  30240
aagttttgct gcagggagcc ttgagttctg catcaggctt ggaagtgggc tctgtggagg  30300
tcagaaggag gatcccccac ccgcagcctc aagaaaaata tgaaaagtgg attatgcctc  30360
tgtagctata ttgcctataa actttctgca gaatgacagt attcatatcc tacatttttt  30420
caaagcgata ttaatcctga gacctgcagc taaagtcaag tagaatttag ggataattaa  30480
taggaggaag gtggggttgg aagatctgca tgattatagt cctctgatat aactggaaaa  30540
ttctttccat tagcaaggag ctttggttaa tataaaatgg acagattaaa cctaggcaat  30600
ttattttact cattgctgta tttttatttc agagctggtt gaaaatatta caaagtaata  30660
ttttaaagtg cttatctaaa ctcttactct gcattttatc attgggttat gaaatgactg  30720
gggaaagact tttcttgctt ttatttctca gtgtctactt ataaacatgt tttttgaact  30780
actgtttttg tgacaacatg cctttttccc agaaaatctc aggttaacat taaataggca  30840
ctggatgttt atctgatctt gtttatagaa acacaagaaa attttaacct tgtatatact  30900
ttactcaatt aactaggtaa gaggtcattg aaacatttag aattccactc tacatttcaa  30960
```

taattatcag gtgaaagcta ctgcatctac atcagaagat gtttgtaatt tatttaagaa 31020
taaaattagc tatgcaagaa atagtatgtg gagtcctatg tggaaatcac agaaaccctg 31080
acaacttgat gatctttccg caagctaaaa atatcactct ggatcacagc agtagaggac 31140
tctgtaaatt taatctgtgt gtctcctgta aataagtgca ttagcagtac acaggtggtg 31200
tcagagtcag tgatgatgga tagaaattct acataaaatc caggctcagt ggctcatgcc 31260
tttaatccca gcactttggg agtctgaggc gggtggatca cctgaggtca ggagttcgag 31320
accagcctgg ccaacatggc aaaacctcgt ctctactaaa aatacaaaaa ttagctggat 31380
gatggcacat gcctgtaatc ccagctattc gggaggcgga ggcaggagaa tctcttgaac 31440
ctgggaggta gaggttgcag tgagccgaga tcacgccatt gcactccagc ctgggcaaaa 31500
gagcgacact ccatcgcaaa aaaaaaagaa gtaagaagtt ttacataaaa acgtggagtg 31560
agcccaaggt gccatttatc cagcccatac acatcgtacc atgtacagag tggacaccag 31620
ataaatacat tgactgcatg ccacaaacat atatatgtag gcaccgttgc attcaaatac 31680
acatctgcag ccctaacaca tctttatttg ctaacgagca tcaatgtatt taaaaacaaa 31740
catgtttaaa ctagtgaatg attagattat aatgatctta attcataagt tttctcattg 31800
gccttttgta tacttcaatt gtaataccta gaaaaacagt tatgtccaaa ggagtgaata 31860
ggccttatct gaaacaggtg agcgtgacaa gtgttttctt acttatttta cttttcagat 31920
aattcatcct taaagtacat tagtttaaaa gtactgttta aggaaacagt acttggatta 31980
aaacttgaat cattgttaag gaaaactata ccttaacttc atgtaatcac aattaaacct 32040
cttcatatag aaggatctaa gaattttctg cagcattcac cagcaccaaa aagctcagag 32100
acatatattt ctttctctgt atatgtattt taaattcaag ttagtataaa ttgacaggca 32160
ggtcagagta atatatgatc ttctgagtcc ccttagtaat taaaagaaat gattattttt 32220
gcatgaaata tgataaagtg attttaagtg cctgataaaa agtcttaacc atgacaacca 32280
ttaaagatta catcaaagaa aaataagttt gactttcatt taccttggaa acagctatta 32340
actggtaacc tcaagaaaca ccatgaagag tcagtttgct ccacacatgt cttgtaaaag 32400
tcaaataact ggtggttatc cagtaatgac aagaggtaga agttacatcc ttgctgtctg 32460
attgaacctt cccagagctg gcacaaggct gggaagacca taggtgctaa atgaggaact 32520
acttaaagaa agaaaatgga atttcacgga caagaaaatc catgtccatt tggttctgtg 32580
acccacatcc tttgtatcct atgctttttt acacttggta catggttgca agattgcccc 32640
tgttttctac ttatagttcc atgcagcatg gatgtgggaa aaagtctcct ctgcaaaggg 32700
ggttaatgca ggtcactcta cgtatgtgca cgaggtcgtt ataaagctcg aaaatatggg 32760
ctcaccaacc aggtgatttt tttaattatc caaccagaag acataacata taggggaatc 32820
aaaagaaatc tctgagtaaa ataatgataa caggtcaaac tttgcggtcc cacgtgaggc 32880
tggagatgcg tattgtcttg actttgcatc tacaagttta acaaatgatg ctttctcagt 32940
ttacctctgg aaatggaaat tagcattgca aatgacttca tgaggaggta gaagctatct 33000
gtgaatttcc tttcgctgtg tttacgatag actctcacgt ctagatgtgt catgtattat 33060
gttaaattgg tatgtcttga agttataaag cacagccctc tataagtata tatattccac 33120
ctctttcaaa tcggatggta cctatccttc aaactgctat ttaatgactg tctgctatgt 33180
tcaaggcact gctctcaatg ttaatacttg atgagatcgg gcgcgttcaa ggtggcatgg 33240
ccgtagactc aatgttagta tctgaaatat ggcctacgag ctgagttgtg aatcaagtta 33300

```
atagattttc ggaatgttaa ggtctaaacc agtagctctt aactgagaca atcctgtcct  33360
catctcacct gggagacatc tggcaatgtt tggagaacct tttggttgtc acactggggc  33420
atctagtgag tagaggtcag ggatggtggt aaacaagttt ttttgtttgt ttgttttgtt  33480
tttgagacag agtctcactt tgtcacccag gctggagtgc agtggtgtga tctcagctca  33540
ctgcaacctc tgcctcctag gttcaagcaa ttcttatgcc tcagcctccc aagtagtagc  33600
tgggattaca ggtgtgcacc actacactca gctaattttt gcatttttag tagagacggg  33660
gttttgccat gttggctagg ttggtctcga actcctggcc tcaagagaac cgccccccttc  33720
ttggcctccc aatatgccgg gattacaggt gtgagccacc gtgcccaggc taacattctt  33780
taatgcatag gacagccccc accatacaga ggaatcccca gcccagaatg ttaatagttc  33840
taaggttgag aaacccaagg ttaagccaag tcaacttatc tatcttcttt aaaattgcat  33900
aagaatgcag tcctgttctt cattcctctt gctttgcagt taatgatcct ttgcctggac  33960
tttctaagtg cccagaagag caacagccag catgcaggat ggcattcctg accagttgca  34020
cttggcctag cattccaacc tcacctgcct cagcttgttc aacctgaaaa cctaccaagt  34080
gaaagcaaga gccacgtgaa gacgccttag ttatatgcac ccacccagac acttgctcag  34140
aaaggaatca gtggggccct ggccttagaa actggctcct tcactgctgt agaaacaaca  34200
taaatttaac ataaaacacg tgcttttctt ttttcttctt actttttcct gtcttggcaa  34260
tgcaaggatg ccattaggta aagaaatcct tcaccacact aatcctgcag agccagaaga  34320
gaaaccagct tgttctaacc cagctttgtc atggagagaa ggcagctgct ccagtctgaa  34380
ctattctttc ttttggtagc agcctgccca agggtgaaag tgtgtttaat agtttgaatt  34440
acacaagtga acagtaaatg tatgcctgtt tctgctttat gggactttga aataatgttg  34500
tttgtgccaa ggttttagat tactatacct aacaacctag aaaaagaaat gaaaaggaag  34560
ccttctgcca ggcagaggtc actacgggcc tggagctggg cacctgactc agcagctgcc  34620
cagatcccca gagctgagaa gtcaccatgc atttgtggtg cttcgagcga gttaccagag  34680
tcctggaaca gagcagcaca cctgcggggt gtccccttgg catttgggca gggcaggtga  34740
ccaagggtct tgttggaact gaagtccagc ttgaaaagca aatctggttg tgagctagag  34800
tccagtaaca cttgtttccc gccgcccccc gcataactcg tgtgtcctaa aatacaataa  34860
tttcttgaac ttcagtcact tatgcctata agcgggcata caacaggggc acaataaatg  34920
tttgttaagt gaatgaattc tttcagaact agatgggatc ttagtccaac tctcttattt  34980
aacgaggtcc acagaggttc tgcgattgtc taagaaagaa ggctgtgttc atggcctttg  35040
ttgtttacgt ggccctgtga ttctcttggc tccgtgaaag tcctgatgca gacattccgg  35100
ccatctagaa aggcatgcag acaagccatc cagctggcat gatcctgagt ccagctttct  35160
ttaaaagagc ttccaaaact gcttaagctt tgactgcaca aaacctgcat cacctccagt  35220
tgagaaactc aagagaataa gtaagttatg gagttggaga ccccagctta actactagtt  35280
ttaaaatagt gaaatcaaca ttttcaaatc tttgacttca ctaagattta ataaagttta  35340
ttaatcatat attatgagtt attgctctct ctttatgtct gtaatgcagt tgctcctctc  35400
tgtataaatt aataagtttt agagatccaa aatgagaatt ttaaaataaa ttacgtatat  35460
tttaatcaag tttaatttga ctatatccag ctaaacaatt gattgaactt cacttgcttt  35520
tctatgacag gttttttgtt cttagtaaaa gaccccagtt ttctcacttg tgaacagaag  35580
gggttagact tcatgacagc taaggttcct tccgtctcta acaaaagtgg cctgaagaga  35640
ggcttctaga ctatactcac ggtgggttct tgggacctca gagtcagctc catcacttaa  35700
```

```
gtggctgtgt gattgagtgg agacacctca atctctttgt gcctcagttt cctcacctgt  35760
cgagtgtcaa catgatggca cctaaagctg ttgagacttc agaaaggtaa tgtgtgaaaa  35820
gtgaaaagtg cctggcatcc aggaagtact caataaatac caactatttt attgctgcag  35880
ctgttcttat agatgtgatt tctagaacat tgccttctaa tagggtagcc atgggccaca  35940
attgttggct gttcggtgtt tcacatatgg ttagtccaaa ctaagatgtg ttgtgagtct  36000
caaatacaca ctggattgtg aagacttagg acaaggaaaa caatgttaat aaaatctcat  36060
tgataacttt taaattaatt acatgttgaa atgaaaatat ttgggacata ttgagttaaa  36120
taaaacagga gattaatttc ttctgtttct ttctactttt tttattagtg tggctactca  36180
aaaatgtgac attatgtatg catctcgtat tacatttcta ttggacagca gcgctctaga  36240
cagtactatg ggtagtatct gtggggaggt tctcagaaac atgtcgcatg ctcttttaga  36300
accttaaagt attcctagtc tcctctactt ccagcccttg gctcttgggc ctcagtcttt  36360
ttacttttgc ggctgtgttt ctctgaaggc ttggcattag tagattgaaa agaataacca  36420
tctagggaaa tgtgaattca gtttctttct gacattctgc tctctacaag gggatattat  36480
gtacacataa acctacttcc aaaataatga agtgaggcct aattccttac tcttcagaga  36540
gcccactgtg gaagtgtcac tgaccttgtg tatgggctgc ccttcatggc tctgggagtc  36600
attataaagg gcagcatttg gcgtggtgcg tcctaagcca gtgtttctcg gctctgttcc  36660
ttagacatgt gttagtgtta atagatgttc ttggaaaaaa aaaaaaaaaa cagcattctg  36720
aggtcaaaca tgctcagaaa gcttggaatc tgcactacgc ttctcgtaca catttcatat  36780
taaagatttt ggaaagtcct gcaatacaga gccctgtcta atattgccac aacccacaat  36840
tgctcaaatg taaatagatt tgagtttatt cacattcaga tcacctctta aggccccacc  36900
tcccaatgct gtcacaatgg caattagatt tccacatgag ttttggaagg gacattcaga  36960
ccacagcagg ggaaagcagg gtacttgctg ctttgcaagt gtgtccacat ctaattaata  37020
gtacagttct tactcttggt gtgtccggtg atattaaaaa ttaatgtgcc ttatttagat  37080
aagtaacata aaaatcacaa aatgtatgcc ttagatttat atgtatttat aactagtcta  37140
tttcctgaaa acagttgaga caccttgtaa aagttaccgg tacgataggg ccattccaac  37200
aaagctgtaa agtggtgata acacagtcat aaagaagagg agatagctct gggagaaaag  37260
gtggcccaga aaccagctct gagcctcatg gctgcaggca aggtctgcag gttcctggtc  37320
ctgattgcag gccatttgct gccttgagtg gtggttacac aaggccagcc ctgggggtat  37380
cacccagaac acctagtaca cgaatttcag tttagaggac gaagcattac tggagtattg  37440
ttatgcagga aaactttttc ctaaaaatgc cctgaaaaga gagtagccta atgcattcaa  37500
tcaaaatgtt tttaagtgga aaacatattg tgtgtacttg atctggcctg ctgcttttaa  37560
aagattaaaa ctgggactgg gcatggtggc tcacacctgt aatcccagca ctttgggagg  37620
cagaggcagg tggatcacct gaggtcaaga gttggagacc agcctgacca agatggtgaa  37680
accccatgcc tactaaaaat gcaaaaagtt agccaggctt ggtggcgcat gccggtaatc  37740
ccagctagtt gaggggctga ggcaggggaa tcacttgaac ctgggagccg gaggttgcag  37800
tgagctgaga tcgcatcatt gtactccagc ctgggcaaca agagtgaaac tccatctcga  37860
aaacaaacaa acaaacaaaa aaacactggg gccaaagaac tctgtgtgct gtatcaccta  37920
accacatttc atgacacggc tagagaagaa tcatgcaaat aaaaatttcc aacatgttcg  37980
taaactggga aagtatttca ctggggagtg agcagaaaag taatactata acctctatat  38040
```

```
ctagacaaat gtgaattcag tttcacatat aaatatataa gtgaaaaaat atataaatat  38100
aaataatatg aaataatggt tatctcacca ctttctacat cttttgtgaa tattttatag  38160
tgctcaaata tattagtgca ctagtatatg tacattacat taaataacta atcatttatt  38220
aggaggatgt gcttgttttt tgctaataaa gatgataata aaaaaatcct tagacccccc  38280
ctcggtttgt tttcagttag gaattaggga tatttataag aatatcttta aatgacacat  38340
gccttgctct gggacgaggc atctgcatgg gtgacacata tgtgttgtgt gtacaggctc  38400
ccagcatttc cagggccctg ctcagaatgt aggccttact gattcttaca gagttacaag  38460
cgctggtgag gttggcgaag tttaggtaaa cacagctggg aatgccccat ggcctctggg  38520
tgactttgga catcactgaa ctttaccctt agagatgcat acctgcatct tttttaccct  38580
gatagggcct tccatgatgc tttcaaagtg tttttgtctg cttttcggtt aatagacttt  38640
cacagtagcc aattgaatat attggttaaa tgcatctctt tatacacaga ctggattcaa  38700
actgaggttg tgtctctccc tggctgtgtg acgttgggta tgatccaagt gtcagattac  38760
tcaacttcaa aatgaggaca gagcctttcc cttctagggc tgccaggaac attgaatgag  38820
agagtgctgg cagcttagta caggtgttca ttgctcttgt atggtactgt ctgtggcacg  38880
gctagataaa atacagtagc cactgattca aatttcaact gaggagtaaa ataaactgaa  38940
taacttagaa aagttttctt cttttgaatg actctaagaa tttaaggagc atgtgagtgt  39000
tgatggctct aaaagggtaa cagagcccaa ctagctcagt tctcagcatg aaaatagtca  39060
tatggcacag actcagtgga gtgggtgcac ttcaataact ggaagcacag atgccctaca  39120
gcagcatcaa agatggcact ctaaactact ttcaatcctt taaaataaat ggaaacgcac  39180
atttagtatg catatgacaa cacgaaggac ttcgattttg ctgatgcaat acagttttac  39240
aggatttttt atactcaaat tagtaaaatt ctgtattgca tccaaattat aaattataat  39300
atcatctaga ttggacatag gaataacgac cactggtatc tgcccagaaa gctctaccgc  39360
ctgtttataa gctcctgcag gagacacaaa aagaagagaa tttgaatata acttgaaatg  39420
accgtaatct cctgccccaa ctcatttcat taccaaaccg cctctttctt cattatttct  39480
cctgaagcac aaatctatag agaactcagc tgccagtctc tcccactgca ctcagcagtg  39540
aaagggttag gcctaggctt ttcaaacaga ccagtgcttg tatcagccct taaacatctc  39600
tggagaagga aatgggatcc ttctttggta attcattttt gacagttggg gattaggtgt  39660
tctgtatctg gggggccttg ctgtcttctc tcctcctcct cccactgcag accctctcct  39720
cccctcccct ctccagctct ctgatgactg cttcatgctc cttccacctg aggactgcca  39780
gcacagccta ttgcaggaac agccaatgag ggctggctg tgctctttta tttataaaat  39840
tataaactca agcaaaatct agactatgtg tccccaagat cagaggagca caaatccctt  39900
gcttacagat tgcatggggg gcacattctt taaaattggt ccctgatcta gactctagcc  39960
tgagaatcat ctttaagttc agaatttcca ctcatgacct cacatctgtg ggctcccaca  40020
ttgtcttcca aaacacacat ggcatctggc atcaccttca cccccaccct cagagcctca  40080
tctccctgca ggtagatagt caaggcaacc tcttcactct tctgccaagc ctcctctcct  40140
cagctcttcc cttcctctct ctttttgaaa atatttttaa ttgtggcaaa atatacacaa  40200
cataaaattt accatcttaa tcatgtataa aagtggagtt cagtggcatt aaatacattc  40260
acgttgttct atagccataa acaccattca tctccagagc tcctttcatc ttgcaaagct  40320
gaaactctgt ccccattaag caatggctct gttttcctcc gttcccccag cccctggcca  40380
ccatcctcag ttttctgtct ctgtgagttt gattactcta agcacctctt ataagtggat  40440
```

```
catacaatgt atctgtcttt ttgtgactgg cttgtttcac tttccataat gtcttcaagg  40500
ttcatccacg ttgcagcata tggcagaaca tctgtccatt tccaggctga atggtactct  40560
tttgtacgtg tggaccacat ttcatttatc cattcatcca cgggagggca cttgggttgc  40620
ttctgctttt tagctattgt gaataacgct gctatgaaca tagctgtatg cctttgtctt  40680
ttaaagccca aatctgatca agtcactccc cagcttaaaa ccttccactg ctccccagca  40740
gtgggataaa ggccagtctc ccctgtaggt ctctcccgcc agccctgctc agtcttcttg  40800
cttgtcatcc ttggctaggc cttgcattgc catagccctc tgcctctgtt cacgctctct  40860
catcttggag catgagcctt ccatcatctc taccagatga actctcattt cttctttcaa  40920
aaaataaaaa acccaaaaaa cccagagatc ccaactgtcc tggtgtctgc atagtctgca  40980
gcacacgccc cctccatggc ccttcctcca taagcagaat cactcctcac tgttcctgca  41040
gcacctcctg tgtgcccaca cagctgtcct gcggtgggct gtgtgtgtga gtgtgccccc  41100
tctaggacct gagctccttc tggagggtgg gcacagcatc cattcattct gggaatcctg  41160
gtcggcacca tgctagaact tctgcaagtg agtgcctttg gtgctggccc atgggagagc  41220
tgttggtaag gcatactttt gcagattcca gttgctgctg aggttgttgc tctttgcaca  41280
agtttcttct agtcaccagt gaagtgacat gtgtggcagg catggcccag ggaggctttt  41340
tcataaagaa gaggttgaat ctttggggct gtggtttgaa tatgtccctc aagcttatgt  41400
gttggaaact taatcccaaa tgcaatagtg ttaggaggtg gggcctaatc acaggtgatt  41460
aggtcataag gctctgccct catggatggc ttaacatgtt tagtgaggca gtgggttagc  41520
tattgtgaga gtgggcttgt tagaaaattg agtgcagccc cctcttgctt gctggctacc  41580
atgctctctt gcttttctgc cttctgccgt ggggtgacac agcaagaaga ccctccccag  41640
atgctggcac catgccctgg gactttccag ccttcagaac cacgagccag acaaatttct  41700
tttctttata aattacccag tctgtggtat tctgttatag aaacacaaaa tggactaaga  41760
caatcttctt tcatcaagtt agggtaccaa cctttaaaga ctgccagtcc aaggttaaag  41820
gaaacttttc aagagcagtc caaacatgat ctggccctca gctactctcc agggtcatgc  41880
caccctatca cccactggct cacacagacg ctgaccactg cttagtttct caaactgaag  41940
ttttcctcct cagagctttt gcaaaacctt ttctttgcct ggaaaactcc ccccacaaat  42000
ctttagttgt aggttccttc tcatcttgca gaattattag tttgctcttc aaatagtctc  42060
tccagctaga ctatcaactc caggagggca gagttcttct tcgcttcctt cacccatgtg  42120
cccactgagt ccagaactgt atagcagttt gattgaaaaa atccacaggg tggaggatga  42180
gaggaccctg gatcccagcc tcacagcctc ttacttcacc tgtgtgattt tggtcaagtc  42240
ctttattctt cctgggcttt agttttccct tatctaaaat atgagaaaag ttcccctctc  42300
ctgggtattc tgggagactc atgtaaaagg cactgagcca gtgcagcaca tctatgacca  42360
ggaagggtca gcttcctgcc ttgcatgaga cacacattcc cttcttcatg cacagttatt  42420
catgagttaa atatgtattg agaagtgggt tctcaggaga tgatgcatcc acagcattgt  42480
ttgtatgcct ctgtctttga tgtccctgcc tgagtcgccc actttagagc ccttctgttc  42540
ttcagaaacc agacttttct ttcaatagtt tcagtaatca atcgatcaat caatcaacca  42600
atcaacagtg ataataatca tgagtgagcc cctgcccgtg ctggctgtgt cctgctgaag  42660
gcacactaag tgctgccctt cccagaagcc tcaggaagct tgcgaagctc aggtgcatgg  42720
atgcctggtg gaatgaggaa gggatgcagc caggtagaga aatgccctgc catcacttgc  42780
```

```
atcagcatct gtgaagagct ggccaggctt ttgctcacag tggttgacac agtcaaggag  42840
caagggcccc gtaggagagg ggagtcaagg gctccgggtg ggaatggagc tgggggctga  42900
tgctggcttc tggagcactg taatgtgact gagaaaggtg aaggagccgt tctgaaaaag  42960
aagaaggcag gagctcgcac agctcttgac tcatcttgac ttctttttcc tgcttcatcc  43020
aagcaggtcg actctctcgt gatctcagag acagagtgaa gtcatgagtg ggaggggagc  43080
acagaaaata agaccttgat tcccagcatt gggagactcc ctgctcccct gagtctcgga  43140
aaatagcacc cttcaaatgt tttagggatc cagatttgat gaagagatgt tattttggct  43200
tttagattct taggagagat ttgtctttct caggtcagga agaaaatgct gcccgctgca  43260
cattcttcgg gacagactct tttaattatt actagtttaa tgtatgtttt gcttagttaa  43320
ggaaaacccc tgtggtttct tgacgtgctt cagtattcta actcacagct gattcagttc  43380
agggggctgg ggagatgtcc tcgacctctg gaaaggaggg tgcatctcta gaaataaggc  43440
taagtatgcc actgacactg tctgcataaa cgtgtgtgat ctcaggtcca aaggatgggg  43500
cctggtctaa gccagggacg tgggaaatca ttttcctgtg gcaacttgtg aagaccattc  43560
tgtgaccttg gtgtctctgg gccttctctt agattttcta agttggctag tcagtggagc  43620
tgccatccct cctttgccca tgttctactc ccagagttcc tccaagaaat tgcggagcaa  43680
tgcctgtttc atgagagctg agtttgctgt gtcttccact tagaaacaac actgtggacc  43740
aggaggacac acagctccca gggccatcac cacacaaagt gaaggctggt gaatccgagg  43800
cttctagccc ttgccgggcc aggcccgcag cactccgctc cccaacccag ccgctgcttt  43860
gtcgcaggaa cctcagcagg gcagggtgtt tcctaggagg acatccgatt cccagccatt  43920
cctttcagtg aatcacctga gctcacattc ttttttcttt tatttttgaa gctcttagcc  43980
aatctgcttc gcgatgaacc agttttgctt gaagcagaca aacccgattg tcaggagaca  44040
gtgatgattt cttcagtctc tgaggaagag ttttcatttt ccccaattcg caaaaaaagt  44100
caggtccctc cctccctccc tctccgtaga atattttcca tgtgtgttaa caatggctga  44160
gcgtggtaga tgccaggaat ttctgtcaac cctcaaagag gaaagccctg cctaatggtc  44220
tgcccgttct tgttcactcc ctgccccagg ctccccaccc gccttctttc tggaaggtat  44280
aaaggctcct gcttatacct ggcactgcac gcttcgctcc ctctgatctc ctgactgtca  44340
tgcccagtgt ctcagcctat cattctacct ctaactcgac cttgagtgac cttgagcaag  44400
tttctcagga ttccacctcc aagtcactct ccctttggga tatgcagcac taagttaagc  44460
ttgcctggaa aacatcactt gaagctggaa aaccactttt aacacagcgg gaaaagctat  44520
ttgttcagac aggagtgggg tgggtctggg cagagcactg ctctaacttg gccatgccgt  44580
ggcagcagct cctttaatgc cactttttcc tggcgcgccc gcggggcctg gagctcagaa  44640
agaggggaac gctccctcgt ctctcaacag ttgctccaga caggtcagca aacatggaat  44700
tcagaatgtt cattaaacac tggctgtgtc ttttgtgttc aaaagcaaga cactctctct  44760
gaaccatggc cccacagaga gtgcagaatg tgtgaaacct gccgggaagg tctggacccc  44820
ttgcggggca gtgggcagca ccgtgcctcc gttcacacca ctcacatggc tgtgcctctg  44880
cttccttctg gcatggctgc ttcttcctca ggtctcaacc atctccctca gatgctcttt  44940
cccatgtttg tggctacagg tccccgtgac ctgcagaggc agagcactca ccagcagccc  45000
agcctcgttg cgcacccatg tttgcatttg caggccctag aaccactcca agctccgtgt  45060
ggcgagatgc accctcctgc ccttcactgg ggagctgccc tcctgttcac agcggcacct  45120
gagtcacaca tctggagcca tcctggactg cctcatttcc ccgatggggg gtttccctga  45180
```

```
cttcatccat cctgtctttt gggtccccat aataactgac atgggtcggc ccgtaccagc  45240
ccctgtgaga agggctttaa ctgccttccc accccctgct catcttagag tctctctata  45300
gtgctgctga aagaatctct aaatcagtgg ttctcaacct cagccgcaca ttgagaatca  45360
cctgggaccc ttaaaaaaat cttaactctt ggtccaagaa ttctattaca atcggtctgg  45420
gatggggccc tacaggtatt tttttaaagc tctccagttg gtaatgcata gctagagttg  45480
agtatcgctg ttctaacgtg cagatctggt catgttacca gccttttagg tggtcttctt  45540
tggctttctc tatctaaagt tcaaaaccga acatgtgcgc attcagtgca cccattttca  45600
actgtgcatt aacacattca gcccaccagc aagatttatg aaccattttc tgctgttgta  45660
tataacatat catatgcata atggcatagg ttattgtttt cttcaaaata tatgagatgt  45720
gagtccttct acgaactgac tcacactgat tgcccaactt cctctctcga ggtctcatcc  45780
tctttccctg cagccgtctc cctcttgcac gcacacacac acacacacac cacacacaca  45840
cacacaccac acacaccagg gtcgatgcca tctaccctgg acttcatctt gaactccttc  45900
gagtgtgagt cattactcct ttgtgcacct ctgctttctc ttctcaagat gttcacctgc  45960
ttgaggtcag ttccttgagc gtcttccact tgccatgttc accacagtgc tcaacatgcc  46020
tgaatgcatg gatggcgact tctcagatcc tcagtctcct catctgggta ataaggcatt  46080
gggttggcgg gtccatctgg tttcttccag ctctgagagt gcatttgctc tgtgattcat  46140
tcgttccaca acacttcacc aattaaagag agggtacaaa aggtgaacat ccttggctcc  46200
cagcagatgc tcctcaaaac ctgaaaaatc agataggtga gggaagattg aatgaaaggc  46260
ctcttatgat tctgcagcaa ttttggtggt ttaagaactc tatggaaaaa tcatcagtat  46320
ttctggaatt gaagtaaaat ggatagtgag cctctgtgta tgtgaaggcc cgcatctgga  46380
acatgaaaga acctgtctga tgtgttctag tcaggaaagc aggtagccaa tactatttat  46440
agaatttaca gaaactgaag attttgtttc tactgatttt caaaatagta ttatgtctga  46500
ttttttttcct cagaaatata cttcctgctc ttctcaacaa actcatttga aaatatgatt  46560
agaacatgat agaattttac tcatttgcca actgcggttc ccatttcaca tattgttaga  46620
attctgcatg gtggctttgc cctttaacca ctaactgata aatgatgtag ttagctttta  46680
aatgtgtgga aaaatataat ttcaggttca accataggtc agaagtacac gtgttttgtt  46740
agtctatttg tctctcagtc atctcatgga aaattctcag cttttggtat ggaaataatt  46800
ttcttgaagg caatatttgt tgagtgactg acggaatgaa aaacgccagt tgcgtaagtg  46860
tgaaaaagat ctgggtgttt tcattggatc caaattccac atgagccaac aacagcgtgg  46920
tgtggaggct ggagcacatt aataagaaca gtgtcctaaa ttcaggaggt aatgctctgc  46980
ccatgccctg tgcagctcag acggtgtgtg cagtgcagta tgtaacccag ggcacatttc  47040
aggggcccac agggagctgc agcttgtaag gtggagtgca gccaacagag cagagagtca  47100
gaatccccgc agagtggttg aaggcacaag gatgcgcagc aaggaagaca gacttatagg  47160
tggtgcgact gccatcctct ggtactgaag gtgctatcat ggagggaggg aagtagattg  47220
accctcctgg ctccagagta cggaactcag acaaacggtc agaagcttac agggaggcca  47280
attttggatc aactttaaga agaatttttt aaaagctaga gcaatcctaa aatggaattt  47340
gctctttata aagttgcgaa tgcctcaccc tggaattgct taagcaaagt tgggacgggc  47400
agttgtgagt aatctccttt ccaatccata cccgcaatca ccagaaacgt ggacttccct  47460
gacactgagc acctcttaat taagcatctc ataagtgaac aaaacccagc ccttcaaaga  47520
```

```
agtcacttta tttatgtgtg ggtctgcagc ttggatttct tgataatgtt aaataaaact  47580
ccatctactc ttccacaaac acttcaagaa acctaagact tttggccaga gtaacaccga  47640
ggtttgagag aaaggatatg tgtgtgagag gtgtggtttc attagaacat attatttgac  47700
ttcatgttga atcaacactt ttgtgcaaaa tgcagtttta ccagcctctt tccttgtttt  47760
ggtcacataa tttaacttaa cattctcggt acttgatttt ctaacataaa atgggattga  47820
gaggggaatt ttgaagttcc catggtctgt cctctacatt ctgacagctc attatctctg  47880
cggtattgtt ctcacattta agtgaggtta gcggaggcag aggcctctca ggcctgaaga  47940
tagcctctgt tttcagggaa atactagact gtgagatctg tgacactgaa gcactaagtt  48000
catctcacaa aagcaacgtg ctctttttaa atggttgatc aaagttactt tcaaaaggaa  48060
gtgttagttt ttgttattag ccgaaacaag agctgcttta atgtagtata tttaaaatca  48120
tatctcaatt aagatgttat tcaaatacta tttgacccac caatctcatt actggatata  48180
tacccaaagg aatagaaatc attctattat aaaaacacat ggctgggcac agtggctcac  48240
gcctgtaatc ccagcatttt gggaggccga ggcgggtgga tcacgaggtc aggagttcaa  48300
gaccagcctg gccaagatgg tgaaacctca tctctactaa aaatacaaaa attagccagg  48360
cgcggtggca ggcacctgta atcccagcta ctcggaaggc tgaggcagga aaattgcttg  48420
aacgcgggag gcggagtttg cagtgaacag agatgaagcc actgcacttt agcctaggtg  48480
acagagcgag actctgtctc aaaaaaaaaa aaagaaccac ttgcatatac actattcaca  48540
atagcaaaga cgtggaatca acctaaatgc ccatcggtga tagactgcat aaagaaaatg  48600
tggtacatat ataccacgaa atactatgca gccataaaaa agaacaagat catgtccttt  48660
gcggggacat ggatggaact gcaggtcatt atccttagca aacgaataag aaaagaaaac  48720
aaaataccgc atgttatcac ttataagtgg gaggtaaatg atgagaacac aaggatacac  48780
tggggcctac ttgagggtag agggttgaag ggagagaagc agaaaaaata actattgggg  48840
tactaggctt agtaccaggg tgacaaaata atctgtacaa caaactacta tgacacaagt  48900
ttacctgttt aacatacctg cacatgtacc cctgaactta aaaaaatttt taaaaagatg  48960
ctatgcaata aaattctcaa ttaagaattt aacttggtaa atgttcattt aatgatctaa  49020
aaatatgtgt ctggatggct ctagcaaaaa aataaataat aagtttctca gagatggtaa  49080
ggctgaaata aatggggaaa aatctgaatt gtaatccttt ttctgttgga cctggtgttg  49140
gggtttcaca cttgtgggtg aatgtgggcc tcctgtgagc accagcacaa aagactaaac  49200
tgaacaaaag attaaatgtc acctctaaaa ttctgtgcaa caagacttcc agccacagaa  49260
tgtgcaactc agatttccaa gtaaaaacac accaggaagc agatcttaga tctctgttat  49320
ctccttggca ccagctggta ttcatcctca atgctagcta gagttgaaat aaagagtgaa  49380
agaactttct cttttattac ttaataaact tcctttttg agctgtttta ggcttacaga  49440
aaaattgagt ggcagtttca gggagttcca gcacggcccc tgtttctttc tcatggtccc  49500
tgcaggtttc ccctattatt aacgtctgtc attagcatgg cacatttgtt acaattaatg  49560
agccaatatt gatacattat tcactaaagc ccacaggttg cgttaggggt cattcttggt  49620
ggtgtacgtt cttcaggtct ggacaaatct ataatgacat gcattcacca ttactatatc  49680
acgcagagtc gtctcctggc cctacaagtc ccctccttcc ccacctgctc actcctcctt  49740
cccaccctcc ccaaactgtg gcaaccattt aacttttgac tgaatggatt tattcttatt  49800
ctgccttatt gtatgtacac catattttaa taagataaaa taatagtcta tagtagactt  49860
ctgtaaatac tcaatgaata aatacttgca tgaatgcagg aaaaatcaat cagtcttgca  49920
```

```
ggatttctta tgcgttacat cgtccttata agaaagcagt cattctcacc gagatgtgct  49980
gagcagatac tggacatgtt ctgacccaga taagggctgg gtggaagtag ggctggagac  50040
acagagaccc agtgccaact tccaggacct cggaagaact gaaggcagag aggtcctctc  50100
agtgtggact gggcctctgc tggcagccac cagcgggcac agagctgatg tgtgttatgc  50160
cacgtgggga aaacctacag acgattctga gaaaggctca cagggacacc ctctgcccct  50220
aaaagaacaa tttaactcta atttatttct gtcactctgc attttctgac ctttcccaag  50280
tgtacagttt tatatgcatt taactgccaa attgtcatgt gagattatat ggttatattt  50340
cattaatata ttctagtttg ttcagctgtt cttactgggt gaatttgtgt ggtttcctga  50400
catttttgtt tttagtagtg cctcagtagt tttatacata attacgtttc ccttctggat  50460
tatttcctta gtatctagtt caagaagtga aatcgctgga ttcttgtggt aaatttttga  50520
atttcacagt ataatgctga ttttctcaaa gtctcacatt ctaagaaagt ataatgaggc  50580
aaaacaaaca acaaacatct taagttgatt ttttcctagc atcttttcct tccatctttg  50640
cttgtagaat ctagactatt tcatgaaccc aagatataat cagtatcctt cttcagtatg  50700
gccaaagtga gtttctcatt attttacctc cccttcagga aatgactttt catcttgtgt  50760
tttgggagcc atagatggtt ctgggcagga aactggcttt ggatagaccc agcatgtaga  50820
tggctatttg gccttgctcc cagtataacg atgcagttcc ctgtgaaagg gtatgagtag  50880
gttttggggc tctggatacc gtgtggcctg aagagacaag ggctcaatgc caactctgcc  50940
tgtttccaac tgtgtaacca tgtgagcgtc aaaaatcatg gacgtgctct ggttaacact  51000
gagtgggagc tcaacaaatt attattttta attgttactt ggacatggcc aagttgacta  51060
cactttatgt tctgctacct gccagtctga aagtgacgcc acagaaggtg aaccgcatgt  51120
tgggagatgc tcctcatctg cttaaatgag gtgcaaacac agcccatgcg cctgctcttc  51180
atgactgtat ctgtaccagc aatatttgta ttggcaaatc acatgcccca gtgggaacta  51240
cttaagggga attcaatgga tttcattcct tttatgtaat tggccactta gtaatagacg  51300
tgtaggtctc ttgtgtggat aaggattctg ccttttatgt aagatatgtg ttgcaattca  51360
gctttcaggt cccagccccg ggaaggctcc aggccttcac aaactggccc acccacgaga  51420
aggaaagcaa ttgtccaaat gtgggtagct tttcttccca ctgttgtcag ctgcttccaa  51480
ttagccccca tatacataat cccagtttgt gtctgtatca gtacaattct cccatgtcaa  51540
tgtgaatttt aagccacaga gggaaagggg acagagaata tgctttcatt cagctctcct  51600
cgtctcacac ctcttgccct gcatgcattt ctttgctctg attaaacgag cattttataa  51660
gccacatttg ctgtgtgaaa ggcaaagtct tccctcccac ggatgacggt ctccagggat  51720
gtgtgtgtgt gtgtgtgtgt gtgtgtgtgt gtgtgtgaga gagagagaga gagagagaga  51780
ctgtaaacat atatctctgt gaaacttcat tttccatatg tgaatttttg gaaccgagac  51840
aaatggaact tagctaaaag atgggaaagg tagactgact ctgacttaat ctacttaacc  51900
taccaggcaa tttataactt gatggcctaa tttttgcagc acccagaagc aagcctgttt  51960
cagcacggca aaggctcagc tgctaagtgg gcagcattgt tggaggtgag cagcttaggc  52020
tgactgttca tcaaaggacc aagcgcttga ggttcgctca tcgctggagg ccagagtggg  52080
gagggccatt taactgctca aggccatgga actctactgt cagtttcagg gaaatttggg  52140
accctggagc acaaaccaaa actccaatta accaggagag gaactcgatc cccaggagat  52200
aagtgaagag taagaagtct atctttagaa acaagagatg tccaaggcta gaaagatggg  52260
```

```
gaaggagggt ggaactgttc tggaagtggg tctcaatctc agcaccagca gctctcaaga  52320
ctttctagag aaggaaactt catttctgaa ttaaaattag tcttcaatga catggcaggg  52380
atttcggcac actctcttgc gtcataggcc actgtgttgg aggcaggagt gttggctttg  52440
gaggcataga gattaaaatt agagtaacac gtgagcactg aaaaggttaa acagtagaga  52500
catggaggac tcccgacccc catgtacccc tttcttaacc ctttaattaa gatcacagcc  52560
ctagaaatag cttgcaaaat aattaactac tgatcattta taccttagtg cttctgtgag  52620
catgttttct ctttcattgc tgctcatctg catggaaaaa tgtgcatggg tttctgaata  52680
taactccatg gtgcttgctt ccattatatt tgtgccattt ggatcataac tgataagcaa  52740
ccaaagagtc ccatattact gcacgttccc atcgctattt tatgtgaagg tggtcctggg  52800
ggctgttctg aattctcagt ttcctttttt cccctcccca gttctttgaa aatatcagaa  52860
acggacttgt ggcatctttg aaaagctact taaaatgtgc tgctgtgctc tgaacttgaa  52920
aatgtgcttt taatacaaag tttgtgcagc ccttgctgct catacgagat gaatcttacc  52980
atgtggtgga tgcccgtctc atgccaggca ctgtgctcta agcccattgg tttatttcag  53040
tgcttgaaat tggctttcga gagaggcacc acggttccct ttttacagga gaggaaacac  53100
cagaggatca gagatggaga gtctttctcc acaaactcac agaccccaaa ggcaagctca  53160
gggttgtcag cttccaaagt ctgcctgctc caggacctca tgttgcatct ccattctctt  53220
cactgagggt caaatggaaa gaacacatgg gggtcaagtt tcagaaaata agagaaatga  53280
agaaatatgt gcccggaagc aagaacgacc gacctcatta aactggctcc cttcacctcc  53340
tctcacatct ttttctgcct tttggccaag ttttctctcc cccgcatttc ctccttgatc  53400
tcgtttgaat cctcttccct ggtgaagtca tttaggttca ggctcttatt ttactttggt  53460
ccataattta gatcgaacca catgtgctga tgtgattgaa acgatgtgga attctctgga  53520
cagagataga attatggagg ggttagtgtg tgtgtttaag attaaaagac caggtgtatg  53580
ggaggaaata taatgaacaa aaaatagtat tttaaatgaa tactaaactt gcactcatgg  53640
aaaaagttct cttcccatga ggttctcgca aagcatttta ccatcagcac acgcagtttt  53700
tctcagtttt ctgagatggg gccatcttga atccaacaga caacacacag catcagccag  53760
actaacacaa aggacgtcat gggcatggac gtaaatactg gtgtcaacac taggtctgca  53820
cctcgagagg agtggagcaa aaggatggag tggcagatga aggtatgctg ttcagaaagg  53880
aggcagaaat gaaaggaaga ccatcagtgc gctccacagc ttgaggaccg tcctggaggg  53940
caaatgccag ctgctcactt ctgaaaagaa aaattccagt gaaatgagta cagtcattct  54000
taggattact cacttgatac tgtgtatgtc tcttcttggc ttctcatctc cacacaaaac  54060
cctcaggtgg taaaaatcta attaaaaaaa ttatataaag tcttgtagat ttattagcct  54120
gaacataata gatttttttt aagcacgtta agtcttccat ggactaaaag aaaacttgta  54180
aacctaagag aacctctatt tttgatatac aaaataatac atttccttaa actatgatct  54240
tgatactaga attttaatta aaaaatacct gcagtttata tgcaaagtta tagattaatg  54300
cttaaaaata ggttgtatgt agtatccaca ggtcatgttt gactgtcaaa tagatgtaat  54360
tttaattcat aataattgtg tcgtgttctt ccccactaga agccaattat gcaagcttca  54420
ccattcacac atggaaaata atttaatgga gtactcattg caatttcact tatccagaat  54480
tggctgttgt tctcagagca gcttgtgttg ccttgttaag gagaatatgt tagtatccag  54540
acatccagaa aggatccttt actgtttcag agtccatttt ccccactttt gaaatacaca  54600
cacaaacacc cattcatgca aaccaaacag agattgtaaa gtgattccac tgacatttat  54660
```

```
gcacttcttt tttctctttg gttcttcaaa ctctcagtca gtgcgcattt actcttaatt  54720
tagatacggt ttaaacctaa ttagaaacca gaagctcttg tatttccaca aaggattatg  54780
acagccccaa gaaaagatag tgaaaccatt atataacaag ataaaggctt cttaacaata  54840
caaggatgga ttttctcatt gatcttagcc ttctgaattt tagaaattgc catttcaaag  54900
tctaaaacaa aggaaaatca gggaataaaa gaatggtaag tagacacaaa cctactggct  54960
ccatcatttc tgttttagca aataacctgc cacatatacc aatagcccaa gagatgggca  55020
tgtccctgca tttcctggtc aaggtgacaa cactgcgtcc tcctggaaga ggtctgccac  55080
tcaccatacc acaaaccaaa tataataaaa tcagaaggca cactatagtg aatttttttag  55140
aggcatgtat tgaaaagcat ctcaaaaagc attctcgaag cttccagaag tcaactcaag  55200
ttatctgaaa agtgacactt ttgatgattg ctcgcttaat actgggagag ccagatgaag  55260
attcctcccc acttcctcag atgtgcaact ctggaatttc ttagtgttac tggagattcc  55320
tgctgcattc tgggccttta atgcataaac actgagatgt tctaaggaaa ttactcccta  55380
gggaggagag gggtggacga ggagtaagct ttgctggtga ctcatgcgct gtgtggaaac  55440
tccctgcaca agtgagctgc gcagggtgag tctaaagggt taatgcactt tcaaaagcct  55500
ctaatttgtt attccagaag agtaatttac tcactagaag tatctgggtg gctactaaca  55560
catttgtgtc tttaaaaaga tcagttttat tttaagatta aaaatataaa gcaagagctg  55620
gaaagtcact aaaaactgac agccagtttc ccattttcaa gagtatttat taaaaggttc  55680
tggttgcaga aggaataaga aatggcttga gatcatgaca cagtgaatca tgttgtaaac  55740
atgttagcta tggctgtgaa ttcaaccagc gatgagttca agcgtcccca gaaggtgttg  55800
ggggaattag ggacatggct gtgtttcccc agagaaaagt ggccatttta ctttccctct  55860
tcactaacat gcttttgaca tgcatggcag agctgaaggc aaggggaagg ggacaacata  55920
gtaagtgact aagtggcttt tttttttttt tttttgccaa gtgaagctga gtcatatggc  55980
ctctgtcatt ccaaaactat tctctacggc tgcattcctt tcgctcttgc cttcctttag  56040
aaccctggag aaggcctcct gaagcctggc cctattatgt atcctgacaa agataaactt  56100
ttccaaaaag ctgcatgttg tttctagcac agtttttcct cgcagtgact acgtgatgaa  56160
agtaccatgc agaggaggtg tctgactgag gcgttcgtgg tgtgtgacag agtcccctgc  56220
acaggacagc cgcactcccc tcttgcgtcc tttcctccca tgtttgcaaa gcctctttcc  56280
ctgtcagcag gggtgttct ggcagttgac atttctgaaa actacagcct acatttttaa  56340
aaaatccagt aagtgaaaac taaaaaatta ataccgtggt cataatagtg tggcatttga  56400
taactaatga ggcactgtcg tgccagctat tattttcaga catttacagt cctttttaa  56460
atacaaagaa atatttggtg tgaaatgttc cccgggagct ggtgcaagca gaggcgacag  56520
ggcaagggag cttgggttgt agcctcgaat tcctccggcc agggctaccg tcagcctgcg  56580
gcacacaagt aaatcaaata taaaaccaaa atttctgtaa gcaaatcagt ttctaactca  56640
ctgtaacgaa ttatctttcg cacatcacag aggcatctct tttcactgtc gagtttggtt  56700
tgcttggtta caaaaagggc agttcaaaag ctttggttgc tattgtgaaa gtcagctgaa  56760
ttccttccac cgtgctgggg tggggtgggg ttcacgcagg ttctcttttg tcaccagggg  56820
tgctgtggat tcacaagtaa gcaagaggct cctcaggtca agcctctggc tgctccctga  56880
ggtcagctgc ctagcttctc ctcctctgag atagacggga acaaagtctt tgatgtgtgc  56940
atttctcaag cttgacaatg atacagctac ataaaaaccc atgatttcat atagatattc  57000
```

caaaacgtaa aagtaaacca tgcatccaca gagacatgga attacagaac tggatgctga 57060
gctggtcact tgggaggcag gcgtccttgc cattggttta tgcctcagcc ccaccatgca 57120
gtggctggcc aggtgaccta ggccagtcct gcatcctcgg ctcctcacct gcctggtggg 57180
acagtgacat ctctcctgca gcactgctgt cagggtgagg gaggtagggc gcagtttcag 57240
aaaaccattg ggctgcacct gcgtgagcac agctgcagga gcaaaagtca gaaaggtcag 57300
caaaggattt caggagcaaa ggtcagaaga aaccctcaag gtggttgtgt ctgcaggaaa 57360
gtgctgtcgt ctcctgcaat gctttcaaga ctattcagaa gcacagtgtg aagggagagc 57420
cggagcccat ggggaaatga ctccagagtg ttccacgtgt tggaaggcat ctgttggaaa 57480
acggacattc aagcaaatag ttgcctgcat agacaacgca gaatgactgg gaaagcccca 57540
acaagttacc tactggtaaa tgaggtgaga agcttaaagt gagaacccca ttgctgcctc 57600
tttttcactt taaaaacatt taagttttga attatggtaa aatacacgta agatttacta 57660
ctgtaaccat ttttaagtgt acggttcagt agtgttaagt atattcacat tgctaaggaa 57720
ccaatctgct acttttgttt attaattttt tcctgagggg aaatattttt aaattttaaa 57780
atatttaatt gacaaataaa aattgtgtat attcaaggtg tagaacatga tttcatatgc 57840
acgtacattg tatactcatt accacaatca aagaaattaa cacatccaac ccacccatag 57900
ttgccattgt gtgtgcgcgg atgtgcgtgt atgtgtgtgt atgtgtgcac gtgtgcgcct 57960
gtgtgtgtct gtgtgtctct gtgtatacgt gtgtgtacat gtgtgtacgt gtgtgttcct 58020
gtgtatgtgt gtctgcgcac gtgtgtatgc atgtatatgg gtatgtgtgt acgtgtgtac 58080
gtgtgtgtgc atgtgtgtat atgtgtgtct gtgggcacag gtgtgcctgt gtgtatgtgt 58140
atatgtgtat gtgtgtacat gtatgtacgc gtgtgcatac gtgtgtgtgt gtgcacaggt 58200
gtgtatgtgt gtgcctgtgt gtgtgtgtgc atgtgtggtg gggacactaa aaatctctca 58260
tcaccttttt agtcaaaaga acagttgttt tggtttggct cttctgtttt aaaatatcag 58320
aacaataata atttcccaca gacaaaatcc tcaatcctca ccatccttct atttcctata 58380
ttcatcataa acttcatgct tgatgttgaa attgttttct gaaaatagag aatacaaaga 58440
ggagatttta aaatgtcagt ggcagcccca cactcctttt taatcttatt tcctgatatc 58500
ttgagtttac ttggacgtag agttttcctt gactatggtt atttctggta gtagcagctc 58560
cagattaggc aatggttttc ttcagagata gcttagagtg agccccagaa caaggtcaat 58620
gcgaagattg cttgtgtctg cgtgtccagg gcacagtgat cctcatcact agccgggggg 58680
ctccgtgagg atctgctcct ggtcgtttct gttctgtatc ttctctgcag cccttactga 58740
agccgttacc aactggcaca attcaattcc tactgtaccc atcatgcaca gatggctgaa 58800
gtattgagaa cgctccagtg accgggaggc aatagtctgt ccacatctaa gaacacactt 58860
ggaataacct tagagaagag agagagagag agaatgcatg gttagtaggt tatcaaactc 58920
ctatgacttt tcacaggaaa agccctcatc cacaccaact ttaggaatgt gtagaaagaa 58980
gggtcaggga caggggtgag tggtgggcag agcagttgga gggcacaggg aaaaggcatc 59040
tggtcatgta tttggagtag gaggtcttgc tttactattg aattgcaggg acactttggg 59100
aacagtgttc acttcttttt gcaaccattt cttcagagaa aagtcatgat actcaagtct 59160
tcttacaaag cagtttgagg ctttgagtac cagactgatt acagagatga gtatgaagca 59220
ttattgtagt atttttaagt gaaattcact aaatgcaaat aaacctagca aatgctctat 59280
ggttaatttt tttctaaaat tcagataatt aagacaattc attctcctga aactgctgtt 59340
catgtaaaaa ggaattttat cgaggtggcc cttgagtgcc aaacagcctg tcctcagctg 59400

```
caaaatgagt cgttgatgat cctccagcaa gggatacttt ttagctcgtg tggtgattgc  59460
tgcacacggg atatgtgcag caagtatctg ctgagctaat aataaacagc ctcagacaga  59520
aagacagtgg gcacaaggtc atgcttaaaa agaccccttg ttctactgca tcccagctcc  59580
ccaccatggg gcctcacagg ccctggtgac caagcacatc agacctggtt cttgctcagt  59640
cctgggagcc acagaaccca gcacgtactt tacccccaag accagactcc agcttggctt  59700
ttgtcctcct ctccaggatt ggtgacctcc taggtcgtga agctgtgatg agcaaagaca  59760
cactcctctc cattctccca acttcaggtc cctttgacag tgtcagcagg catttaaata  59820
gcagaccacc cacagcaggg ctggtagatg cagtgaactc aggaagatgc ctgcatagac  59880
tctagtgtta aagacagaat ccttacaagg aacccccata gttacctaac tgctgtctcc  59940
agtggtcata gaagtgtgat aacccactaa tcatcattct ctgtctctct gtctttctca  60000
tacacactta cacacacata cacacaacct tgttgcttaa ttttcagaga gtctactttc  60060
agaaaagcct tcaggaatac atcatgtaca aaactgagaa attacctgaa gtatctttaa  60120
atttagtaaa aagttgcatt gtttttttgaa catcacactt gaaaagtaca tgaatacaaa  60180
catacttagg aaaaaaagct ttaattaatt taaaaaggag aacaatgcta tatgctgtat  60240
cccacctttc tctgaatgtt acattttctc ccctatccca ggctgcatct aagaaaactc  60300
agagggaata tgctatctat cttttccgag caatgaaagc tctgggtttt ttccttgctt  60360
ttcagggcac aatacttctc tttcttcctg gttagacagg ataagttctg agtcccctgg  60420
tatcatcagc ttacttcttc tctgttaaat attcacaaaa aatcactaac tttcatgcct  60480
cagcaaacct ccactgccta aaatatagtg aggtcattca tcttcggaca aattgcccca  60540
actacggtgg gaaaagaacc aatgtgttgg actatttatc taatttttgt ttagttcggg  60600
gatacaaata aatgcataga tacatacaaa catgcgtaca taatagcagc agcagcctgt  60660
gaaacattga caagacctgg agttggaaga ggactttgcc atcctccagt ccaacagttg  60720
cctgtcacag attagacgac tgggatgtgc gcaggcgatt atttgcaaac ggccctgagt  60780
cccccagttt atgtcttaat tcgcagccag ggctgattgt agaagcaaat ttgcaaacat  60840
gtgcaagaag aaatcacaca tcctagagct tggatttcct cgtttcttgc tatttctatc  60900
cgtagacaga accattgctg agctgttaaa tttgtctcct tcccctatac cagtcttgaa  60960
aaaggaaagg aagtggagca aagaaaaaga aattaataaa gccggcagat cctaggagaa  61020
tcttatttaa tccaagcttt gtaaagtttt gctttattcc atggcaacat gggtatacac  61080
atcccaccgg ctgtttcagt ggctcagagc aggtaaggcc tgtgccaaac gccgctagca  61140
ggaggaacaa cgtggagaca gccccagagg tggaacgttg gcccttctgt ggctccggtg  61200
tctcaggacc tccctaaagc ccagccctga cactgagcaa gtttccacca ctgttaggaa  61260
gaagtagaaa ggaatttgga gggttggtgt tactgttcaa gagctggaag gcttctgccc  61320
ccattcccat tccattaatt gcgtgaggta gagaactcat agaagatagg aacacatatg  61380
ctgatttcca aaattgcctt tgtatatttt cacgtgaaga ctttaggggc aaaagaaaag  61440
aagcaagcat tttgaatatg tgtttcaatt tgccttctgt tatataaaat tgtattttgc  61500
ctattctttt ttcattattc ggaaccttca agaaataaat taagttctct caaaaatgtg  61560
ttttttgaaa agaggactaa aacagatggc ctggctgtgt taaacacagg gaccagacca  61620
gcacccacct ctccacctgc cctgccttca ctggcagaat tgtgatccat catgttctct  61680
gttcaatgtc atcatccctt tcagagcatg ggtctcttcc tttctaggca gtcttaccag  61740
```

```
gatgcatggg tgtgcctgcg taggcacacg cacagctccc aaggactcta aaaaaagata  61800
tttttctgct tatatactaa taatatgtta gagatttatg tttcaaatta gtacagaatc  61860
acatggttct ctccaaatta tatttgagag agaaagaata gaacaaaatt tattttacaa  61920
aaatactcag tacatttagg gcatatacaa agatgttcca gaatgtagct tatctcttta  61980
aagacaatta acacagtttc tgggcaaggc aaggcaaaat attcagtaac ttagcaacac  62040
caacagaaga cagccaatat tgcagcacat ttttctcttg gattgggtca gagagtactg  62100
cagagaaaat ggagtagaga gacctgaaat actttcgcac acactgtggt cagtgcagcg  62160
tccactgtgt gccacagtaa tactagaaac tccctggtta ggccttggaa tccagctctc  62220
atttcgtatg tgacctgcag ggaagtaagt taaatgcaca cgttttatca agttcaaatg  62280
caaacttaat tttaaatgta tgcaacatca gtttaagcgt tgtagctatt actagcaatt  62340
gtacctatta ctagtctgta ctctgcacaa ctttggagta tactgcctac tcaaggtgga  62400
ttttagagct ctatttgtgg cattatatca cggacaaaag cacgttcatc agagtcagag  62460
gaatgtggtg caaatcccag ctgtcccact taccagctgt gggacttgag taagctcctg  62520
aagcagctgc acctgcattt tctggtgggc accatggagc tgtcagcagt gctttcctca  62580
gagggctgcg ggctggatga ggtttgctgg tgcatgtgaa gtgtcaatca ttgctctcat  62640
gagtggtgat gctgatgccg ttcccttttt tagggaagtg attttccctt acaaagttac  62700
caacagtttc atgttggccc atttttctat taattgtttc cactaatagg accaacagtg  62760
gtagtcccat cattttatta ctgcttgtcg tagcacaagc agttgcttca ttgtgtttag  62820
ataaatattg acggctgctt ttaacagtct gctgttttgt ctccttttga ggtccttaaa  62880
gtaatcctta aaaagatagt gcagatggaa agatgtctgg agtcagtgaa cctgccttct  62940
ttcctgtgtg cttgtcagtt tctaaaatgc catacacaaa ggactttcat gatttctttt  63000
taggtacatg attacagttc aattcacttc actgtctgga aaatttcctt ataatcagga  63060
tgaaatttct catgttagcc tttcacattt cactactttt agataaggaa ttctcaggct  63120
ttgctatatc tgactgctct tggaggctga gcttttggct aactacctga ctactttgtc  63180
gtttctcttc ccttggaatg aagcaaatat ctaacttctc actcattgtt tctgctattt  63240
taccatttag tcatctgtga tttttctaaa tactgaaaga cttccctcaa ttcaaactat  63300
gtgccggatc aaggaaaggg cagttggata ttgcagacag catagtgcaa ttgtgaagag  63360
tgtctgctta ccagccacgc tgccttgcac aagttatcaa gcctctcaac ccacttcctc  63420
aatctgtaaa ataggtatga gtgtaggacc ttcccagggg attttttttgt gactatagaa  63480
tgattctcag aagactttca ggcagtatgt gggtgaggca catgctggaa aggcttctgc  63540
aggtgcagtg atcaatgctt ttctcagtgt gtacatccca taatacagac acgttaccag  63600
aaactcccta gccaggactt tgattgcagc tcacattttg tatatggccc atagggaaat  63660
gaagtgtgta ttttttataa agttcaagtg ttaacttaat ttggaattta ctatcaaatc  63720
tcagttgtta tgggcattta tagctattaa tacttcgtcc catgtgtccc atgaggaaac  63780
caaggaacag aaattaaagt tctttctgga gtcccctgaa tctcgttcct gttcttttgc  63840
accctgttaa ttacatagag acattcacag ctcttctgac cttatcagcg ttaaggaaaa  63900
cagaaaacca gcgtgctatt tgttctgtcc cttagtcaag ccttctcaac atatattttt  63960
cttccaagat tttgcatgtg cacagggatg cctatcctct acaagaaaca cattttaggc  64020
aaattataat taaaatgctg tttacatctc ttcaccttta gaatttaaag aatgatcatt  64080
tcttagattg catctcagac acacccttcc cctagtctgg agagggcgag gcccatgggt  64140
```

```
actgcaaaca gcctgacgtt gtcaggggcg gtctcaacgg ctcattcacc acatctgcct  64200
cgcgaaggct aagccatgtg ctgttacccc tgctgcgctc tggctcattc taaggtacac  64260
gctattaacc ttgtgagaaa acaaagaggc cagccccacc cttcctgctc actctgagtc  64320
acggtgaaaa tgtttcagga tctcgggttc gaccatgagt cctgtccagg tccaggagga  64380
aattcggaag gaccacatgt tcactctgag atcccacttt catttccctc ctggttgagc  64440
agcattaata ctctggctag atttaaattc tggctttctc cagttagaac tgaaagttat  64500
gacaatgtaa tcaaaataga atgtgggttt acagctggcc ccctggcctg gtttgtgaac  64560
ataaaacaga aacagaaagt gtaagtggtg acatcatatt ctctcattca atgtgaaagg  64620
ccaccgaagt ctttccagaa ttatttttga gaataatatg aatttttaaa aaatacctaa  64680
ttattttaaa tatcgtcttg cttgctcccc aaatacctac tgttttcaac ttggatatac  64740
gacatgatta aagaatatct aatatttggg aatgcatact ttaaccttat aaactaccac  64800
tgtaaataga cagactcatt aaagtgaaag gacattttaa atcaattagt aagcaaatca  64860
attaggtggc aaagacaaga ttatttttcc ttatggtagt tgaagaataa tgcttaacct  64920
gtcattctaa ttaccaagca cggtgttctc tttggaagat catttcaaca aaacattatt  64980
ttcatccaga atttgaacct tgagattgca tggtatttta gaaatctatt ttagaaatct  65040
ttggcaaagg ttactattaa aacaatcaca ttcatggaaa atcagtataa gagcaactaa  65100
aataactcac aataccagta aaatcacttt gtcatcttct taagactttt aaagagcatt  65160
tgtaagtaac tgaatagaag gccaaagggt gtgtaggtag cccagaccat cagtgggcag  65220
ccagggccag ggcaggggcc acggttgcag cctgcattct tctaaagggc agagcaaatt  65280
aaagttgaag caggagctaa aaaaaaaaaa aaaaatgttt caaagaattc caccaaccag  65340
aggatactac ctaggacagt ttgggcctaa cttatctgtg aaggcctcca gcttcctcca  65400
caccggtggc cacttttcat tcactctgaa cccttctttg tatggaggtc attttattaa  65460
ttgagctgtg accaacatga cagaatttcc tgttttaggg cttttataat atagatagtt  65520
tatatctaat ttcagaatat attcactggg gaatggactt agcaaccact accacaacaa  65580
tgcaacaatg tgttttggaa caaatttacc aatctgaatt tccccctaga ttaggtcaca  65640
ggaacattgc agctgatgta cagctatgtt cctcctgaaa cttggagaca catcctcttg  65700
agctgggtta taatgggcca cccaaagctc gagttcctgt aatggataca ctcaggcagc  65760
agaacctacc accgtagtga ggacagcacc cagagccctc agaggccatc acaagtgcac  65820
cacagctgcc ttctctggca cgctcagagc tacacagtgt actctgggat tggaactctt  65880
tatttttttt tcagttgatt tgtaaataag attgcacaaa aatccatgca catcaactct  65940
ccaaatcaga atttgctgag ctaaaaagag cattaaatta gatgggctgg ctttcaaggg  66000
gtgggggtgc aatagtggaa ctctgcacaa cagttcttta caaagagaca agcaagcaca  66060
tcgcgtggaa atttccattc aactggaaat gtccaagcct gtttacctca attaattgtc  66120
cttgttcact tgtccagcct agcaattgtc cattagtaat ttgttataaa tgagacattt  66180
ggtattaaag catctctttg ggatactggt atggtttatt ataacattct gttagtagtg  66240
ttgtacaagc ttgagatgta ttaatacgaa atccaagctg catgagggct ttatttttca  66300
agcctacacc ttgctgaaat tctgaattaa aatatgattc tcagtacaaa tgaataaatc  66360
aacagaaatg gtaacgcatg tcaaatattc ttaaaaccca agaaagcctt gtaacttcct  66420
tcaatctaat gggaaatgca ggcaaataca agactgatgt ccttgagttt tattatcaag  66480
```

actcaagggc accagtaaaa tctagtttca ttggttggaa aaaaaatcct gataagcact 66540
gttaggcata ttaactttaa tgattacaat ttttaggaca ctctgtggcc tagacttaga 66600
aacacaacta atgtccagaa aaagattcct ctttttattc catcatctga taggcctatt 66660
tttacacata cacaccaacc aaaagtagcc aagcaaacaa aacaacatac tcacacccct 66720
tcgcctatta tcatctaggt gattttcaat gctcattgca atgaaaccta cttattgtgc 66780
atggcaccca cccccactga ggaatactgt agtttctttc cctttgaact tcattagtag 66840
agcacatggt tcattcactc ctgaagagtt cttcgtatgt cagaatatat atactacaac 66900
ataatttcca tcagagctct gaccacccgc ttatctattt tcataatgcc tgccactcca 66960
tcattagctg ttgtcatgta ggctatcaat aaatatatga caaataaaac agttagggaa 67020
tgagggaaat tgactagcag ccaaagacct aagccatcct ctgcttggac attagaaaac 67080
tgagttcact acagtcataa gatacacaaa ggcagaatgt aagccataca aaaatccatg 67140
tcaatcccaa tatgtgagta caactattga acaccatgta ctaatggatg agttggtaaa 67200
tcattcaatg tcttcatgag gtcaattaca gattattatt tagaccccaa agattccaaa 67260
gatggtattt cggtcagatc ttcatccttt gtaagcctag cagaaaatat ggcagtttta 67320
ttgactacta ttctttgctg ggtgtggtat ttttaaactg agacatcagt gtgcctagca 67380
cagggcctca agcacacaga aaaattcctt gataataatt aaataaaatt tcagcaaaaa 67440
atatcatctt aaggctgtga aattatcttc ctgtgtggct aaaatagtga ataaaattca 67500
gcgcaatata aatcatagta caatttcatc actaaatttt ctgatcttga tcttgtcatt 67560
ttacattgga agtaaaaatg tgtcctcctt tttttctctg acagtgaaaa gtgtgtgtgt 67620
gttgtgtgcc cttttgcaca ccctgcctca cacttgctgg tctaattcct tccagcatga 67680
ttatgatata attaaatgac agaaatgttt acttccaagt ggaactaagc cagggtaact 67740
cagggtaggg cagctgcttg caccgaaaga ccaagactgc tagagaacta ggaaacaggc 67800
ggtgcaagaa ctccaggctc tcatggaaga gcgggaggct tctatggggc tgcagaaact 67860
ctttggtgct tggggaaaaa atgggttaaa tgctcttaaa aaagaaacct gggagaggta 67920
gtttccagat gcaggcccgt cttttctttt aaacagaggc agctccgaag agctggacat 67980
tgaaccctga gcaggaactg gaggccgtca gcgcagcttt gtttggcgag cggagctttg 68040
caagggtgta atgctgcacc agggagacgc tatctgcagg gaccggtgac gccgtgggtg 68100
tggaggggga ggcagtggct ggccctcttg gggtaaggta cgcccaggaa cagtttagaa 68160
taacgtgcgc gagtcaaagg gaagaagaag ctcctgcaga ccttctgggc actgtgcagg 68220
gtttgctcct gtccaccgtg ccgtgttcct gtcctggggt atttgggtgt gtggcgtgtg 68280
gggaggggag aaggagcaag gcggcaggga ggggatgagg accaccctgt ccatgggaca 68340
ggccctgggc cccgcacaca ccccaagccc cgcgtcccgc gtcctcactg tcctgggaca 68400
ccccccaccc caccccaccg ccacagccca gagcggtgcc aggaagccgc ctcgacgcag 68460
ccgtatcttg aggctccagc cccatcccca gggtaccacg ccacgtagag acactatttt 68520
tcacttcgtg tttgtcactc ctaaagcatg tgtgctagct gcaccaaccc tgggatgcct 68580
cggtgcatag ggtttatgtg cgtcctcctc cttccctctg agctggtccc ccgtggggaa 68640
ctgctgccca gactgacctg cgtccttccg cacgtgcagg aaaatgtcca cgtgcacttg 68700
tcagggtggg ggccacacgg gcaccaccac tgatcatctg tgggatcgag ttactgccca 68760
tgcagatccc acgtgcaggg cccagtcgct ttggtgagag agtggacgct gtggtgactc 68820
cacggtctgt ggctgtgctc aggaggacag agaggggaca tcctgagatg gtttgggcag 68880

```
cccgcggatc ctgtgcatgt ccccagagcg tccactttct ccatggagca gtggagtggc  68940
gttgctgaga cagaaagttc aggttctcca ctccccatgc agcccccact cccctgtctc  69000
cggccaggca cgcgtctggg gtggagactc ccggtgcccg gggccctcca gacctctttc  69060
cccaccccag ggagcaggcg ggtacttcta ttccgtttgg cttcagaagg gaaaagagaa  69120
cgtaagttca gggagttctc gtccattcct ctcccgtggg ccgggcaggc agcagggaca  69180
gccttcagga gccaggaggg gctcgagctg cgaggccctg gaatgaggca ggcatgggct  69240
gaggctggag ggaaagcccc gctaaggctg ggcgggggcg ggaaaactta ccaccagggg  69300
actcgagatg gggaaggaaa ggtcagaaga ggagaggcca ggcacggggt gtgggcggcc  69360
tgcagagctg gagcaggtgc tccgcccaga gccaggcatg cacactcaga gtaggtggcc  69420
tgtgcagcgg ggaagagggg cgggtcggcg tgctgctgaa gatgcaggag ctgcggcctg  69480
ctctgtgcgt gctgaaggtg tggtgagaag cacttacaaa aagaaatgga ctgtgttagg  69540
attgcacatt ttactttgtt tctcccaaat acgtgttctt tgaatttttt tccttccagg  69600
gccaggactg gagtgatggt tgagacaggc acgcactggg tcttgtctgc atttacattt  69660
tgagattttg ttcagcatgg attttatggc gtttttttgt ttgtttgttt gttcgttttc  69720
aaaatactgc acggtttatc gtgaagacag ggtcctttgc tgccgtctta agttttgggc  69780
ccaagaacgt gccccaccct aggcccgggc ctgctggctt catagctctc atcattccca  69840
cggaacctta agacctgagg acagaaagga aggaaacaag cccagtagtc cgtgaaaatc  69900
cagggtcccg ccactccagg tgtctgcagc agagctgaac acacgtaggc tcttgccagg  69960
aggggcattt gtatgtgctg agcattcctt atattctcaa tatgacgcct ttgaaagatc  70020
tgtggtttgc aaatatttac tctcagtcca taacttatct ttccaacctc ttaccaggct  70080
cttttgctga ataaaagttt taaattttga agtctaatat atttttaatt tttttatttt  70140
atggatcata ctttttgtgt caggtttgag aagtctgcac caaagtatgt cctgtggttt  70200
tcccttaggt catcttcaac aagtttcata gtattttgtt tagatgtaaa tctgtggccc  70260
attttgagtt agtttttgca caagagttga ggtcaaggtt ctttttttgc ctgtgatgtt  70320
cagtggctct ggcaccattt gttgaaaaca tgatagccaa tgtcaagact taatagttat  70380
aataatcagg agcttttgtt tctttttgtt ttgtttttag taactgccag tcactgcttg  70440
tggtatacat acacaatgga atactattca gtcttaaaaa aaaaaaaaga aggaaatcct  70500
gtcatttgca tacctggagg acattatgtt aagtgaaata agccaggcac caaaagaaaa  70560
acattgcatg atctcactcc ttcatggaat ctaaaaaatt gtattcagag aagcagagag  70620
tggaatggtg gttaccaggg gctgggaagg tgtgagcttg gggagatttg gtgaaaggac  70680
atagaatctc agttagacag gaggaataag ttaaagagat ctattgcaca tcatggtaac  70740
tgtagttagt gacaatgtat tgtatacatg aaaattgcta agagagtaga ttttaagtgt  70800
tctcaccaca ccaaaaaaag gtatgtgcag taatacagtc attaattagc ttgatgtagc  70860
cattccacaa tggatacata tatcaaaaca tcatgttgta taccataaat atatactgtc  70920
tctttatgta aatttaaaaa taagataaaa taaatgttat tcacttgtcg tggatgtggt  70980
ggggacaggt gtgggatagc cctccctgta caactaggac ccaggggtga tctagtgaca  71040
ctagccattt atcaggacgt atgggtgcca gtcaggatga taaagcttcc ttttggccac  71100
tatactactt agaaatgccc tgcaaaaggt gcacatcaaa gattgaaagc tcaatcctgg  71160
attttaagtg cttcaaaagt gcacttaatt gccacatttt tgtcaaacat tttcccaggt  71220
```

```
agtatttttc ctcatgtaaa acaacagcaa tttaatttga acagaaagca ttttgaaaca  71280
tacttttggc agggttcctt gcagatcaga atggaaatga ttaacagggc aattatcaat  71340
catggacttt tggcggcaga aggaactgta ttgtttggta cagtctgggc cagggccaca  71400
caccgtaacg gagatactct attctgtgga cggttggagg gggctgtgct gagcagggta  71460
actgcatctt ttcctagact gttcacactg ctgccacgaa ggagtcttgt ttagactgga  71520
cctggctttc ttcttcgcaa tgagtgttgc agactcccga caaaggccag gtggtaaagt  71580
gtggtgtctg tgagcgagag cctgagatgc ctgagctgac ctgtcctcag ccacctgcca  71640
tcgtgcagag gtgagagcag cccctgaatt ctgcccctcg gtctctccat agctaaagca  71700
aaaccatcct tccgtgctcc caggacaagc aggctattac caaatcaccc actaaccctg  71760
ggcgaggagg ggccatcact gcacaattca tcagtgtctg tgacaggaag agattgtttt  71820
agactggttt tttttttttt atttgcaagc tttttttctct ctccaaaacg tgctgtcagt  71880
gtgttctaat ttactctgta aggaattctg gagctaatca taggctcaca aaaagcagca  71940
caggaaagtt tcccagataa catctatttc agtggctttc aaacattttt gaccttacca  72000
aagtaagaaa tacattttaa tatcatggca cacatacagc tgtatctaaa ctttcataat  72060
actgccttta cgatatcact ctgatattgt ctattctttt ctgtttattt ttctttttgt  72120
tccttgttat gctggttgtg acccactcca gtgatttcac aatgcaggct gggtggtgtc  72180
ccacagtttg aaatcccaat ctagggcctt cctctcactg tacaaagtag gtaactgggg  72240
acattagtgg atcagtgatc aaaccaaagt tatttgatct taccaagtga tatcaggatg  72300
agaaagctgt tagagtgtca gatatgtgaa ggaacttggg tcattcctga tacctcaaag  72360
agaaaaaagg tagtccttga acacctccta cttgtaaagg atgcacaatc ctacatgccc  72420
ctccctttcc tttcctcccc tctgtacccc acccctgccc acattttctt cataagcagc  72480
tttggtgttt tggcttgttt gtttcccttg tctcctacct gtgactttat agccttttgg  72540
agactcacag caatagttgt atttaaactc agtgggtggc atccaaggct aaaaaggaga  72600
ttgcctagac acaaaaccac ccaagggaga aagcaggaca gcatcttact atgattgttt  72660
cttgtttctt cctgtctcat aaggattatt acccagggtt ttcatttttt tcatttcatg  72720
gttcattttc gctccagtgt agacatacaa tagaccactc gtccctgtgg ctccgggcag  72780
cagcctcatc tgagaccctc ctgagacatc tcgtgcaggg cagccgtagt gtgtggcttc  72840
cccagggctg ctctaacaga tcaccatcct tgccatggct taagaagctg cagatttatt  72900
tgcttacagc tctggaagcc agaagtccaa aatcaaggtg tcagtagagt ctctctctct  72960
gaaacctgct gaggatgatg cccctggcct ctccccagcc tctggtgttc ccagcagccc  73020
ttggcattcc ttgccttgta gatgcaaaac tccgatctcc acctctatcc tcacagtgag  73080
ttctcctgca tgtctgtctc tgtgccttca cattcctctc tgtgtgtctg tgtttccatc  73140
tccttatgag gacacccatc actgaatcag ggcccactct ataccagtaa gacctcattt  73200
caactccatt acatcttcaa aaaccccatt ctcaaataag gttacttcac aagtgctgga  73260
ggttaggact tgaacatacc ttattgaaca atccaactga tgacacatag taatttatgc  73320
actcgttctt ggagacgttg actttattta gtagcattaa ccatggcaat gtcaccagca  73380
tcgctgacag cctgaagcat atgatctcca gaatgtattt caatcatcat gttcacttcc  73440
ttggtattct ttagacaata actcagcctt gaactccagt aaagggtttc cctgggattt  73500
tcttcttgac tcactccact gtggcctccc tcatccagga ctgtaacaga cgcctgacgt  73560
cagtggtcta gacctctctg ctgaatgtca tctttggtga atgtcttatg agaaaacaca  73620
```

tggttggtca ctcttagaag ggcatgaaag cctgtctgca gtataaccaa aacaggcaca 73680
tggcgaggca cactgtgcgc atgtgtgtac aattaatatc atggttttaa attattttca 73740
ggccaagggg agatctttgc tgcatctact gaagaaagcg aatctttttc ttcctgaaaa 73800
aaaatggcta cttattagtc gaatttgtgt tttaaaaata tgtgaactaa tataatgcag 73860
acatgcatta atgtttaaat atactggaag tttttggtaa aatgaaaccc attgtctctg 73920
ttgattactt tgatgagtca agaagtaaca tcctgggaat gattggccag tttaaatgag 73980
tgcctcaggt ttttggaata caagaaatca agaggaaggg attagaacat ataggttagc 74040
aagattggga tcctaaaata cagacccaaa tgaatggaac aaaatcaggg aatttattaa 74100
taacagggtc aaggccaaat cagtaacaaa tatcctgagt ggaagaaagg tggtttaaca 74160
aatgccccta tgaaagatag agattggctt accatgatga gatgtaagcc caagttatga 74220
ggttggcaca caaaaccaca aatgtcatag cttaaaacaa cacacacttc ttatctctgt 74280
ttctgtgggt cagggtctgg gttctcaggg actcacaaag tatgttttca tctggagctc 74340
caggtcctct tccaggctca taagggttct tggcagaatt cagtttcttg aggctgtagg 74400
actgaggtcc tggctcctag aggccaccct ctccataagc agttcttagc atggccgcct 74460
gcttctccag gcccagtggg aaagcatgtg cctccaggag ggctcagtcc attcttcatg 74520
gcttttacct ggttaagtca ggcccactca ggataacttc attttgtatt aaatcaaaac 74580
cagctgattt gggatgttaa ttacatctgc acaacttcaa ctttgccata taacctaacc 74640
atgggactga tatttatcat gcatttgggt caagttgcat taagagatat aataaagctg 74700
gacaagcttc tgttgattag aagagttcag ttacaaggct acacttggga ggaatgttta 74760
caaactggaa tggtcagagg atggggaaga cacttgagaa aagtcaagtg acggatgaag 74820
gcaaatgtgg atatttatct gggagaaaac taagaggagt tataatagct gtcttcaaat 74880
atttaaaggg cttttattag gaagaggaat ttggcatatt ggattttgcc ttcagagaag 74940
tggagtcctg agatgctctt agccattcat tccagcctcc agggctcacc tgctgtcttc 75000
tgtccaggtt ctcggtagca gggcagtaca gccccatccg tgatcttcca tagtcaggca 75060
tattgtcaca ctcagtgagc ggagagtcaa ccgggaggaa ggcacagttt ctctggaatg 75120
acctacggaa tggtacgctc aaatgcaaat tctccttccc ttccccagtc cttgtccttc 75180
agatggtaat ttaggagctg aaggtcaggg caccagcagc ctttggaagc ctacaggaca 75240
acagtcagcc tggctagaaa aaaaaacaat gtcacaggca tgttgtgttt aatcacatga 75300
aggatatttg cattgttttc caactgatgc cagcagacac attgtcagtg gtatcatgcc 75360
tggggtatca gagttgacat tgggttgccc cttctctgag gcattcatgt aaatcctttt 75420
aagtttataa aacctccatg tggctcctgc atgcttcatc atttgcatgt gtctcttttt 75480
ccaggggagg cagcatgggg agcaggatgc tggtgggctc caggtgcaga gagcagggtg 75540
ggcgtcagac cccaggtcca ctgtgcacgc cctcttgtag agcccgttcc gttgtccatg 75600
agatgaggag tgttcttatc tctaaagtat tatcatgaaa acctaacaat gtagaaagac 75660
taaagcacat gggtggtgct tcataaatag tatttctccc actttctgaa aactcctgct 75720
gaagtaactg cacaagaatc cttgaacatt tagaattctg gttttagcca taccataaag 75780
tcagtagtgc gtggtggaat tctgctaacg aaaattgcga aggatcaagg cagagtacag 75840
agctggtgtg tagcgggtac cttctgtctg ctggcactag gtattttaca cattaaatca 75900
gctcgttctc acatcagctc ttttaaaaat aaggaaatga ggagccacag tggcccaact 75960

```
gatgcagtgg cagaagtaga atttgagctt gtgcagatgt gcctccgtgt tttgtctcct  76020
gagcatgctg ccccaagttt gacaatacca agatttgtac tggaacattc cctcccatcc  76080
ccaccccccta gaagcccctc ttcctccctt agatttgaca catagtttga aaccactatt  76140
aactaccttta tgagagccac tgtttgtgaa gtgctgacta tgtgccaggt cccgtgccgt  76200
gcaatttttg tgaattatct cgtgtctaca gtgcctcaca atttctctgc tcaatacctc  76260
catgttactg ccgaggaaag ggaagctcag agagagtaag taatttgctc gagttaaaga  76320
gctggccagg acagccaggg gcttgcaccc cggagccttc atccactaca ctgtcagctg  76380
gtatctcaac cagccattac aggctgtaaa aaaattatat aagatagtct atggtaatgc  76440
agaaaagtga ggttattttg ctccctttcc ctttgaagaa aaaagccctg gaaagacata  76500
tcacttgagt atgggaaaaa atgaagctgt ggcttttctg tgagtcaatt ctttcctggc  76560
agcttcttgg aataagacca agtatagcag cagagttttc tgttttaatt tgagctgcag  76620
ggtgactttt tttcttctat gctttcatct ctctgtggct tcttttgcct cgttaatttc  76680
atgccctgcc caggcgggct actgtgctgc ccagtcaccc gggtctgggg cggccaccgc  76740
tggccagcag gcaggccctc cagaggcaga ggtggccacg cttaggtcgc tcccgctgtg  76800
gaggcggcac acttgggtgg cagcacagct gtgatgtggc ggcagctggc agccccatgg  76860
gaaagatgtg tgaagtgtgg ggtttgacga cccatgggag aacagacttt cttcctcttc  76920
ttgttttccc ttcaaagccg tgagtcaacc tcaaattctc tgtctttttt ctccaccccc  76980
tcgtgcctct ctccctcacg ctctgcatct ctcattgcaa gcttgcattt ttttgcacac  77040
aacactatct taatatttct cttttctgca ggcaggaaat gagaagtcat ttttcagggt  77100
cattcaggaa gtcatccaga gttataatgg cccattatct actggtcaga gtttacttag  77160
gctttcacta cttccactgc ccacttgaaa cagggaaaaa tattttcccc ccgcgctgtg  77220
agtgtgctat ttagagctga ccacaagcgg ggggaagaga ggatggctcg gatgctgcat  77280
ttccactgag aacacaaggc tggcaaagct tgtctgctgc ccagcaagca cttcaggctc  77340
acaccatttt aggttcactt taagtagttt ctcaattgtt aaaaaaaaaa caaaaaaaaa  77400
aaaacctgta ctctgaggat atgcttataa tcccatagct aacccagaat ttcttagaga  77460
actgatcaac atcagcagtg gcacttactg aaaatgcaca ttctcaggcc ctgcgtaggg  77520
cctactgagt tagaatatta gagagcaggt ctcagaaaca ttctatccgg cagtcttatt  77580
ctatgcaccc gaagggataa gagccatgct ttcatgaaac atgggttgtg tgtaaaatgt  77640
ttaaaaggta tggcaaaatg tgtttgattg gcaccaagga tttctggttc ctcctagaat  77700
cattaatcaa actttgaagg agaaataaga gagtcggcat tttcttgcac attctttgtg  77760
atgttgtgat gagttggaaa cttcccgatt gggtttatta gagcatgaac acccaggcac  77820
ccagcttcta gccagccctg tcaggcagag tctcctcgaa gatgtggaaa ggactgacca  77880
acagctgagg cctacaggaa cctgagcagg caaggggaga ggcaccccgg aaccaggagc  77940
aatggccttc ccaccctccc tcgtcctctc ctcttctcct tttggagttg caggccacag  78000
aaaggaagtg acatgagtca ctttgggcct tcttaattcc ttcatcaaag gcagcacagg  78060
tgtgtatgtg tgttggtggc taattgaggt aggcccacag aggagataac agatggacat  78120
actatttcct ttcttccatt ctgatataat tcagggtata aacacacaca cacacacaca  78180
cacacattct cacttctttg gcatctacca cacctgcccc agtgcccatt tctctcccac  78240
ctgaataaaa agcccccaca aagcctgagg tacatggaaa ggagcagtgg tctggctccc  78300
aggagtgtga gaagcagcca tgttttcaga ggctgtattc cacttggact tggccctacg  78360
```

```
ctgaaggtag gagcggatgg gggaggcccc cttcgcacaa agagccccat gaaagagtgc  78420
acagtccagt ctataaaaca gacgcagaaa atgtgtgtag gacttcttcc tgaaaaagag  78480
cgtggtgcgt ccagtacctc catgttcatg gaacttccca gtctgcagtt taccttttg  78540
tgcaactccc ttttggtaaa gccctggtca cacttctggt tgttcagatt atacagggat  78600
aattccagag tgattttaaa gtcaactgcc aggcatccgc acttgcaaat tagatgcctg  78660
gcacatgctt gtgttaaggt aataattcat tacaatacaa attacagggg agttcctctg  78720
ggcatgcgac ctttcccgtc atttggcttt ccctgtgatt atcaggggag cttccatcgt  78780
gctgctaatg ggaccttaac catgtgtcaa cccatggctg taatgctgac actgttttct  78840
ttctggaatg aaaggccttc gcaattgaaa ccaaaatgtt atccaactca gtcctgtccc  78900
tttgacgatg aaaacatcaa gttctggaga ctggccatcc agcctccctg cctcatctcc  78960
cacgccctcc atcatttttt gtctctactt acttatttat ttggctgtat tttacgtaca  79020
tcatgcaaaa atattcctct ttgtaaaaag tataatgatt tcaggaaatt agagggtaaa  79080
aagcaagaac catgctttca ctccactgtc aagagttgtg gaagaatcct tccagcattt  79140
tttctgtgta ttttacatac atacaaatat atgtacaaat aaaggtcgat catttaggtt  79200
ttgtttatat ttttgtatat atgagcttat gtcattcata catattgttt tgcctcttgc  79260
tttttttaa cttaatttta ctttgcttga gagcttttg aactgaagta cgtgtaagtc  79320
agcctatgca tgtaatggct ccctcatctt ctgtgaggct gtcactaaaa aggggattta  79380
gcttgttctg ggctttgcag cccgtacact gggcactgtt catacgtact tctctgtgca  79440
cgcaaaggag ggcttgctag ggaggcctgg cagagggtgc cattcaaata ggattttcaa  79500
tggaggaatt tttaaatttt cagttatttg aataagtttt aatatatatc cagaacccca  79560
aatcatcaag tttgttttct tccacatctg tccttccatt tctgaactat tttaaggcca  79620
gtcatgtctc atccaagaaa tcccatcctt tcacacaaca ctatctccgt ttcatggtta  79680
tgaatctcta aaagcatgat ttttaaaaca taatcacaat gctgtcatcg aacttaaaaa  79740
ttagccataa atctcttatg ttacccaaca accagcctac tgacacatct ccagttgtct  79800
caaaaatgtg ttttccattg tggtttgtct gaaacatgat ccaaaagtca gacccacctc  79860
tcacctttcc ctaacctgcc ggagcccatg tttctttcca gccaggcttg gagaccacca  79920
cacgggattt gcttcttggg gcctccctct aaccagctat gcaggatgcc ctctttcctg  79980
tcaatacaag ctgctcaaag gactcattca gttcaaattc acctatgtga gcctaggtga  80040
tgctacttat ttatttattt atttatttat ttatttattt atttatttat tttgagatgg  80100
agtctcactc tgttgcccag gctggagttc agtggcataa tctgggctca ctgcaagctc  80160
tgcctcccgg gttcaagtga ttctcctgcc tcagcctcct cagtagctga gattacaggc  80220
acgtgccacc acgcccagct aatttttata gttttagtag agacagggtt tcaccatgtt  80280
ggtcaggttg gtctcaaact cctgacctcg tgatccaccc acctcggctt cccaaagtgc  80340
ttcatgtttt caggagctgt acgtgcattt ttagttttga tgaccaggtc ctttttctgt  80400
tttttaaaga acttcaaatg atctccaggg tacacagcgc ttgtgtgctg atgaaaaagc  80460
tggcagtaca aaggccacca gccaaggtca cacagccaaa aagcccctga cctcgggccc  80520
cttcccagac cctgggtctt ttgctgccac atgaatcttc ttcaaggtcc tatgtgtaga  80580
ttttcttgac ttggccatat tatttaggat tcagatataa taacaaaata gatgttaaag  80640
cataacatga aggcatttaa aagggtagaa agcacatgat ttactaaaac cataaatctt  80700
```

```
atgacctgaa agtttcacct aatctcttaa aaaataccgt actaaaccct gattgaaaat  80760
cagagctcag acatacagcc tgagatgcca aaaaatggcc aggcttgtct gttgagaaag  80820
ccatatgtaa ctaactgttt ggaaattcaa aatatatctt atcattttaa aaacatcttt  80880
cttctaaaga caatcatctt ggcttcagga atgaggctag taaaaagtga aatactccta  80940
cttgtggaag aaatcctcat tttaaccatg aagaactgaa aaatgcattc tgatgttgat  81000
ggacccaacc tatatttggg tattttatga tgtacacaat atacttttgt atatgagatt  81060
gttattaaat gtgactttgc tttttcaaga catacaatgt tcctccgggg gtcaggcact  81120
gtgtttagca ctttgtcctg acctcatctg acttctcagc tgtccctgag aggtaccagt  81180
gtgcaagatc gctgagttgg caagtgatag tgacaatatt ttcaccccaa tttctaattt  81240
aaagaccccg atttctagtt ttgttttgta ttggatttgc acaatttcac gttctgaaag  81300
aggatgccct caactttgca aaatgggcct tttgaatgaa aaggatcagt catgtcagga  81360
aaagcgctac aatgatgaaa tatgataaat aagtcagtct ttcatctgta attatctact  81420
atggggtaaa aagtgatgaa aactaccatc ttgaaaggtt ctggtgatag tggttcctaa  81480
tgcagtgaaa gatgtgtaag tcaaagattt gtaaccagcc agggaatgag aggcgaagcc  81540
atagctggtg gcgggggcca catctgggtg tggggaggcc acagttgggt tgggggtggg  81600
gcctgcagtt atccacaccc ctcccacctc ccttcgacag tacaggcttc ctggttacct  81660
tccagagagt aaggccaggg agagttgaat aagttgagaa atgtcatgtc gaagctattg  81720
gtggaaagag ttccattaat tgacaataca agtccctact acattctaaa atctggtcct  81780
gactagtggc aagccgggcc caggagtagc acttaaacaa tggcaggctt gtgttgctgg  81840
caggatactt cagcctcaga ggagctgtgt gcagctgggg agactcacac tcagaggatt  81900
tcaaagcaga gggcatctcg tagagcaact tatccaaacc ctgacccact gtaaacacac  81960
acacacacac acacacacac acacacacac acacacaccc tgagagagag aaagagagag  82020
agataactaa agagagagaa ctaaagtttg gcaaaaataat acatgctcta atgaaggttt  82080
attaatgatt aatctactcc tagcatttcc tagtccactc tatctcctta aaaaaaaatt  82140
ctggttgcag cccactaact tgattgtaca gctgcttaat ggatagcagg ctgtaatttt  82200
cagagaactg tttaatgcgg gctacctctg ttcttccatg ctgcttgtgg ttcctgctct  82260
gctcaggaca gaatggggag gaaaacaggc tctgcggcac aatattggca agtgaaattt  82320
tgtaaaccgg ccctcccttc cttttgcatt tggtctgaaa attcaattag atgctgagtc  82380
ctacaatgta tttgagaagc ccaggagtgc cctagaggat gagactgggt ggctccctgt  82440
caggttgaac atttgcctta attactttgg caagatttgc atcagtggta ttagtccctg  82500
cctcacttgg aggcctgcac ttaagtggcc acattcaggc tccaatttcc tggtgatttc  82560
atagtgtagg gcacttgcaa tcaaaactag gcttaaagcc caaccctctt acattttacc  82620
cacccccaca aatgcagcaa ataaaatgac tctgattttc attccctaga cctcttttct  82680
atatttatta cattattgtt aagacagttt ttgaagaaag ctgttttatt taacaaaata  82740
gctttatgga atcaacttca tatatcttct ccgccagatc aaaacaagct cgtagtatta  82800
gatgtcaccg agcaccatga caggcagatg aacatcatcc ctgtgcccgg ctaatgatag  82860
ctcggcctgc cccggcgtca gccgctcctg gcagggccag cgggcggtgt gggaccggca  82920
ccgtatctcc agcaattcgc agataacaaa tatggttctg atgatgttac taaagatctg  82980
tccctttcaa gattggatta gacattagga atttggaggg ctttttattg ctagcatttt  83040
taagaataac caattagagt attgattcta aagtctgaaa gccacatgga cagagttcat  83100
```

```
gtaattggct actttatgtg cctcttccta gattgccctg cattttcaaa acaagagcct  83160
ttctatttta atcaaaagaa tccagaatga aatgaggctt tgaaaactca gcctatgttt  83220
gtcttgattt ccttaactga catctagaag aaaatatgag ctcaggggtc cgctgggttc  83280
cttccagcgc ctaagcctgt aagctcttcc tgctggaacc aagctttaaa tgcacttgtc  83340
agtcatgtcc catgagaata gatactgcct tccatgtttt tttgttctga tttccgtgtt  83400
tgaaatgatg aaaatcattt ttctgtgctt tttaaaaatg gaattgcttt tgtgttggga  83460
attgtgctgt tcatttttac tctacctcgt tttggaatca ctaatgtggc caatttatag  83520
ccaaaaatca gtatcgtaga gtgagcaatg aatggcatgg tgactgtgtg agcgaattca  83580
tgccctccct ccccaccgct cgccccgcgt ctcagtcctc agtgatggta aacagaatga  83640
ggaccttctc ccgaccgtga tgcgcctcag ccctacttcc cttgtccttt cctatcataa  83700
aatcttcttt catagaaatg gtcatttctg ttcatatctg tggactgtaa ataacaagga  83760
agtcattttt gaggtgaaaa ctgcacttag actcattcca attttgatgg aaacttttag  83820
ctggtggatg gcattttgtt ttgtcttagt tttgcaagga gttatcttaa tttagggaga  83880
tgaaactagt ctgtgatccg aggtctcact tccatacatt tctctcgggc agtgtggctg  83940
cctgaatcat gcctggatgc cacaggtgct tagccagctg gtcctgtcgt aactgtcact  84000
ggtagctcag ggagtgcaga ggtgccagca gacactatga aattggcctc gtaaagcatc  84060
agttatgttg tgatggtggc aaagctgcag gcgagatggg aagtgcagcc actgagaact  84120
cacagtagag cgtgtgtaac gtaaaaagat gaaacccatt gtacacagct gtgtactgcc  84180
tccttgaagt caaatttccc ccattaccaa ggaaaagttt tttctgaagg gggctgcttg  84240
acaggatgac atctggtgat atcatttatt cctttggaaa tcaatctgtg gaagtgagtt  84300
tccactgact gatgaggaga aaaatgaatt ggcttcaccc agcatccagc ttcttatcct  84360
gggagagata gctcttggtc tgtcatccac gcagctgcct ggtgcaagag ccaagtttgt  84420
gcagcctgca gagcactctt cctgagctgt gggctgccag gtcgggggc aggggggcc  84480
tcactgtgca gcctcctgcc acccactgat catctgggga gactggccta tcctgtcagg  84540
agacgcagtt gcccagacgt tttcaagggc ctaagatgta ggcagttgat ccacagattt  84600
ttggagagtc cttgagttgg agattacagg tgacctcaga ggagggagtg agaacatctg  84660
ggtcatgggt ttctactagg agtccacagt gaaaacaaga agaggaattt acgacaagac  84720
agtccagcaa cttcctttct aacttctcct ttcacatatg ctggatactc caagactttg  84780
catttacatg gacatcacag atccactttg agagaagtag ggtaaaaaga aataaataca  84840
tagtgcttta ggtgtatttc tatacatctt aattgatatg ggattacatt ttcacttgtg  84900
tttactgtac agactctaga cagatcctgc tcttttgcag gtaaaacaaa tatttcttaa  84960
aacctagaaa gacccaaaac aatttaacag aaacattttg gaccattttg gaccttggca  85020
gttaggcccc agtgcagcag cggcaaccat aaacctctcc ataggtgctg aacccaggtg  85080
atccctggca ccggcagcct tatgtcaggg ctctcttatc gctggttttt atttctccta  85140
ataaaagtga ttaaaagatt catcttttaa agaaagcaag gacacagagg tggattctcc  85200
ctgacgctag cacagctcat gcccaagcca ctcctgcagg gctctggtct aagtgcaaaa  85260
gctggaaaag ctgcaggtcc cgcaagacac agagcaaccc tgcaagccag gtcaccttcc  85320
ctcttctctg ctgtccgact ggccctccac catgtgacat tcaaaagctc aagttactta  85380
acctctcaaa actcagcatc cttttctgta cagtggggaa gatactggac tgttgtgagg  85440
```

```
attaagtgag gagagtggcc caatgaggtt gacagttatt actgtcattg tcattatttg  85500
ccttctcaca ggcaggcgtg ccacagtcat tttactgaag ctgcttcagt gggtcctgaa  85560
ttaggccctg tcctttggga gagacagtcc tggttcaaca cacagctccc tgcccagggc  85620
agcttgggag tgtgggccag tttcgccttt agaaccacaa ttctctgata tgtgcaatga  85680
gagaattaat tatagactca aaggattgca tgcagacaca cacagataca aacacataca  85740
cacaacacac agagttacac acagacatgc tcacaataca cagaaataca cacagacaca  85800
cgcacacagc acacagagat acacacagac acacacacac acacacacag acatacgcac  85860
agatgggcac acacagagac acactcacag agacacacag atacacacag gcacacacac  85920
agagagacat acacacagcc cacagggata cacacagaca cacagagaca tacctacaac  85980
acacagagat acacacagtc acacacagag agacatacat acaatacaca gagatacaca  86040
cagagacaca gatacagaca cagacagaca tacacacaga cacgggcaca cacagagaca  86100
cacagacaca cacaggcaca cacgtgcaga taaggtaata ttagctagtt caggaggaga  86160
aagagataaa gataaagtaa tattagctag ttcaggagga gtgaaagaag ccttgttttt  86220
ctccactttt tatagaagag aaagtgaaga ttcgatttga ggtgagttca gcacaaaagc  86280
gtatcccagg ccctctggct ccaactgcag ccctttctac ctcattccca gaccccacct  86340
aagccttttc tcttcaaaat cttctcaggc acactgatac acatacctca gatttttaat  86400
tctccggttg tgttcaccag gtgcttggtc atgattaaga attccgtgat gtgtacccca  86460
tgtgtttaaa tttgctgctg agttaacttt gtggcggcct gtggactaga cctctgcaca  86520
tgcaatgcag aacggcaggg ccagatttga aatcctgcta tcttttcggc tgccttgtaa  86580
aaataacatc aggcgatggg gatacgatgc cagaggtcac ctgtgataag ttctgtttat  86640
ggccatttta cttctaggaa gacaggaagt gtcaggatct cagggatcta ggaagccaaa  86700
atgtttttcc actctgaaat aaagtgactg accaggagtt cccggccacg cagccctgtg  86760
ggaactgccg cacggccact tttatgaagt ggacacgtgt tggtcccact gaaaagaaac  86820
tccccaccca tggctccctc acgctgcagc agaggccctg ccacagcacc tgtcagcccc  86880
tgccagcttg caggggcgca ggcgcagagc ggtttgtgcc cttgctggag ccagggaagg  86940
gcacagggtc cctcctggag tcatgggagg tgcagccgag gttctatatt aaaatacaga  87000
ggctagcaca tgtgcttggg gaatgcagct acagtagtgg aatgaaagtg ctgtccgttc  87060
cttacccccc cagctcctca cctgtcctcc acacgcatat ccctggctcc ctttccctag  87120
taaggagact gaattgaaat tgtggcttgc ccgaggctgc atacctgtgc tctttctgaa  87180
gcccaagtca ctggctctag aattctaacc tgtgaggaag ccactgagga tgtttgtcaa  87240
aatacatatt tctgtgcctt gccccagttc cacggcccag gaatctgcag ttttcacaag  87300
cacccccagg tgattctggt ggtgtctttg cacttcttca aggcagtact gcctggaacg  87360
cagaatccca gcctcctcta tcctccttgc ctaatggcct ggatgctctc agatctacag  87420
gggaagggaa ggtcacacag tcatcgcaat agtaacctca gctgataaat cctcccccat  87480
aaaacttatt ccccagtgtt ttttaatagg aaacaataaa actgtaacca gcccaaatat  87540
ccatcaaaga gaaaatggag aagtaaatca tcgcacattc acctggacca gatctattgt  87600
aaagccaata atactgaagc cccttccaag gccctgggag tcctaacagt gcactggcag  87660
tgtctataat ttatattatg aaatttgcat aaggaaaaca ttttgtctca tttgtgcaat  87720
ttctccttct aaatatacgt gtcactttgt acctgatttc tataagaccc aggacctaca  87780
aaccctgtgt ctgcccctgc agccacccag ggaaggactg cacagcagca agacagattg  87840
```

```
ccatggagca tgttgtgccc aactagggac agcgcagata gattctgtaa tttgcctaac  87900
aatgtctata ggatgatccc atttgtcaaa aaaaaaaaag aactgggctt tattgatgtc  87960
acctaaatgc acctaaactt ctttttgcc ccatgctctt ctgtactctt gatctttccc  88020
caaattttta aaaacatgac actcattccc ttatttttcc tacttagaaa agtgtagatg  88080
gttttatcat aggaagttca aaaaaattaa aatataatga aaaatactca aatagtgcct  88140
cacaacagta actactgcta acataaataa aatccatatt tcctctcata cagaccccag  88200
agttgctttg cctgacagtg tagttgatgg agaaaataat ctttatcctt agcctccatc  88260
tggttgcaga ccataaagac agggaaaaaa tgagggtgtt ggtagcttcg ttagaaactg  88320
aaagctcact gattttttca aaacctaaat agcctgtgtt tctccaaata actaatttgc  88380
agccttcggc agccaggact ggcagggatg gggctagggg gactggggag aactgctctc  88440
tcctgagggt ggtctgaccc gacagcacgc atgaccttcc cacagtcagg aactgctcag  88500
agacgtgatg gcaactccat agaatgaaat actcttcagc cagtaaaatg tatttttgga  88560
taaatatttg ctttaaaaaa ctttactata tgttgttaaa tgaaaaaaaa accttaaggc  88620
atcagaaatt atgtgcagta aaatctcact tttgtaaata aatatacctg tttactacgt  88680
atgcataaaa agaatcctga gaaatataag tactgtatgc atattgttgt taagtatttt  88740
ttctgtttgc ttatctataa ttctaatttt gcttcaaaga acaagttact ccggcaatat  88800
aaaaataaaa taactaattt gtcttgtcat caaacagata gtaagaacag gcaaacctgg  88860
ccctccacac tgccagcctt ttgtgattca aggcttcagt ttcctccact tgttaaaaag  88920
attcaacaaa gtagttgaaa tagtatgtga accagtaaac cctaaaaggt gtccagtgtt  88980
gtctgtgagc taattaagtg atttgattct gactccccga gtcttctgat ttcgaagcag  89040
tggggagtca gacaggagcc tcaggtggcc tctcctgaga ggccctggaa agtgatgaga  89100
acctggcctc tggcagctct tcataaacgt ccatgttttc cctctactct ctcactcttt  89160
tcccagggcc tcaaacagaa gatgaaaatc aatttctaaa acagccctct gtgtgctctc  89220
tcgtatctct ccttttcaca catcgtggtg gtggctttct ctgtgttcct ctgttgattc  89280
agtctctgga attaacggat caggattcca tgcccagaat gctacaaaga ctgtgcttga  89340
gttctcccac atctcactca attacacaga agtttcagat tatgtaacag atgctgtgct  89400
gggttaggca gagccatctg acttgttttg ctttatttta gaccatgaga tgggtgagtt  89460
tttcttttta atgccacatt cttttaagaa ttaaaaacct ccacttggct gtcagcattg  89520
gaaatcagag tgatggtgca agccctgatg aggacaatgt ccttgtctat gaaaaggtga  89580
aatcattgct tgaaatcgct aagcaggaca tgcagtccca gatggagggg ggaattcggg  89640
agctggttgg aaaagagtat ttggcacttt gcagccttga gaggtgcaga agagacaccg  89700
aggggttcac caccagagcc accattgtca gagaggcgtc cagctgtgtc cacctgggac  89760
tctgccttca gggcttcttg cctggctggg agctgcacag gcagactcct gggacggtgt  89820
gccgacagct ctgggcaccc ccttctagga tctgattcct gaggaatcac aatgtggatt  89880
tcacaatcac ttccagtgtc ttttgccaac ctctgtgaac agatgtgcaa ttaaaaaaaa  89940
aaaaagaaag gggcccaatt ctcaacactg taagtggaaa ctttttaatg gaaaaggata  90000
ggctaatgaa ttgaatttga aatctgagac agaaccgatg catcaaatgt gctggtgttt  90060
acagataata caagggggc tgcatcttat ggtttcaatc cttttttaaa tttttgttct  90120
gagagaccca gccagcagac tgccgccagt cttgtcagag atgtcagtgg tggccactct  90180
```

```
gaatggaaag cagcatctct cagcatctct gaggcactgc tcctcagcgg agactgtggt  90240
ggctttgcct ttcagcacgc atcctttcta cgatgcctga cagtgcccag ggaatgggca  90300
gagctgggag ctctgaagcc ctttcaccta aaccaccctg ggtcacctga cctagttttc  90360
ctcccaattt taattatgtc aggcacttca caaaggcctc cttggggaca ccatgagctc  90420
actgtcatca gattgctcca atcacagctg tggcttgcac acaaccgcca tctctgcccc  90480
agcagatgct gtgtgtaaac agttgtatta attacatctc aaaaacatgg ttcttgccag  90540
atcctcagga tttgggtgca gcctctgagg tgggtgggag gccctcgagg gagaaatgtc  90600
tgcaggaaat tcttccccta cgagaggtct gttttctaag ttatctaaga gctactgcag  90660
ctgtttactg cagagtgacc ctgctcaaag ctgtggtcac ccaaggcttt gaaaggggac  90720
ctccacttcc gccctgggtg gagcaccgtg ctggagaccc acgcctgcca aggcctcatt  90780
gtcatctcca cacgccgtcc ttggggtggg ccactcctgg gacacgcaga caggaagccg  90840
gccacctgag ccactcggag gctctatcca gagtcagctg ccaagcctca cgtcacacat  90900
cactgttagt cttggagggc tggcggggcc ctgaagtcaa ttgaacactt ggatgacagg  90960
gaacttgcca ctgccagagg caatatgctc catttttttg acagttccaa caatttttct  91020
ttaaactgtc ataaaaaatt gctgctgtga ataccagtgt cggcgtccct gcctcacctt  91080
tacctggtgc ttttccacca cacaaaactg tttctcctcg tgctggcctt gggcttgcag  91140
acagctgatt cttctcctcc cgcggctgag cagcctcctc cgagcaaccc tctgacaact  91200
ctgctccttc tgacaacctc tgcaagggct gccagatgtg aacaaggggc ccgggcagaa  91260
ggtatccagg aagactggaa actcgaggaa gcctgccctg tcctgtccac cagactttac  91320
gcttgcgtca ctgggctttg ggacctaagt cctcgtcatt tgttcctttt gcagttccta  91380
ctgttctcag cacttccttc cagcttactg aggtacactc agatgtgata tgccatcggt  91440
acagacacag ttctgctcca gcatttcccc gtgttctttc tgtcgctcta tttactgaat  91500
taccgtgagg atgtggagcg aggctgagtt ctgtatttta acaccatttt aattctcacc  91560
tactgagaaa tccatcctct tatcactgtg cttttttaa cctgtcacga atccatgaaa  91620
tcctatcagc cagcctgcat acttcctttt aaggtgcagt tgaatcagga gaaacttgcc  91680
gcacatgctg cgtccgggca cagcattggc tgaggctgct gccctgacct gtccgctttg  91740
tagtactgcc cagctatgaa acaggttagc cacacatgac ctgcatttag gagtaacaag  91800
tctgtctgta catgcacata cagcaacttt tttaaactgt ctatattttt tcctgagata  91860
ggtatttata atatctccat cttctttccc attttgaaac ttagaacaag tttgcctgtc  91920
aacagttctc cacagcatac tgtgtattct aggattttct aaggttgagc aacggaggtt  91980
cagcaatttt gacttaattt cttcccatcc cttttccacg cagcccagaa gccttggatc  92040
acgtggtgag gggaagaggt tgtgctatgt cgggaaactc tgtatcgaag ctcggctcag  92100
atcatgacat tctcttgact aaaaccctca gtttccatca aacttgtcac tctggcatta  92160
aagcctgtca ctgtgtggct ctgaaaacct ctctgaacgt gttccctgcc tctgccctgc  92220
aggtccctgt gctccacaga agcccactta tgtgacccac ccccactcat caccaccttc  92280
cctcacccag agcctcagct ccccactccc acctgtaaga cccctactgg aaagattccc  92340
acctgcccct caagattaat ctccaaggac atttccaaat tcctctcccc atctctcagc  92400
cagatggctt tgctccctcc aggaacccca gccaccttcg acctccagca gggcactcca  92460
ctccacattc tcctggtctg tctggctcat cttacctgag ccatgctctc caggtgaagg  92520
actatgtcta actcaactct gctttaaaag cagctaacac attgctcttt gcatattgtt  92580
```

```
cactcactaa gttgaactgg acttggacat gcacactgaa ctgcagcgtc tgctgcttct  92640
tggtggccca gctcgtcaaa agaataagat ttcagcaaaa caatgtaaca atttttttta  92700
ccaaaagtaa tgttaacaat atatggtttt cccctgatgt ttgcgtcaaa atgctttttg  92760
gaaaaaacat ttttcaactc tttagggtca gaattaagca atgaaattta tataccacat  92820
gtataatgtg tatgtttatc taagtatctg ttcatttata tatcttaaat agaaatttta  92880
aaaatttttt taaaactcct gataaacatt ctcaggaggc acactatgta actgttggtt  92940
gatataccta gctagatggt gaaatcagat tttgtttaaa gcatggagga gagggaaaaa  93000
ttaaatcttg cagattctgc agtccttaac atctttgaaa gaggaacatt tcagacaatg  93060
taataagaag gccacgtgct ttgacttctg tagattttaa aaatacttct gtatagtttc  93120
ttcttccttt gaagaagttt ggggagtttg ggaagatgga gaaagatata agaatagact  93180
ccccatatgg gtcatgaatt atctttttgc atcagaactc ttagtgcagt ttcagtattt  93240
tcttcctcag gagggtgagc tgcttccgaa tgtcctcccc ttctttgagg catcctctgt  93300
tggtgaactt tgagagcatc catttatgaa gttgatgacc tttcccagtc tctgcaagcc  93360
cttcagtgtg tgtcctctct gagcaaatct gaattgtgtg cttaatacat ggaaagggat  93420
ttgggagggt tgctttttaa actgatttct taattaatat tatggtttag ttaactagac  93480
agtctcattg cagaagtgca taaccataat atgtcttcaa atatatctcc cttcctaaca  93540
ccctgtaata tacttttgta aagataccct tacagaatgt gatccaccat ttatgaacct  93600
gcagcattgc attcagagac taagtgaaaa gctggcagat tttcatttaa agcacaagct  93660
aaggaagaaa gctggtctag aaggagctac agaagggtaa tgcttaggga gggaatgatg  93720
tgcctgtggg tggtggtagt taaatctaac caaagaatga tgtcgtgggt gtttggatat  93780
tggatggtcc acattgggcc acattctttc aaacataaga gtctgtagaa atatgacctg  93840
taaaagactc ttaaatattc tggaaactgt ttcttccttg tcacatcctt atatatactt  93900
gaacctatgc ctaccagaca tgacatgtga ctattcatac agatttcatc atctctggtt  93960
taagaataaa ggatgctgca tagaaggctc acatctttta attcacaaga ctgaaactgt  94020
tctgaaatga cattgtttct aaaaattcat tacttgcatt atattcattt ttatttttcc  94080
atgccagaag ggtagaagtt cctgtgctca tattaagaaa cagcaatgtc aatcgaggcc  94140
caactcaaat ccaatttata ggagttataa agggcgtgtg cctgttttgt ctagaagcag  94200
tgttgggcag cactgagtag gatagaccac ctgttgctac cgataaagga gcagcttctc  94260
gaatgctcct gtctggtagg cactatcccg agtgctttgg cccctcatcc acaatctgtg  94320
tggcaaaagg cattgcaggc aattcagtga ggagaccgag gcatggagag caagtgccat  94380
ggaattccct aaggccgtgc agggagcagg ttgccaagct gggttgaaac cgtcctccgt  94440
aggctcccaa ctccgccgtc gctgctactg tgctggatga tgcctggtag atgcagatgt  94500
ggagccccat ggattctgag acaggccggg tttcagtcct gccctagctg cctattggct  94560
ggatgacctt ggcaagttga ctttcgtgag cctcatttgt ctcatctctc aattaagaaa  94620
acctagagcc tatctgtggg ggttatctga aggattccag ggatgcatat ggcactgtct  94680
accgcatgcg gtaactgttt cacaaatgat gaggagcgat ttatgttctt agtggaaata  94740
tgtcggcgtg tgaagtccca aagctctgcc ctgcctggct tgatccagtg cctaggcact  94800
gcccctcttc ccctctctcc caacccactg taagaggcta ggctgcctca gtaactctga  94860
ggggcattga ctcttttcat ccaaaaaattc atgttactgc cccacatttt ttctgttgtt  94920
```

```
ttacaacgca gtaggaagtg ggcagactgt caggaaaagt gatttatagt catgtattgc  94980
ttgtgctttg gcttcatttg atccaatgca gatcagctgc actcagaaaa ctactcaagt  95040
gaaagagaaa aagtaactga agggggaaat ctggatgagt aagaattcca gggataggaa  95100
tattaatagc aagctttttg cctgatatag tcactttatg ctgcaggggt gccccttat  95160
aaagtgcttg tacaatggat gtttgctttt gattttggat ttggagtcta atgaatgttc  95220
taaattatta ttagaggagc ttgcggttgt tacatgtctg cctttattgc ttatttttag  95280
ccatctcccc tgatgtcaaa tgctcaggca agaatgatac attcatttat aatgtggctc  95340
cttcagaaat ataccacata ccttttggtg tggtttgtgg ctgagaagag tggggaatgc  95400
acaagtggaa aactgcagaa agattatgcc ttcatcactt caagtatttg agatgaaact  95460
agatcatttg ctgttgcttt ttattctcat tctaagtgct tttcaaagtc agcgctaaga  95520
ttttaaaatg gttttctgtt gttggcagag agggaattac tctattactt tctgataaaa  95580
cagagtcttt catgatcaaa gagaaccagg ctctagtagt tccagtatcc taacgtggac  95640
actaattgtt tccctccttt tcttcatgaa aacagcttct gcacaaatga tagccttgtg  95700
aactagccat gggcacaact ggagaagcat ttagggagct ttagtgcaaa ttgagaccac  95760
ctacacatct gactctacag ggtttgacaa catccagggt gaatcacaaa acatcagtct  95820
aatcagggct tatatagaaa gagtgaaaga actctgattt catcctaaag attatttata  95880
ttaaccattg ttccaaatgc attaactatt ttaatttagt tgttttgatt gttaaaaaaa  95940
acacatctgt ttggtagata agacataatt taagacaaat gttctatttg ataagctttt  96000
agaaacaact tatttttatt ctttcctgtg agataactca gatgtggaga atgtgacaaa  96060
attttaagca taacatgaga agggctgaca cacatagatt tctgtgtgct tacttgaaaa  96120
caacaaaatt taagaatttg gtataggagt tgtatcaggt agtgcagagt ccccaggaga  96180
cctagagacc caggtctggg agcctagcgg caagggctga atgtgggatg acatcagcag  96240
aaactcacag ccactgctat tccaaaaacc cagcagcagc tcagtgcagg gcagtgctga  96300
tagtacagtg cctgcaatcc tggagtggat ttggatgtgt caggtacgca cacgctcact  96360
gctcccccag cagtacgttg aacagtgtgc gtccaggtgt ctgtagggcc cctcgcccta  96420
actcacaaaa ccattctggg tcagaagcca ccaatattgt catcatcctc ccttttctga  96480
gaaccctagt aagtccctcc agtggggcaa gcccaccttt tcccttcatt ctgtggcaat  96540
atgccttcat ttcctaatca gttttgccct gctcattcaa tgcaaaatgg atctgctttc  96600
cttgggcacc aatatgtcca gggattgttt atcaatcttc agttctgttt cctttacata  96660
tccctccaaa aatcaggcct gcactgcctg tgcactccac aatccacagg cctgaaggaa  96720
atgttatctt tgatgtagag acttaaagta aaactcttca aattaattat ttcatgcaaa  96780
aggctagtcc tgactctaat tctaagacat gtctcctaaa ctctggaagt ctgatgtatc  96840
ctattatcaa catttatcct taatgtgatg gtttatcatt tatcctcaaa gctgcattgt  96900
aaaatgtaca ctgtaaagtg tacattttaa agtcggtttt aaaaaatcat atttagagat  96960
cctggtaaaa atctatcaag tcaagacatt accttattac ccatggaatt gtcttcaact  97020
cttacagttc aaatattcct gaattggctt tcacaataaa catcctaaat atgtaagtag  97080
aaacatatat attgccaact ttgtgccttc ccaagcaaaa ttaaaataca ggaaaagtca  97140
gtttgttttg cccataaata aatatatgtg tgtgtgtatg tgtgtgtata cacatacaca  97200
ctcagaaaag atagaagcag cagcatattt tggcagcatc tggtttattg gaactcaaac  97260
gttctgattg tgcatacaga ctagttaatg tggtaacaat tatgtatttc ttccctgctc  97320
```

```
cttgccttct ttccctcccc agttttttc ttcctgatag taggtgtgta ctttttttcct  97380
atttccattg gcaagccaca tgacaagcaa aacgatcact cgaagaatat tgttccctca  97440
atcaagaaaa atgcccattg ggttttgtta tttgatgtta tttgatgaca gagacctatt  97500
gtttttccat ttttcttttt ttgttttccg tggcacctat ggaattaagc aatataaaaa  97560
atctattatt tcagatgttc acgtctaatg aatttcatgt gaaatactgg cagtataacc  97620
ccaaatagag gaaatttgtg aagagtggat gctgcagggc atgagacatc tgcacagagt  97680
tcatctcttc cagcatcttg catgtcccaa gcactgccct gccaggcaga gaatgctgca  97740
gatcacggca gtgaattcca gttgttcaga gcacatttga cttccaaatt ctcaaggcca  97800
cagatttgag gacagaacaa tatttgcatt tgaaattgga agattatttt ttgcacaagt  97860
gcctatatgc tatatagagt ttgcccactc tgcattatct tccccctgtt cccccgttat  97920
ctggcacaag ctattcaaaa gacacgccta cttgtaaaat aaatggtttg caaactaagg  97980
aaaatactta aatctcatgt aaatggtact atactatgta taaaaatgtg aagaaacaca  98040
gaacagctca tgaacacctc cactgctgta taaaagaacc atctttttttc tggctcctat  98100
tggatgcctt agaaaaatct gtatttcctc tttagttatt gtgtttgaaa gatgaagttg  98160
agacaaaagt tctattcttt ttaagttggc agaacttctg aaaggtgatt tttagctgca  98220
gtgtgactca ttccaaatgc agaaatctct gaccctgagt tagtctattt gtcatgcaag  98280
agcctagaaa agccctgagt gataagaaat ggccataggc cattcccaca gaattttcaa  98340
caaaaataga atcatgctta tgttctagtc atgacttaga acttataact catgttcgga  98400
actgtccatg ttcacgcaca ggggccgtat cactccgcca gagctgccct gggtgccggt  98460
gtgcagaggg gtccgagagt gactgtctct tcctctgttg tcgaatgtgt gggttatctc  98520
cataaatggc tgccatgagc atccttgttc acacattttt aggtacttga gtgagtgtct  98580
gtggaataat tttgggaagt gaaatctgtg gtcagaggtt tgtgagtttt acatgctaca  98640
ttttcagaag ttgagaaata gcagtaggct gaaggcaagt cgccatgcct ggaattcatg  98700
aacactagtt gaaagaactg gcgtgagtta gtcatgacag gagagatggg gaagggagtt  98760
gcaggtagga gggccatctt caaattctca aagtatagtc actccaaacc aaaattcgat  98820
ttaatctgta ggactccatt ctcaaagcac agtcactcca aaccgaaatt cgatttaatc  98880
tgtaggactc caggtggcag aataagaggc aatggatggg tggaagcgaa acagggccaa  98940
agtttgactt catgtgcaac ttcctaagga gtgatttgaa ctccacaaac atgaactaag  99000
cacctcaaca caggctgggc aagttgctgt tcttttggag cttacatctt agtggggaaa  99060
gagaaatgcc tatgtaaaca tataaatcag caggatacat tgtgaggacg gtcattgctc  99120
agtgagactg caatagagtg atacgctgga gggggctgca agggagaagg tgggagggac  99180
agcatttagc agaatgagca gcacagtccc ataggaagaa gaatttattg cctccttagg  99240
caaataaatt cccaaacctt gaacatcaga aaggaaatag attaatgtgc acagaggatt  99300
aaattatgtg atctgcaaag tcatttaaaa tctatttcca cataaaacat attaatgcaa  99360
cctaaacaaa aggggtctgg ataccctcat cttcttccca agcatcaagt ctttctatag  99420
ttaaactgag atgcttttat tcttggaaaa ttttaaggac tatctacagc aatggaagaa  99480
tcgggtgttg ggatgtgttc ccaggtaata atgactgcag gctgatttgg cccttgaggt  99540
gtggcctcat ggccctctcc aaaaaaaaatc aaggacctgc tacaaagcac aaagccgact  99600
gcaatgcttg ctgcttactg gttagggcag ctcctctttg ccagcgacca agcagaaagc  99660
```

```
aagacaagac aggttctgaa gcagtaattc aaagccttcc tcgctttccc atgtgagtca  99720
ttgctagtca gaatattacc tttgcagaga ggcttaattc caaatttgct cttaaaggga  99780
tatcctctcc tggtttaggt ataaactttt gactcacagg acaaattcta tcattccttt  99840
gggcctagga ttgcatttat ttccatgaca aaagggcctg tctggtgttt cagcaaatga  99900
aaacaaaaat ataaagccca tctccttttg aatgagctct aaaacagttc tccactggac  99960
ttcagaacaa gagggagctc tgggctgctg gctggttgtg catttgctgt gggttccctc 100020
cggcaggcga cctctccgcg ctgagaaggt tatccggata accaagtaag aaagtacatg 100080
aggaggcaca gaaagaaaaa tgtgagagat aacagcataa acacacagtg tatgttgtta 100140
tgaggcatca catgatgaga tactgctggg gagggaagaa gtgaggagat tcctaggaat 100200
cttatgagaa tttccagaga caacaagttt tgagcttttt tttaatttag aaaatttacc 100260
ttatttttaa aagaatatgt aacatatccc atgctataaa attctagaca tagtagattt 100320
aaaacagcat aatggaaaat ataaatatct attttctttt cctatttatg tattctgtgc 100380
cagtaggaat gtagccaaaa agagagaaaa ggggtctctg cagacatgga tgtctctgtg 100440
acttgatcac tgctaaccca agaagataat aaagcagaag catgtatcca ggttgctgca 100500
gccaagcctg cccggtctgc ggggcgtcct cacacatggg gcagctctcc caccccacac 100560
actgggaaag gcggacagag gctgggcaaa gcccccaatt ttcgttggca ctgaccccga 100620
tgatttatag gcctttgttt cccatgttaa atgtcttacg atcattaaat tatttatagc 100680
tcaattagca tgtgtccaaa accaggaagt tcataggaga ctgtgtgact gggaattaag 100740
gagcaaagca actttccagt ctgtgattta ctgggtttcc attctgtttc ctgttcggat 100800
ccggaagtag aatttcaaat attgcttttc atgctttatt tgggaccgat tttagccccg 100860
ctctcctttc tcttgccatt cgctggccat tagccaccag cctctgcaca atgaccagct 100920
ggcccctggc agatcttggg cccaggtgtg aagtcgctgg agaagcattt cagggccaag 100980
atgggagtga tttcattttc cattgacact atgcagaaat gaaggggatt caagtgcctt 101040
cagaaaagct tccttccagc gaatggagtt ttgggggttt tccagacttg caactgcttt 101100
tattcttgga agcatcattg ttgctttttc ccccttcca tttatatccc aggaactgat 101160
tcagaaacca tagaaattgg atttggaatc gctgaatgct agcagacagc tgactgcact 101220
cttcccaaga aaccctgcca gctgggttcg ggtatcgcgc ggtgtgtgct ctctctgcct 101280
ggcccgctga gtcctctaac tctaatggat tccttcttac accaaagtgc actagaacta 101340
aagtgttttg cttcattctt tagacatttt gtggtttagg gctcaatcag ccagggtatg 101400
atttgcaatc cacagtaacc ggtttcagag cagctgccca gcgaggcagg tttcatctcg 101460
cttgctagac gttttgtttt tttttttttc taaacctcac accttttatt tattagactt 101520
ggattccagt ttcctgagcc tgtttgtgcc actgattaga caggcttgaa gcagaaccca 101580
ccaggcttcc tgaataaaat gcagcagtga ttgtattagg gggttttaaa ttgctcaaaa 101640
tactgtctaa aaaacactaa aaatcatgtt actttctaga ttgaataaaa tcctatagaa 101700
atgaattcct ggacttgata tgtagcaagc tggcattggc tcgggagtga gtgggctcag 101760
ttaagtgagc taagatgaga tggtgcacag gcgagcaccc acctgaggag tgtttggatg 101820
ttatgatagc cagctcctct gtaaagacct gtccttctat gtcagcagcc cagcagataa 101880
atgacgtgta aataccacat ttaggagggc ttatgatgat gccaattaat ggagaccttt 101940
ttgaaacagg aaggaggtga aacatattcc tttgcttcta catcactgtg tgccaggcac 102000
tgtttacagc atctcgttta accagcagtc accacctgac ggatggctga tgtggggtgg 102060
```

```
ggtcccaggg tgggattgcg tgatgggctt ggggtctctg gctgatgggt gccagagctg 102120
ggactggaac tcctggcgtg actgaggcag acacctgggc tacccagcct cacccacgac 102180
gccctcacta agtgacccac aggactcacc ggaagcaggg cagcaaggtc cccctacaga 102240
ggtccccact gcaaaccgat acccagctta gacagcagtt ctgcagtcgg cgtctcaccc 102300
cttcgggtct cattgtgact cactttgata gccacacgat ttaagggtgg ttcagtagtg 102360
atttgatgag tgctgtggct cagggtcatt cccctgccca agcatttcaa attccagaag 102420
ttcatgccct gcatggtggg tgaaaagtct caggccaacc atgagcacac agcagccagg 102480
cgactgaggc agctgcccgg ggtggcacgt tgctcaaacc catcatttgg agtcaaaaca 102540
aacagatgat tagctggggt ggtcactttc aatcaagagt tttcacatcg cctagacatg 102600
gcctcagaat caggcctggt gtggccaggg gctgatctca cagtagacag gaagtgtggc 102660
ccgagggcca tggctgcccc ctcagaaggc cctgtggagt ggctggccga gcctcagcag 102720
cctcctgtga agcgaggaag ggtcttcctg ccggcctctg gagatcagta tgggaatgca 102780
caagtaggaa acgctggatg ggaatccctc tgccctgtga taccaaggca gtgagtttgt 102840
agactatgga attgctgtcg gagggctctg taaccggcca aggtcacaca ggtagccatt 102900
ggtagagcag ggactggaat cccagacccc caacttccag gactgtgcac ctttctttat 102960
cccatacagc cttacagtca agtgccagtg caacacctga ttcccaggtt ccagcctttg 103020
tcttttataa tgggaatcaa ccttatcttg acgatccaga gatagtcatc aaggaagatt 103080
aaattatccc cttagactca gagtgaccat atcattttcc ctccacacaa ggacactttt 103140
gagaatgaaa aggaggagat gtctgtacca gacgctggat gacaggcacc gacaggctgt 103200
ctgccagggg agcagcgatt cctgtatgtt gtagaaagtt tttcaaaagt caccttggaa 103260
agaggttttg ttccttaacc ttctgttaaa taggaagctc cgtgaatgaa aacaactccc 103320
ttccctaaac attctagtaa tgacccaaca ctgccaagcc tgccagctct gcctcatggt 103380
cgtgttgact gtgtgagact atgtgagtgc ctgctacaca gtacgctttc agtaaacatg 103440
gtattgcctc gataatccca caaaaatgtc ctattcaaat cacctggcac ccaggaaatt 103500
tccttctttt ttttcccagg tgaaatatac agttgaaaac acctgacagc aattcccctc 103560
tcccatgtgt ttgcaggatg gtggttttgg ttcctccatc tttgatgtgt acaagtgtga 103620
tgttttcccc ccacagacaa gtaaaccaca ttctcttcac attcccaatg ttttgtcaat 103680
gtacctcctt caatagagga tcgataagga aaaaaatcat tgacaatctc aattagattc 103740
actatttcat ccaaaagcat agcttagaac tctagttttt gttcaacact cttgccctat 103800
gagtgcacag aactttaatt ctgatacaaa catccctgaa tgtttagctt tgacagagat 103860
tccaaggtga tttgataaga agcagggctg tgtttgggct ctgggagttt ttgatatggt 103920
ttcaagcccc atccaaaacc cacagacctc tagaaagtag gtgcctgcct tcctgcagca 103980
gccctggagc ctgctggggg ctttgagcag ctgctgccaa gccaggcctc acccgacact 104040
ctgatgggca cggccatggt ggcaggggct tggacgctgc caggtgactc taacttgtgg 104100
ccagggtggg aagcactgct ccacagaggt gccaaaacca ggttccttcc tgtgttctca 104160
catttcacag cctcaatgta aaaagtaaga catgggcact ctggaatatt acaaaaatat 104220
agaaaagcat gttatagtaa ataaaaggct cacagaattt tgtcatttag gaacaatgat 104280
tattaatata ttagtgtgtg tttttgctca ttaacagtat atcctgagat atttcctata 104340
ccatttaata ttttaaaaga tgtttacact ggccacagta gctcatacct ataatcccaa 104400
```

cactttagag ggcaaggcag gaggatcact tgaggcttaa aaattagcca ggtgtagtgg 104460
cacatgcctg tagtcccagc tactcaggaa gctgaggctg gaggatcact tgagcccagg 104520
agttcaaggc tgcagtgagc tataattgca ccattgcact ccagcctagg tgacacagtg 104580
agaccctgtt tctaaaataa ataataaata aattaaaaca tttaaaaata catgatgttt 104640
aattattaga ggactcaatt ttatatctat gtatacaata atttttaagt ttcttaatat 104700
tggactttta gtaccttttt aaaaatacta tttttaaaaa aatctgtatt tctaactttt 104760
tataacaagg aacctttggc tttgagatga ctggggaatc cattctttcc tatagtatcc 104820
atgtccaatg gacttaaagt attaatcaat gtgtttatgt tttgttattt ttctggcatt 104880
acaaaaaatt ctaaatatat tgttaccgcc tgtataaata tcagcttttg agagaaggac 104940
attgtgtaga aataatgaaa cactgcaact tgtatttgta ttattctttt tttttttttt 105000 tttttgaga tggagtctcg ccctgtcacc caggctggag tgcaatggtg cgatctctgc 105060
tcactgcaag ctccgcctcc caggttcaca ccattctcct gcctcagcct cctgagtagc 105120
tgggactaca ggtgcccgcc accgcgccgg gctaattttt tgtattttta gtagagacgg 105180
ggtttcacca tggtctcgat ctcctgacct catgatctgc ccgcctcagc ctcccaatgc 105240
actgggatta caggcattat attattcttt aaattcacat gagaatttag tatggcttca 105300
aaaaatacca taagttaaaa tatcaccaag actctgttca gacaaaagta tcagaaaagt 105360
gagccaggca ctcacatagt ttatagttta taaaagtgag acaggcatga tctcttaacc 105420
tcactatagt cctgtgaata aggtttattt acatttcatt ttacctgcca ggattattgt 105480
aaaaacgcca agcacattgc ctacacaaac taaatattca gtcaatggct gctattttca 105540
tgagttcgtt ttaacatata tttattgtcc tctactggat ttaagaagtt atatttatta 105600
tcatctaaga ttttagctat tccttctctt aaaaatagat tttataatca atggcagtaa 105660
gggagagtaa ctcgcagttc tctgaatctc aaggggttcc tggaagcctt cctgaaggta 105720
tagtgaaatt tcagcttcac attcccatcc atgagctccc tgcaaatatc ccggtctgct 105780
ctcaggaccc agtgacttac ctatgcagag gctgtagata gcacctggag cttcctgtgt 105840
gccctcctca aactcagcca atgccgtcat acagtagcag gcaggtgtct ttgctgggta 105900
gttggactgg atgtccctgg gattgcagaa ctggaatggg gagtgacatc aggaaactat 105960
aatcatcagg acaacatggt ttgccataac tttaagtttt aagcgaccgc agattatgcg 106020
gagagagatg catgcccaca gccatgcttc ccatgtaact ggagaggggt ctgaagtttg 106080
aaacaagtgt tcctaggcac gggttacagt gtttgttatc atcatacttg atttagaatg 106140
gggcacaaca tgtggattca tggtaactgt tacaacctta ctcattttaa tacctgaaaa 106200
catgctttcc ccatgctggg aatcgaaaga ttctcctagg aaaagaaagg cttgacaaca 106260
tcgattcaaa aagggcatgc attttcctca tttaaataac tctaatgtgc aagtagatcc 106320
cctgacctca agctcagaag agtccaggcc ttcacacctt ctctgcttct gctctggggc 106380
cagctattga gattcctgtg cccacgcaat gcgcacatcc cacccctggc cgctgtccac 106440
aagaaatcca gttgcaccaa gcaccccact ttttgcacct ctcatttatg tactcctaag 106500
agcctcacca caactccctt ctaaaaacat gagttcctga ctgggaattc gatgctgccc 106560
aggcagcttt gctcagaggg agcagccttc tagaaatgtt tcaagtaaac tttcaagtat 106620
aactaaattc aaaaaaaaca catacacaca cacacacaca cacaagtcaa aggtgtgtaa 106680
tttggccaat atcacaaacc aattagccct ttgtaagtgg cacccagatc aggacagctg 106740
accataccag caccctagaa gcaccccgtg ctgcctcctg ggacagggct accaccatcc 106800
taaggccagc acgatgggcc agctttgcct gctgttgaat tttgcttaca tagaatcctc 106860
cagtaggtac tcctttgggt caggttcttt cactcaacat tatgtgttga tatttttcca 106920
tgctgtgctg caaaattgta tttcttgcat tccataactg ggcagttcca tcataggaga 106980
ataccacact gcgttcgtcc attctaccgc caatggacat atgggttctt tctcttttct 107040
tgcagttaca agtttatgaa tattgtccca cgtgtccctg gtgaactttt gtttgcattt 107100
ctgttgggta cctcagagtg gcgttgctgg gtcagagggt actggtcgct ttagtagctt 107160
tgaaagatat tgccaaaaca ttttccagcg cagttatagc aaattataca ccaccagcag 107220
tagaaaacat ctcctaattg ctcacagtaa acccccaaag attgccacat acatcttcca 107280
tatcaattac ttaactattc agcaaatttg aagggaaata tatttaatct ttttattcaa 107340
atagtttata aagtggaata gagatgtggg taaaagttgt cttgccacct ttttagatcg 107400
gtaaaagttt gttgaatgca ggcaagaaaa gatgagaaat aatggtaccc aatgaaagac 107460
atagcagtct acaaggaggg gcatttcccg gggtgggggg gacccacact ctgtaactcc 107520
cacattcaat tagcatgtta taggtaagct gcagaaaacg aggcagcttg tcaaagagga 107580
acggctcttg gccatggttg ctgccctagg aggatatttg atactagcag agctggggca 107640
accctggagg aaaccacctg gaatgatggg agaactcctc cagggaacat ggccctttaa 107700
tagatctctg ttataaaaaa taatcccaaa gcagccacca gggcatactg ctgcgatcaa 107760
gtcctaggcg gtattccctt ctgcgccata gaccctgtgc agagtgccct caacgaagga 107820
gcaaggaaga ccaagtctcc cgagggtttg catatgtgta tgtgattctg cagtcatggt 107880
gaatgacaca gtcagggctg cggaaaagca ttggtaaagt gtatatttga ggcttcagaa 107940
gtttgaaaag gctagatttc ctaggccaaa acactgaaaa tttgcaatta gaacttcagt 108000
gctgatgctg ggaagactgg agttagtttg agacatgcac ctgtgcagaa ctgggccccc 108060
agaaaaggag aaggaaggga atccagacca gagtagggcc tgacaccact cagactcggc 108120
gtgtctataa attagaattg cgttacaatt acactttgac attttagtgg tttttaaagt 108180
gcccagcaca agttaatttt tcattaatga atcctttatt cataaaatgc ttagatggag 108240
attacccttt tgagcatttt gccagtgctt ctgaaattaa tggggacctc ctgttggagg 108300
acacagtctg ttgcaatagg tgaccactgc tctgaatcta tgtcacctct ccaggaccac 108360
gggcacaacc atcacctgag gcatgttgga gatgcagatg gtcaggccct cctagaatct 108420
cagaatctgc attttagcaa agtcctgggt aattcctatg tccattggag tttgagaagc 108480
actggtaatc tcaaatactt taaaagatta ctagagtaag ataggctcag taggtacctg 108540
aaggcaccat cccaaagacc agagtggtag aagcaggtgg accagcctct gaacacattt 108600
ctcccccact ccccggctgt gtggaaggtt gccacctttg ggtagtcat tcaacaaaca 108660 cgtgtcaact gtccactatg tgtcaggcca ccactgggca ctggctgtgg ctagctggat 108720
agacaccatt tctgccctcc agaaatgtca tgtccactgg cacatgacaa gtcactaagt 108780
cattcagagc catgggtgac agctccaggg gccgacaaag gagctgtgat ctcacagatc 108840
cacagagaag tgtcccaggg cgggcgggaa ccaggactgc acagggaggg gtgaagtgac 108900
acataagaag tcagcccatc agcctgaaat gctcccccaa atcttcccat tcagtgtttt 108960
ctcagtagca aactcgtggg aaaattggtt attttactta aaaaactcat actagaaagc 109020
tagtttaact ttaaaaataa attttaaaaa catttttatt aacaaatcct acctttcctc 109080
caaagtcaag gagaaaagaa tagaagtgaa caatggacca agtaagccta aaactctgct 109140
ctttcccctg ctcattttac agttcaagtg ccattcaatt tatcctggca agaagaggaa 109200
ggcatcatca agaccttaat tttctaatac atctgatctg agaagaatgt gaaagctata 109260
aaattaattt ttgatcaata actacaggcc ttttgagaga gtgccctcct aatgaattga 109320
gtacctattt ctccatacac agtgtctatc atgacctaca aaccctttttc ccatgaggtg 109380 taacagagag agattacagc cttggaactg gatgtcagac tctcctggtt taagacaata 109440
agccatgaca tagagcctga aaccaacaca atcttccgag tggttccaga aacatatagg 109500
ggataatgtt ggctctgatg ctgtacatcc ccaacaacca tcaactattt ggaaactaga 109560
atttcagcat aattggagtt ggtgttaccc tagcaaatgc tgtgggaaga gagtctcact 109620
gtgtatcttc tcctgtttaa agcctgaatt tgttcagaat gtaatatctc tgtttagcca 109680
ctctactgaa actgatctag gaaatgttca aaaaaaggta tcccaaggat ccctttgtag 109740
ctacatctgt gggattcccc tcgctctggc gtggcctggc cctctgcat ttgacaatac 109800 ggtcctatgc ttttgtcttc ctgggctgcg tgaacccacc ctgccctggt tcacctctcc 109860
tcttgaccca tccttatcag tgtcttgaaa ggtccttcta ttggaggaca cattctgttg 109920
cagcaggtga ccactgcccc aaatctgttt cacctcccca gggccatggg cacaaccatc 109980
cctggagtgt gttagagatg cagttggcca ggtcctccaa aatctcagaa tctgcatttt 110040
tgcaaagtcc tgggtaactc ctatgtccat gagagtttga gaagtactgg tctcatgagt 110100
tcctgacata caaatagtgc tgaggccagt atgctgactg ggtagccaga tacaagtgaa 110160
aaccttcctg ttttttgcaa acctggatgg acccgaggcc gctgacgtgg gccaggacaa 110220
gctactcttt ttcagtgttt ctgttgcatc gctgtgtctc tctgtgatca ggtgctgccc 110280
tccctggcag gaggactgca gacaggatga ccaagagcac tctacacagc ctgctctcca 110340
gtgttggggg acgccaccca ccctcgtggt tcctgttcat ctgcctacac gtggagggcc 110400
caagagggct aatatgtgac tatctccact tcctggtacc ctgtgtgaat aacttcactt 110460
actaaaggga tgttgagcaa ctttattaat aatgaagaaa gcactttggt ttgacaaata 110520
atcactccat tttttcattt gaaagttaac tcttgttagt agagaaagca atgtattaca 110580
accacaagga cgtttacatg gaaatgaacc atctgcaaag catcccccat tttcctttta 110640
aatcagccaa tgggtggtgg tgggagaaat attcaccaga gtatttaaca tctatccccc 110700
ttcctagact gtcagctcca tccgggcgga gactgttggt atctccacag cacacacagg 110760
gcctggcaca catccggggc tcagtgagca cttgctgaat ggtgaacaga ttagctctcc 110820
tgggaacgtt gttgacacat ctcataacac tggtttggag tggagggcat tcatcgggct 110880
gcatattcct atttttaatt gtattctcca ctggttacag cacctacagt tataaagaca 110940
ttgttaacat tgcttatagg aagacatttg atggaaatga gtccaaaggc attacggtta 111000
gaaactggcc aggtgtcatt tttgagagat tagataactg ttttccggta gagtgaattg 111060
cctgtttgtt gcaagttggg actttgctgg gctggtttac agggccaagg ggaaagagat 111120
aagtggatct tctagtgaga ggtcatctgt tttgaaagcc tggaagattc catgaactaa 111180
atccaagtct tacaacacag ggaagtgtgt catactgtgc agggatgaag tctccaattt 111240
agcatgaaaa caagagctcc tcacactgtc ctcttcagaa agcccataca atccaaactt 111300
ctgaatgctt agctgcttac aaccatacat agattgaggg ataaaactct gatatggaag 111360
agaaggtaaa cattttttgg cagacattcc caggaaaagg cggctctctt ctctcattgc 111420
tgctgctctt tcagaatcca tttcaacaga ggaggagtca atgggagccc cgtgcctctg 111480
gcagatatca tatggcgttt cagtggcatt gtgtgttacc cttcttaggt aacagctcag 111540

```
ccattagaag aatgtcctac acaccttctc attttctgtg atgagaggaa tgtgaggtac 111600
tgcccttcga gagctgtcat ttgtcctagt agccagcagc gtgactgtgc tgtcttctgc 111660
tctgtctccc tgtcagcctt ctgcccagcc accaccacta tagttttgtt ctctccattg 111720
gaactcctgg ttcagagaat taccataaaa aacagacccc tagacataca acactctatc 111780
acataatggt gactttgtct tctattttgg attactgagc tttcttgggt aacttccact 111840
aaatcgaagt taatattaga agaacttcct cttactagaa tcgaaaagca tttaagtgat 111900
gcagtcaagt ttgtaccata agtaattcag tcatttaaca aatatatatg gcctctgtgc 111960
gacagtgacc ttgactggga atgaagctgt cccatgtggg gcctgttctt caaaggcagt 112020
tccctgctgc ccagttcagt ccagtggatc tgggcatctc tctttaatcc gcattagggg 112080
ctctttactg attcttcact atccaaaaag acttggaggg gagacctgag cccacttctg 112140
gaaggaaatg ataacaattt atttagataa tctttgtgca acaagtcaat tcactgaaga 112200
gatctgctct ctaggagcct ctgtgacccc accataactg ggaaggctct acctctccag 112260
tcttcgggcc acatttctct ctggcctgct gtcttcccag cactctcagc cttgctcatg 112320
gagcactcta gtcctccgtc gaccttggcc tttggtaacg tgatttttca cctggcagct 112380
cccatctggt ctcactccct ctttttgtcc agtctgcatg acacagcctc acatcgttag 112440
tgttccctca ctcccctctt actgcccaac ctgcaaagtc catgcctggg ccagtgcagc 112500
atgtgtcctc aatgggctgc tggtggcagt ggggggaacc gcacagccac gctgtgtgct 112560
gctgaagaaa tgcacagcct cctaccctcg ccctcaagag gcagccatgg ctgcgcattt 112620
ctgcccttct gagctccgct cacttttggc agcagccgtt ccaacctgca tgggatcttc 112680
actctctcac agatgtgctg actcctcctg ctgcctcccc tctctgtgcc ttctcactct 112740
ctgttccctt tgccctttct cccctttttct cctctgccta cctccaagcc atccatcaca 112800
ggacagctca agcatcagat cctctgggac actttcctta gttgttcagt ctgatgaggt 112860
gtccctcatc ctctcttagc tgaaaatcag cagctgcctc aacttctttt ccagcatgtc 112920
tcatgagtat tgccacaaca gcatctgtca caatgtgggg tagtggctga cttgcttttc 112980
tgccattcaa ctgagttccc tcagtgctgg ggccagcgtg cagtgtcttg tattcagtat 113040
atagctgatt aattgatgaa ttgattaatt aatggttcac actagcacag tgcaaccttc 113100
aatgcaaaga tctcatcaaa ataattcaca tggtgggata ttttagaagg atgaccaggc 113160
tagtttgtag taagaaaaaa tcaacaagac taggtcagga attctttttt tgtctacagg 113220
cttgctatag aagatattga aaatcatcta cctaattacc tttattttat caggttgtgt 113280
attaaatatc acgtctgggg gaagaaaatg tgatatgtga ttacagacct ttcctggtac 113340
aacatagtac gtttcagatt aactcaaggt attgtggtga tattgcggtc aaagccaggt 113400
gattaaagag tcattctttg aaacaaatat ctgtgcaatc aattaagaaa ttaatttgca 113460
aattttattt gcttagagta attgatatat cattcctttt acaaacaaat ataaagaaaa 113520
cttaactaaa aatactgcat atctctttca gattatatat cccagaaagg atatattttt 113580
ctcctttctg gtcttccttt ttggtgtagc atctgtagga aatgcatttc ttcatagcta 113640
agtgtacctc cttgtgaaat atcttcagag tctactggtg cacataagca attgctggca 113700
gcagcttgag ggtctccatc tcacatttat catatgcctt attgcatgag gctttgcaag 113760
aggaggtcta gagctacaat atctcatgga tatgaatgtc aattcaaatc ccagtggcag 113820
tttatgaggg ggaaagccta gaagagaaga aacctagagg aatcaagcag gaggggagag 113880
```

taataaaaga ctagagcagc aggtttttct taactcaaac tagaattaaa tctctgtgtg 113940
tgtgtgcatg tgaatgtgcc cgtatgtgca tgcatgcacg tgtgtaaatg gatgtgtgtg 114000
tgtgtgcatg tgtgtgcaag taagtgtgta tacgtgtgtg ggcatgtatt gtgtacatgt 114060
atgtgtgttt tatgcatctg tttgcaagta tgtgtgtatg cacataaaag tgtgaatgta 114120
catgtgtgct tggtgtatgt gtgtgtatta atgtatgcgt gtagttctag agtctagtta 114180
gagaaagtgc ataaagaaat agggaaatta acaagaaagc tatagcttaa attataggaa 114240
aaacttttct ccctatcagt catggtttta aaatgttcag acttgatatg tttcccagtg 114300
ctattgtcag aaaatgtccc tatgacattc catactactt caatcaaatc taaaaccttt 114360
gttccaacat gttttattga tatgagtata tttcaaattt ctaccaggtt tttggagagg 114420
tattttggcc ataaaattga ctaaattatt caaaataaaa aatgaataag cctgggccaa 114480
ggcttggaga cttgcttaac tcagttctta aattttcaga ttttcaaaat tacaaattta 114540
agctctaaaa tcatggtgct gtgtatgata ttctttgatt gcaacttatg gttgaaaaac 114600
tatagagggc tttatgctaa gagttgtgga tcttaggatt ttcatgaaat ctgcattatc 114660
atcatctgca agtttagatg gggcataact gatccaaagg atggatccct cgggggcaat 114720
tcaactggct gattccagcc aagatgacaa cagtcaggat ccgttccctt ctgatcatcc 114780
attgggtgcc ctgatttcct ctacagccct agctgaaaga ccagacacta tctcaggctg 114840
gctgccccac atgccttgct ccacaccaaa ttcacagtct ataaacctga gcctccagtg 114900
ctcctactac catactcact cgaacattcc cgattctgac ctggagatgt caacagctac 114960
ttgatgccac tctcttctat ctttctgtag ctaagccatc cccaagtttg tcgattcacc 115020
ctctttaacc cctgtcgggg tgtccattgt gccccttcac cctgccatct ccctggtgca 115080
ctgttttgca aagttcagca tacatgagcg tcacctggga accttaataa agtgcagatg 115140
ttgattcagc aaatctggga tgccctcggg ctgcatttcc agcaggctcc tggggatgtc 115200
cccgctgctg tgctgcagat gacactctca gtggtgggac tccaggctct gctgtcgcct 115260
cctaggggtt tctccacact ccctggaggc ctaatgggcc cttctccaca tggcagtaag 115320
atctgttttt gtgtttgtgt ttcaagttgg gagaaggaga ttatttaata ctaaaatgtg 115380
caacatggga ttgagaaaac taattattag tcataagttg agtatgcaac attgaaacca 115440
catgctttaa aaaattataa gaaaaaatca tagtatttga aagttacaag ctattatggc 115500
taactccatt tatctcagtt agagaagaag agtcacctgt caccagggca ctgccagaag 115560
ccaggctcat ttccaacagc actgggtgct ccagctttgg ggtgccagct cctcccataa 115620
agcaaacaca tacctaggga tgatatttct ttgcaagggc tctgccctac agcttgtaca 115680
tctcaagaag ttatgtaatt aaactgtctg ttttgagaaa attgtagatt cacacatact 115740
agctgtaaga aatgatgcgg ataaatccag cgtaccagct ttccccacgg agacgtcttg 115800
cagcgtcaca gccaggatga ggcattgacc caggcgaagt ccagagcacc tgtgcgctac 115860
agggcccctt gcactgtgct gtcacagaca cgcccacttc cagatgccat ctaggacccc 115920
ctccaaaaag cagaggcatt cttaaaaaca cacatctgca catgttcctc ttcatttgaa 115980
tctgtcagtg gcttctcagt gcctttcaaa tgaaatctaa agtccttaca agccttgcag 116040
caggaacctc tccatcccac ttcccctcac actctcagct tcatctctgc taggctctgt 116100
tcagccaggc agcctttcac agtccctctc ctcctgccct gccaggaagg tcccctgccc 116160
ccaactcttc cccacatgtg gcggggcccc gcttgtcctt agaagcccag ctgaactgct 116220
tcctgaagga acccctccag aacctctcag accaggtcag gtttctgcac tcttagatca 116280
tccccatggc ataatcacag ttgtgatgtt gtgatgattc agtgaatgtc tgtctcccca 116340
ctggatggta agcttcctga gggcaggaac agcattggtt ccagtcaatg ctatgtccca 116400
ggactgttcg tttttgcaca tactaatcct aaaaggacga tgacaacagc aaccacttac 116460
atgacctaga tgctcttctg ggtgttgtgc aaatattaac aatttaatcc ttgcaacaat 116520
ccacgaggga ggcattcttc tactcccact taacagacaa ggacagtgaa gctagtaaag 116580
agaagtcatt tgcccaaggg gaccccacta ctgttggcag agctgggtgc aaacgcaggc 116640
ttgtgaagcc aggacccatg cattcaaaga ccatgccagg tgccccccact gcacacctca 116700 tccccacata ccagtgaggg ggagagaaat gctcctgcac tgcctctgat taactgcttt 116760
cctagaagtc acacatataa aagggattta attctagtgg gattgaatct caatagtttc 116820
cttattaggt tgatttctgt taatagttta agtactggat atacatgaat tagaaaatct 116880
agattattag caaatgcaaa ctataaagta ttttataaat gttatcttgt ttgtcagggg 116940
atgagtgaga tattcattat acaaaaagta gtgtggattt tgaggtagaa ggtttactaa 117000
ggatcatacc gtagtatgaa atagccacaa acattcagtg aaaccaaaca cccccgctta 117060
acctcaaact aacactaaat aataaggaat agacttgggg gcagtgcaag tgtatttcta 117120
atggtgaaaa ccattcccca gtgaaaacta atgtaccatc tagttaataa gagctcctct 117180
gacccacgca catcaatact tacatcccaa tggtgatgtg acattttggg ttttgtattt 117240
cttttgcaaa ttgagctagc atttttgatg agtggcaggg ctctgctacc caacctttgg 117300
acagtttcca agcataaaat cacaattcca gataattctg tcacaaagat ctgggtctca 117360
ttaggaagga gaggaagctg ggagatgatc cagtccaacc tcccccaaac caaacatcac 117420
ggccttctca gttgtttcac caaccatcta aatgttttag taattctaaa aattgatgcg 117480
ctttttccac gaaaggaagt gttaccacat tttccaagtg ggaggcatct atatccttac 117540
tccttcatcc tctccttccc accccctcac cccccaccac ccacacaaca tctgcaattc 117600
ttaaactaaa gcacaaattg ttacaaaagt taattgcact ttcaaaggaa tgcttgtata 117660
gaaactttct cggcttcaag gaaaaataat acgctttgaa tggctgttca acagcataga 117720
aattagctga gtagaaggca ctcatatagc cattaggacc aatcctttct gccgccaaca 117780
ccccccttat aaagacttga cagtgggcca gaataaacaa cttcaggatg aattcagttg 117840
agacacaaag tacacacttc cagtttttcc cttctctggt tactggcctc aataaccagg 117900
cagtcaactt aaaaagaaaa acaaaagctt gcttcagatt acagattgca gacttcttat 117960
aatatgtcca tttcaccagg ccccgctctc agccccggga aaggccactg gaaaccacct 118020
cacatggtag ggccttgcgg gagccagtaa taaccttatc tccgtcaaca tgttctgtca 118080
gattgaatgg ggcagccaga gaagccagag ttggcacagg aaccaaaaca aaggcttccc 118140
atcctcctgg agtgagcggt tgagcctgga ttggtgctta gacctataat gggtgcaagc 118200
agcgttcatt catagtggct ttctagaccc agggacttgg ccccagccct gctgctccac 118260
tcctcttctt gcttcattac cacgagtctc ctagaccacc gaacgatgcc tgcatttgaa 118320
agacacttct gctgatcaaa gcagctgatg tgtccctttg cggttcattt ctaattgtcc 118380
ccaaggagga gaaattcaaa tagtttatta ctgagagtta aagaaatcca ctgaaatatt 118440
ctttggtcta aaattactgt catggcggag cagcttcacc ttagtcattg cccttaaata 118500
tgaaagctat ttaagaaagt ttgcccttaa atatgaaagc tattttaaaa agtttaatga 118560
aagaagagaa tcacaaaaca ttttcaaaaa gcaaaagaaa acctaagaga aaagttgaaa 118620

-continued gtaggaattt tttaaagaat atacgacgtg tgttctgtga ctcacccctg caagttattt 118680
gtgtgtattc ccttgcatag taattaataa tgaagcaaag catggcaatg atatcttttc 118740
ttgtctagta ttctagaaga ctccatgttt ttggaaaata tcactctagt tagatctcaa 118800
atatattcaa tcagaaaatg ggttttctac aagattctat atctgtagtc aatagcaaat 118860
ataattctat taagctagta ggatgtgata ggaaactaaa acctagggga gaccaaagca 118920
aggaaaaata cttcctcatc caaacttgag agcaatttac cgtcaggcct actattaata 118980
gatggaatac agattccatt ttcattactc aactgccata ttcattatta cactgtacag 119040
aaaagggaat cacatctgtt gaaaacttat atatgatgtt catgcatgca ttccagtaat 119100
tcaacaattt ttatttatct ttttattgct tgctaatttt tcaaaataat aagctaaaga 119160
aaacaaaatg tttgtgctgt tctcagatga catgttatct ctttaaagga caaaatgtgc 119220
tgtgaaataa tagaatgctt tcagcactca agtgtgagtg agtgctcata catgagagaa 119280
agccgtgggg actacagaag ccaagaagca gatctagctg ggaggccttt tgcagaggat 119340
gtagttgtgt ggagaggcca cacacgtgga attcccagga gggctgtgga ggcggggaat 119400
ctgcaggaaa gcactggggt gagaaacgtg atgagaaaca attattgtct taaaatatct 119460
gcagggctgt aaggtagaga agcaatacgt tgcatctgtg ttaagtcaaa caaaattatc 119520
aagggactgg tttcagctta acataaggaa caattatgtg atagggttgt caataacaag 119580
agtagactgc ttcttcacac actcctagtc actcagaatg gtccaggagg agtggacaac 119640
catttggtag agtatgggaa ggcaggggcc ctgggtggga gtggtgaggg tagggagtga 119700
gtatcccaat ctagaagtaa attgtgccca gcacggagct gcaacactgc cctgcacaca 119760
aacacacaca aataacaatc cccagcccct gcatttccct ctccggtttc aggaccttgt 119820
atcttacttc aattccttta tttagctgat gatgaaatag gaagagctta gcactaagaa 119880
aatccttttg gagtttggcc ttgggggaaa atgaatcact ccaaccaggt ctgtcttcta 119940
gaaagtatag gatgaaaggg ctcctcatca catacttcct gacctcctgc taggcctttc 120000
cctaaaacag gggctggcaa agcacaacct gtgggtcacg cctagcctgc cacctgtttt 120060
tgcaaataaa gttttattgg agcatgacta tatgtatttg cttacagtct gtggctgcgt 120120
tcacactatc ccagcagagt tgaataattg ggacagggac catatgatgg gtgaagctga 120180
aaacatttac tctctggctg tattcagagg aggtttactg agcccttctc tgagacatgg 120240
caagcgctgc ttcaggctca tgcttcacta gattcaggcc tggggcagta aagagccagc 120300
tcaggatagc actcccgact cactcatttt ttcaggcagg ggagccatct aatgtcaagt 120360
gcctacgtgc aggaactggt ctgttaatta gcagctctcc tcatggaagg gataatatat 120420
tctagaaaca ggagtgcggc cctattgcaa gaatgtcctg agccaaaatt aagattcttc 120480
tatggcagaa acttggctgg ggcttctcct gagttaactt ggtagttgtt agtgattttt 120540
gagtcagttt ttccttgtca acgaccccag gaatgagttt gggattacag ggtagccagg 120600
gaaagggaaa gcttcacgcc cgcccccggg acaaggtctg tcttcacact gctacatccc 120660
ttcacccact ttaaaatgaa acttaaaagg aggatttcag ttgagtagga agtgagaaga 120720
gggctcattt taaaacaagc gttaaatgaa aacccacaca cactcagagc acacaaatcc 120780
aaccacgctt acaaaaccat cacagagggt caggcgaggc ccttttctaa atgaaaaaga 120840
acaggggtgg agactgttct gagagcatgc tgggttccct gaagggaatt ctcagctgta 120900
tgtgccccgc acaggatccc tgctagacac aaggccagct gccttccttt caagccgcag 120960
acgcatccct gtgtccaggc gggctggtca gctgcggtca gcaccagctt ccccgctcca 121020

```
tggtgaggtc atcacaacat gtgagcagga gggcaggccg gcaacctctg agtgcttaga 121080
gaaagggacg ggattcctcc tgtgcaaccc ctctagtctc actcagactc aagtctgact 121140
aaggggccag gtgctttgac cagggactct cccctctcac ttccctccca ggagtcacag 121200
gtacatgagt ccttgtttta caaatgaaga aaacagaccc aacatgatta agatgttgcc 121260
ttcatagggg tggcaccagg attccaaacc atggactcca ctgagcccag tgcccactga 121320
catgtgccag taacagtgca gctgcctgtg gttctgtcga ctaaactgcc ggcagaggct 121380
ggctttccac cttctttttt ttttttttcac tcttcaaaca ctttatgaca tgaacataaa 121440
ctactggctg catcgttctg ctgacaacat gacatgtttc tataacttga aaaaagcaag 121500
cagtggactg ctcattggta aaattgagtc agtaatcttt taggaaggtt atttttcttc 121560
cttttactgc ttctcatctg ttccccgcag taaagaggac aagatgacga cgactcaggg 121620
aacacctcca gcctgaagca gcaccatgcg agcttagacc ttagggtcgg cttagaaacc 121680
acaggcgggg cggcttgggc ccctcggaca ctccctctcg aagctgcttc tccccaagct 121740
accccaaagg cactgagcgc cctctgcccc ccagcaattc aattcactgg ctgtcctgct 121800
cctgtcagta ctgagagttg catgtttgac cctcggggga aaagtccaga ggccctgggg 121860
tgtccagcat gctctgaggt ccctgctgct gacccccttgc gctgtcagca ttcagagaca 121920
ttcacacagc acagcctccc aggctaacag ctgtcatgga acagtggagc agctagacgt 121980
ggccattctg tggcccagtg ctgcagaggt caaagggaca agcgcaggga gcatctttgc 122040
tttcagaaaa aaaaaaaaaa aaaagaagca cactggtgca ctgacctgct cctggtgtct 122100
ttgtgattgc tcttttcttt cgatttttgg ttgtcttttt tttttgaaa gaggggcttt 122160
tatgcttttt tcctaatgtt catgggtaaa ccaatgtaaa tgtgtgtatg tttatagaga 122220
tggctttaaa tcgcaattct gcagtagaga ttgatttttt aaaaaaacatg ggtaaaaatt 122280
gaagaaaaat tttaaaagaa catttaaacc atcttgggct aggggtggat atgcaccacc 122340
ccacggaagc caaacaaaat ctctctgcag ataaacattt gcaaaaagaa tttccaatcc 122400
caatttttga gtcagagatc ttttatttcc ttgcaaatta catatctgtt tcaggatttt 122460
tgactataag aagaatgaat gaagatgtgt ttcttacaga taactatgaa caaaccagga 122520
aggataataa cttgtatccc ccaattcgaa tccagaggat gggaaggcat aaaaaaaaga 122580
aatggaagaa actttatttt tagtggtaaa tggtgggact atgtatttta cgtatggtga 122640
agtcaccaag cccaacactt ggcacttgta ggcaaggtag tcttctaatc tgaatgtgaa 122700
gtattatgtt ttcatttgct tggtaatgag gaatattggt gctttcgtcc cagttctcga 122760
gctgactgac ttctctttct gacgtgtgtt cctttagcac acctctacac tgcatggctc 122820
tgagatgtcc tgtgactgtt tcatgtgtaa agttgcctcc ccaaaggact cacatattcc 122880
ttcagggcag tgagtacttc tgattcatcc ttagcagcta ccttcgcgct actttactag 122940
atatgttgta gttgaattaa tgaacaaaag aacaagcaac tttggtgcct ggtgtgcatc 123000
tcagagcagg gtggagtgag cctggccaaa gggtcatcat gcaacctctg tggctgactc 123060
catctggcca cggagcttct cagccatgct tggtattcac atgacttcta gggcgacagc 123120
tcaaccagca aataaacagc ttcatatggg aaatattact cagcctttgt catcaaggag 123180
tgagtcacgg gcctgaactg aatagaagat agaggagaaa aggtgtgtgg actgggtgag 123240
acagcgccca gcgaggtgaa ctcccggcag ccctgcctgt ctttacctgc acatcacctt 123300
gctagggtgc cttcggttgt gagggcctgt ctaggaagag aagagttgca ccctggcagg 123360
```

cagcactgag ctgtctcatg caaagctgag gaagaaagag tgagctgccc agtgagcctg 123420
ctggggtggt ggaggctggg ctgggctgtg cagtctgcag cccccagcag cccttggcac 123480
ctttctactg cctggtgctc accagctctc cagtaacaaa gagggacgtg aagtcagagg 123540
ggaagggagg tagcacaggg cagtcttgac tttgaacaaa gagctggctt cctgaagtca 123600
gctggccggg ttttgaagcc gattttccag cagtgatctt tgatgccaac cccatttagg 123660
aattctgtat ctccccctac cttctaccag atgtctctga gctcaccttt ggtgataatc 123720
atgcaatctc cgtcatcccc acgtccacac tgccccattc tgtcccaccc cgggttctgt 123780
ggtgctgtcg gctccccagc gagccaggaa gggagaggcc agctctgctg gggctcctgc 123840
cgccctggct ctgcactgcc cttctctggc aggtctgagg cgccactgga ggagccacac 123900
ggccctgaag cagcaaggca gatgccctgg acacagtgga ggcacagagt gcaagcaccg 123960
gcctggccca cagacttttg gaggggaagt ggtattattc agttcaaaag tatgcctgtg 124020
tgtaaagaga gagcccctga acatgagtaa gcaaaagtct cagcgcagag attagacaag 124080
tagaatgctg gcccgagagg aggcgtttac tcaccctctg tctaggaagg aaagccaggc 124140
ccagcacgct cactgctatc tatcctctca cacagaggga ttttgaatcg aagccagcat 124200
cctgtccttt ctccaatgtc ccctgctcag gagtcaggac tcagcaaggc ccaccccagc 124260
cacacacaga tacagttcca ggactcagaa ctcagcgagg cccaccccag ccacatgcag 124320
gtccagttcc aggattcagg acacagtgag gcccacccga gccacatcca ggtccagttc 124380
caggactcag gattcagtga ggcccacccc agccacacac aggtccagtt ccaggactca 124440
ggactcagcg aggcccaccc cagccacatg caggtccagt tccaggattc aggacacagt 124500
gaggcccacc ccagccatat ccaggttcag ttccaggtaa atcatctgcc ttcctccgtc 124560
caaaagcctt gtttcctgtg tgtccttgtg tttaaaatgg aaacgttatg agaaactgcc 124620
tgccagggca aagggtgctg cccggcacac agtagggact caaaatgaaa ctattgtatt 124680
gaatacataa cagatcaacg ggtattgctt tctgaaatct tttttagccc aattttgttt 124740
cttatagtcc aataacaggt caaattcatt tctgatttac tagccattca gttgcccata 124800
aaaaatggaa agtgatttaa gattattagt ttaaaaacca atgaaggtaa aacagttatc 124860
attgaaggca cataggcaga aatagattgc aatagttgct gccatgtgaa gcctcagtgt 124920
catgctccat atttagagag atctatgatt tctgaggccc tttcatgtcc atgatctcag 124980
tactgctcac aactgccctg tgaaattcgc cgagctggcc ccatgtcaat cagagtacac 125040
tgagcactga gacccagcat gttgagataa ctggctagag atcatcccat aatggtacca 125100
tcacaatctt cacactgtag aagtttgatg atgtcactgg aagcatattc cacagtccct 125160
tgtgaactgg ccttcctgtg atcagaagca tcagtgaact cccaagaggg tgggaactcc 125220
caagaggtat tctcactcta cttagtgtat attttacaaa tcacaagctt ggctttggat 125280
tcttttaatg gctagaagga gaatcatggg gttggaagtc caccagtttg ggtattctgt 125340
tccctaactc aaaataaaga gatgttattt tcaagtcttc tgcttgttaa cttaattaga 125400
gatacatgag tttgcagctg tgctgggcat gccgcagctt ggcatgttta gtccagaagg 125460
catattataa tgtacatgga agattgtcag aaattcaaaa ggactttttg agtatcacat 125520
gtgtattttc aagttccaat atagattcac attcagtttg acaggtatct ttggatgcct 125580
atcagttaag aactatttat tagttgtgga ataaaatagg gtaaaataag gaacaactga 125640
ggaaaaaaca taaaatttgc tttgtgaata aaagttgtct tcaaaattat gactttttcc 125700
atcccacaaa agttttgatt aaacccacaa tgaaaattta aataagtgta tttactttgg 125760

```
tttaaccact tatttcatta tgactcacaa ctataggttt tctagtttcc attattacaa 125820
actattgtgt ggtttaaatc aatttcatag actagtctag ttctatagtc acaatttata 125880
aaattttttt atgtggtaaa ttgagtgtct tcatagatgt acatgattat ttctcaattt 125940
ttaaggaatg tatttttttaa gatagccttc tttagccttc tttaacactg atttttgtaa 126000
atttttttaca gattttttta aatttttggt aatttttttag cataaagtaa tacatggtca 126060
ctatggaaaa cataaaaaaca caaaaactat gaagagtaaa taagaaaaac acccagaaat 126120
ttaccattca gaaaaggtca ttgttaacaa cacggtgtat cttcctcctg tcatgcttcc 126180
gtgcatttga gcacatttga gatgtgtata catgttcact ttgagatttt agtatagcaa 126240
aagaaatgac cggtcctgat tcaatgaaac ctctggcaaa ctcgctatat tttccttaca 126300
tatttttaag ttcatcctat aaatgaacta tccattcatc ttatttgaga ttttcttaaa 126360
tctttcagca agaaagcggg aaaaaaatcc tcctctggcc tttaaagcct aattaaatat 126420
atgactaagc tagaaatatt ttataatgac caaccagaaa gtggcaagga ctgtcactct 126480
tcccatacag cccacctcct cctctatctc cctcaggcac acggaaacga gaaaggcaga 126540
gaaacccagg acaagtcatc caagactttg gtcacatggc catccattgc tttcacaaca 126600
aaaatataaa tccaacatgt gtgtgtgcat ttcataccag taggtccaat aagctatcta 126660
tatatacaca tatgtgtaca cacacacaca cacatcctta cagacactcc ccagcttact 126720
acagtttgac ttaagatttt ttgactttac gatggtgtga aagcaatgca cattcaatgg 126780
aaaccatact tctaatgttg aatttttttat cttttcttgg gttagttgat gtctgatatg 126840
ttactttctt gcgatgccag gcaatggctg ggagccagag ctcccagtca gccatgcaat 126900
caagaggcta aacagctgat actatacagt ggactgtgtc accagcattt tggggatatt 126960
gtgttttgtg tttttgaatc ctatcatgtc tacaaaatgc cattttcgac tgctattttc 127020
aatttagggt gggtttatca ggacataacc ctatggaaag ttgaggacca tctgtatatc 127080
tggtagggaa agatggataa caaattcata ggcaaataat aatttcatga ttattattaa 127140
gttattccta cttaataata agtagtgatc actgccaggg agcagagaat gcaggataat 127200
gtgacagatg taatggtggg tacttaagct aatgtagttg cagaacaggc ttttctagag 127260
ggtaggcctt taagcgtacc tcgaagatgc aaaggaagca aagatgcgaa gatctgggct 127320
ggggatggaa gcagagacaa cttggaggcc aaggggagag actgacaaca gcccagctca 127380
tacctcagca gcctttaatg catagctaag aaaacaacaa attaaaacaa ttatagttta 127440
cttagacgat tctaagtgtc taagtggatt tgggcaaatc tggagaaact tgttctaata 127500
ctgtgtctta ataagtaata tagatttgcc caggcttgtg ggcagagtgg tatacacccc 127560
ataatagcag aggaaggcca cagggcctac cctacaaaac cagaggcatt taaaaactta 127620
aaggaggcag attgctttta ttttcagtta aaataaagtg aggagtttct caagaaaaat 127680
aataacgaga ccaccggccc gccctagatg tccaacaaga atgcacagat aacttcgtat 127740
atccactttc ctgaacctgc ccctgacagc caagtggagc acaacaacag agatgaacct 127800
caaaactact gtgctgtgac ataaggcttg ctcaagagga cagtgtggtg tgagtccatc 127860
tatgttctaa agcaagcaaa gctattctgt agtgaaaatg gatcaggaca gcagttgcct 127920
ctggtgtatg ggggcaggga tcgactggga ggggcatgag ggatgacagt tagggtttcg 127980
atcatgacag gaattcagat tactccagca tgtgcatttg ttaaagctca tcaaatgcta 128040
cacttaagat taatcctctc acagtttgtg gatgttacct taaaaacaac aatgatgact 128100
```

```
gcaaactaat attgaactct ggttagtgat ataccaatgt gaagtatagt gatatctcta 128160
ctttacttta aaatgcatcc aaaggcagac tagaggacca tatctgacag acagaaaaat 128220
agatatgtga taaggtgaat gtagtaaaat gctaacataa ggatgtttgc ggtacaattc 128280
tttcagcttt tctatacatt tataaatcat aataaaattt taggacaaaa agttagtgct 128340
ttgaagtcct aagtcatagg gcctgctgct cttgatgcag tagaatttgt cttcagattt 128400
gcaaagggta aggcaaacca ctagcatttt gtatggaact tgatgcaaat acttttaatt 128460
gtctggtttt caaatgtata gacttaaagt aatatcaact ctttctttga atcaactact 128520
gaaataccta gtcttaaata aatattttta tgtaatcctt aaagtactat gtattcattt 128580
ttctttcttc tttcttttct ggtttgataa atattctata aagtaactgt gtttaatggc 128640
caacatttga gtaagtccat atgcagatcc aaacatctca gtttagacaa taacttaaga 128700
caatatagag tggctgacat cccctaacgt gggtccagat gcatgttatg ttatgtttct 128760
gttgcattct caatagttaa ctttaataaa agaaagtcaa aagcttatat attttttcaa 128820
tcttcaaaac atttctggga ggttgtctta gttaatttta tgttgctata cccatatcac 128880
agactgggta atttataaag aaaataaatg tatttggctc atggttctgg tggctgggaa 128940
gtccaagagc atggcattgg catctgcttg gcagctggtg agggccttca tgctgtgtca 129000
atctatggtg gaaggtcaag agagcatgca tgtgaggtgg tggggaagag aaaaagcggg 129060
tttaactcat ccttttatca gggactcact cccgtgatag ctaacccatt cttacatgaa 129120
tggcattaat ccattcctta gggcacagct ctcatgacct aattataata cctcttaaag 129180
tttccacctc tcaacactgt tgcattggtg attaagtttc caataaacgc actttggaaa 129240
acacattcaa accacagcag agatcaacgt tattgtcacc attttcatat ttgaggaaag 129300
catggcacag agagcttgga gaagtacttc aaggtcaccc aatgaggaag tggctaaaca 129360
aaaaccttat cttaaattaa ttaaaaacct cttgctcttt gcagttttgt cttaaatcta 129420
cctaatttgt gactgtaatt tttaagtaat ttactcatat aagtggtctc acattaaatt 129480
ttctcattgc tttatatttc taacatgaga tatttggtat aaggatggaa ccaagatcat 129540
accttgtttt aattagaaaa cctagaccaa gtcattgtga tcctcatcct agatttcagt 129600
taaatgctgc tgtctccttt tgggtatgtg acaggggaaa gcctcagaag aaacaacctt 129660
atgtgttttc ttttgatact ttagtaatta acccaggata gtattcaaga ttgacatgcc 129720
ttatattgaa tcaaatagca tatcaactgc cttcttattc tcaagtatag acatgttggg 129780
taattgggca tttaagtttc tttgcaattt tttccattat taacaaaatt aatgagcaac 129840
attctgcata aggtctgttt cctcagaata cgtttcccaa agtggaatca tcatgacgta 129900
gaatttaagc atacttactt gtttaaacaa attgtccagt tgcttcccaa aatgttttgt 129960
gaattaagat ttacatcaag aatatgtaat gttgttactg tctcccaaat acaggatctt 130020
tttctgaata taaaagttat acatgctaat tgtagacaat gaagggtcat tatcctcata 130080
gataatgaag tgcttctaat acttgtgctt ttattcattt attcaaaaag tgctaaataa 130140
gccctgaagg ggcttttggg gggtcatttg gggcttattt agcacttttt gaataaataa 130200
ataaaagcac aagtacagtt tttttaaaat actgttttct ataatagatt aatcttaaat 130260
ggcatgtttt cctttatttt actgacaaaa gttacttact ctgtgattga ataataaaaa 130320
ttctttggtt cagctgagag aaacttgcaa gctgacgtcc ttgattattt aaaatgaaag 130380
cagctgcctg ttttcatctc tctgcatcct gaggaaactc ttctgcaacg tgttccagcc 130440
ctaggttcta gctgaccctg ttcatctgtt tggcacgagg ggcccaacta acacttgcgg 130500
```

```
ctacctggac gacagccaat ctagttggaa tgagagttag aggccatagt ctgtcagctg 130560
ggaaagcagc ttttattcca aggtgtgcca accgaaaggc cacatgttat tgtcacaacc 130620
tggtacctac atcagtgctg acatctttaa gaaccttaga attgggaaat cagtttagcc 130680
ctatctgcat gtgtagccga caaccacaca attgttccaa cttgaggttg cattcagagc 130740
aacctcattt cccccatact cctgaggaaa agcagaccag agacgctggg tcaatccaga 130800
gttatggttg gaaaaatgat ggaataattc tgcccctggt gataggagag agggactcca 130860
tcttgtcaac tgtcatggtt cccatgtgaa agctatcatt atcactgaaa ttgaatgaga 130920
acacagaagg gaagaacagg gaaatcccca cagagttaaa gaggatgtga agattgcttc 130980
atgtttaatg tttgtgtaag tgctttgggt tggttatgtg ctgtctgaac atgtgctcat 131040
ttccatggct cattgagagg gcagacagtc caatgatact ctttagaatc attcccatgg 131100
ggaaggaaca aagaagcctg taaaatagaa atgcacatgt aaaaagcatt gaagaaagtg 131160
ccagtgtatt gattttggcc atggtttgtg ctctaccacc tggttactgt gattgcagaa 131220
gtgcctttgc agatgaggaa gaacctggcc aaggctcaat ccaacatcca aagccagagg 131280
ccatatttct tcactcttaa gataatttgg gttcaaatta tagtcccttt acacactctc 131340
tgcctcaaaa ggcccaagac tctcttttgt tatgcttgcc taaacatgcc tttcaaagaa 131400
ctagttctgt aaatacaact ttattataaa cctctccttt gcttttaaaa atggatcacc 131460
acgtccattt ctatggtcca actttgtccc ttaatttaaa attttttctt ggattaagtt 131520
tgatgccttg aaacattagg aactcaagca tacaagattg tatgctggtg gtgagggaag 131580
taactgtgcc tccgcctgtg ctgggtggat caacatggag tgtggacgag catagggatg 131640
tgtgggtttc tcactagctg agagtgtttt taaatgttgt attttgatgt ttgttatttt 131700
ctgaatattc tacagttaga cctttgattt attctttgat gcattcattt gaataatatt 131760
tttaatctcc agccagttag gtttttaatt tacacttttg tccctgattt taggtgtagt 131820
gttgtgtaca ctactgccca gtgtatgtta tgtttgtaaa cattcattgc acgcacaaca 131880
atgtgactca caatattttt gagaagtaaa aagttcatta tatagttatt aactcaaccc 131940
tacagttata ttcgtgaaat accttgtgaa atttattttt tgcctactgg agctcttaca 132000
ggttaatcct gtcttcaaga ttttcataga attttcatct accacccacc cctttaaatt 132060
tcaacatttt tttattttgg cattttaatg caattcaatg cattataggg acaagctatc 132120
tcttattatg aattgcacct tatataaact taaagatctt ttatcacaaa tttctttgct 132180
gtgtccttta gtgagaattt gtattatcag tcactaaagc tcactaagtt agtaagcttt 132240
gcgcccagat gacctgggca ggaatgggtg agtctctgtg tggagagagt gaagaaactg 132300
ctacccttaa tacctggacc ttgagggatt gttttatttt agtttttctg catttctcag 132360
tatttcatgt gatatctgtc tttttcttcc agtttgccaa ggcacgagta acaagctcac 132420
gcagttgggc acttttgaag atcattttct cagcctccag aggatgttca ataactgtga 132480
ggtggtcctt gggaatttgg aaattaccta tgtgcagagg aattatgatc tttccttctt 132540
aaaggttggt gactttgatt ttcctacaca aataaaattg gagaaaatct aagtggagaa 132600
aggcctgggc agaattccac ttgaagtgtg tttatttttg ctatggcaat gacaagtctt 132660
acagagctac aaacgagagt tttatgagaa agccatttta ccagctaatg tcaagtaata 132720
actagaaaag gatatcaaat agaaacaggc taatctggag ttccatgtca tcatagacac 132780
tgacgtttat ccctgaccat tacctcagtc atgatgtgct gccatactcg ctcttaaaaa 132840
```

```
cttttttttaa aagccctgct ttgcaccatt tgcctattcc cttagtgtaa atactcctac 132900
tatagctgat ttcaaggtac caagtttcac tcagctggtc acagaattct tatttcacga 132960
taggcgctaa tgaccccata ggagccagct ctgaaggctt cagagtttca ctgaattttg 133020
gatggggttt acttagcctt cttctgtttt tcttttacct ttccttttta aataagaaat 133080
aatgcaagac agatacaaag taattctttt taatttccat tttcactgga gagtgttgaa 133140
ccccgtgagg catgagagca cagtgttcca gaacaatgct tactgctcat tatcacaggg 133200
gtcaaaggct aacgtgcagg gattgttgca gatcgtggac atgctgcctc ctgtgtccat 133260
gactgcaatc gtctacctat tttacagttg ttgagcactc gtgtgcatta gggttcaact 133320
gggcgtccta gggctccctg gacccatttt agaccttgag ttcttgagtt cctcaaaaga 133380
gaaatcacgc atttatgttt tctcttctta gaccatccag gaggtggctg gttatgtcct 133440
cattgccctc aacacagtgg agcgaattcc tttggaaaac ctgcagatca tcagaggaaa 133500
tatgtactac gaaaattcct atgccttagc agtcttatct aactatgatg caaataaaac 133560
cggactgaag gagctgccca tgagaaattt acagggtgag aggctgggat gccaaggctg 133620
ggggttcata aatgcagaca gcagttccga tggctcccag cgagcttgtc actcaattcc 133680
acctcggaga aggcttttat ttttacccag tacacgtgca ctgagtgccg gctgtgtgta 133740
agatactgca ggggaagtta ctgagaagat ggcagatact ggaatgggaa gatttaagcg 133800
gggtaccagt gtttacatgg acatgaaaaa atactgagag atagtaagaa atcgtaaaga 133860
ttctgagtaa aagagagtat gaccaaacaa gctgagcagg aatcgtgaat ctatgtgtgt 133920
aggcagtgaa taaactgcca gtcttattac ctggacctca aggataaaag acatacagta 133980
aaaatcaacc cacattgagg acagtttcga gagtcgcgct gctacacaga aagccctgtg 134040
taagttaagg atagagaatg aggtgttcta gaactttgaa tttttgtgag caggactcgt 134100
gaggttcctg tgagaggaaa caatgaagga tgatagaaaa gaagggaaat tgattttaaa 134160
aaactggaga tagcagtgat tgtgcctcac tgtgcagtgg gtttggggcc aggaatgtta 134220
aattggtaac ttcatttaac gcccacaacc tttcttcaaa gtaggcactg tacagatgcc 134280
ccttgactta tgatggcatc ctatctggct ggaccccgcc gagggtgaag gcgtcattag 134340
gtcggatttc agggctaatt gaatgtatat tgccttcaca ccatggcaaa gtcgaaaatc 134400
tgtgttaaat catgctaagc cggggactgg ctgtgctctg ccatcgtaca aataaataaa 134460
tggaagtcaa gtaactccct tgagggcccc agctagtgaa tggagaggcc agctatggcc 134520
accactctct gccccagggc gctcaacgcc cctcctgtgc catgcagttc tgacagggag 134580
gcagtgctgg taggaaaggg gtgtgatgaa aggggtgccc agcagaggga gtcatatccg 134640
gagtgacagg agcccaacag gggtgcagcg ctggaaccca agccagcacc tctggtcatg 134700
gctcctcagt tcaccgccta taaaattgtg tggttccccc acaccccttg ctgctcagag 134760
cagccgcgca catgcttgtg ctgtgcgtgc ctcctgtgag atggcctggt acaccggttc 134820
ctacagtgcg cctcacacgc tgtctcggag ggaggcagcc tgtgcgggtg cctggacctc 134880
cgagccagac cctctgggtt cctgcctggc cccgtccctc agcagccaga tggctcggga 134940
gcacattctc caatccctcc gtgtctctgt ttcgtcatct tcaaaaatgt ggatggcata 135000
gctgctaaaa aatggtgaca tacttcctag gtggtgcaga aaattaagtg actgtaggaa 135060
caggcctcag cagctccttc cacttccttg gtatgattgt tttttaaacc aaggctggga 135120
ttgtatagat gcagattagt taatgtgata ccattaatag ctaacctagt gcctgctgca 135180
gggtgagcct cccctaagcc accgggaagc ggctcctgca gcctccctca cgtgtgctgg 135240
```

ccctcctctg gcagtcattg cctgtggtgt gctgaaggcc cagctctgac tgtgcctctg 135300
tgctctcctc gccccgcccc ctgctctctc tcaggtcttt ggtctgttgt ccgagctgcc 135360
acagcagcct ggacatccct gttggtgttt ccagccctgt cctctcctga gttccatcca 135420
cctgtgcatg gctttttcat gagtgttttc acggatggtt ctgctgtcat ctccaacctg 135480
ataaacaaag caccacgatt cagcccttat gaccccaagc ttccttcctc agttccttgc 135540
ttctgtgcat ccactgaaga agcctgttcc actgtttccc tgcactgggt ctcctgtctg 135600
caggaagcct tcagccctca cttccacact cctctaagat gtgtgcctgt gcccttctgg 135660
ggaagctcat tttcctagca gcctccagga tcttcagggg tgaatccctc ctttcccacg 135720
ttggtactct gtacacacaa catgcccatt ccctgcctgg ggagctgggc attgcttcat 135780
gaatcagagg tcaatttttt ctctattaaa gtcacagatg ctcattgcac cattgtgaga 135840
atgaatgaag atagtgctta taaatcagcc agcaaggtac ccagcctcac tgtgtcaggg 135900
tctccctggg catgaggtgg ttagagtgtg tgacatgtct gtccccaagc ctgtcagctc 135960
ccagatcgaa gccagtggat ctcattcatc ctcgcagcgc ccacagcact tgcacagggt 136020
tttgtacaca taagtcattc tgtcaatgtt catgtttaat gtcatcagtg gaacactccc 136080
actttgtaaa gacttgaatg tgttcatccc tgacttttcc acatcttgtt agttcttctt 136140
tggaaacagc tgtacagttt caccatcctg tgcatccctg gagtctacct gtctctgtca 136200
tacattcaga ttcttcttgt ttcgtgtcac tctcatatcc ttttctctaa tgaaaagctc 136260
cgcctgggca tgcaaggtgg agccctggat gccagcccct cacctggcat ccagggctgt 136320
agcactcagg aactgcctcc ctgccctgcc taccccctac atcatgcgac cattccagtc 136380
cagccaatca gccccttggg acccagctta ccacatgcat atcatttatg ctgtgaccac 136440
tgactaaacc attctcttcc ttcctcccca tatttctaaa tttctaatca ttgctcaaag 136500
cccaattcag agaaaaccct agctcctcca tggcaccatc attaacaatt ttatctggcc 136560
gccccccggg aagttcactg ggctaattgc gggactcttg ttcgcaccat ggcatctctt 136620
tagcagaaca taaatgcgaa gagcacatgc atccttcatg ggaatttaaa ggagctggaa 136680
agagtgctca ccgcagttcc attctcccgc agaaatcctg catggcgccg tgcggttcag 136740
caacaaccct gccctgtgca acgtggagag catccagtgg cgggacatag tcagcagtga 136800
ctttctcagc aacatgtcga tggacttcca gaaccacctg ggcagctgta agtgtcgcat 136860
acacactatc tctgcctcca gctcctatgg gggacagctc tacagcactg gggcagggga 136920
gagaagccat gtttagtaag tcacattaat cagaaacaaa aagtagtaag caaaatatct 136980
gaccactaga aaagcatgta tttaccacgg acatagagat cgtttttttg tggcgggtgg 137040
cagcccagct ggttggcagt gcaggccacc ggaggcagat cccctgcagg gacagcagag 137100
cacttgtgtc ctgagaagag ctgctgttca tggggctggc agcaccaggg cctctcctag 137160
cctgccctgc tgacactggc cagactccta catgcttctg agtctccaga ggctacccgg 137220
ccctcctgaa gcaccagggc tgaatccacc cccagctgag ggcatgaaca ctgccacatg 137280
gagtcacaca cacagctggg cactgccatg gagaggaagt ctgtccatgt ttccttgaat 137340
actggtggcc tggtccctgt cccattcccc agtgaggcag cctgtgggga agcctggcag 137400
ggaaccaggc gcaggtcagc gtggcgccct gactcaggcc agcactgatg gggactctg 137460
agacgcaagc tcacactcac ccagctcccc tgggctgcgc ccgttcctga tcgcttggac 137520
tttctgttct ttagagtaag aagtgatcac catttcctgc ttctttgttt ctccacaact 137580
gtgcagtgga tgcctgtttg ttttctgccc tcagaacaaa aaaaaaaaaa aatagagctg 137640
acgtgaatct tcaaaatcat caactacagg gctttggatt tttgtgtatt tgttttattt 137700
tcattttatg gatggattgt gatgaaatgc ccgtaataca agattttcca tcttaaccat 137760
tgtaagttac aatgtcagtg gcattataca tccacatggg tgtgtggcca tcaccaccgt 137820
ccacacacag aactctttta tcttgcaaag ctgaaactct acccattaga cagtaactct 137880
ctgctctccc ttccttccca gcctctggcc ctggcaggca acagtccact tgatgtctct 137940
atgaatttga ctgctctggg gctctcatac aggtggaatc atgtagtatc tgtccttttg 138000
tgtctggctt atttcaccta gcaaaatgtc ccgaaggttt atccatgctg tagcacgtgt 138060
taagaatgtc cttcctcttc atggctgaat aatattccat tgtatgttga cactacattt 138120
tgtttgtcca ttcacctatc tacagacact ggggttgctt ccatcttttg actgtttgaa 138180
taatgctgct gtgaacatgg gtattgaggc tctttgtttt atagacatat tattccacca 138240
gatacccatc ctgacaccta ctatgtttgc aagaaactga aagctttatt ttacattgca 138300
aaatttcata ttatgagatc aaggttagca tttcctcagc tgtctggtgg acaatgggga 138360
ggttaaactg tgcacatttt attttttttt aatgaacctg gaacggttat ggggccagtg 138420
tttgccatgg atcaggtcag gcagcccaca atggcaggtc tccatgttct gtacaacaac 138480
tgtgggaaag acccacagag aaagtgctgg aaaggggaat gatgggtagg ttcatgcagt 138540
aaaaagattc aaatactaca gggcattgaa ctataggcca atatagcatt gctttaagaa 138600
taaacaaaaa ataagacagt aagaataagc ctagcaaaat caaaagtcta taaagaactg 138660
acatttcaag ccaataagag aataattcct tattcaataa attgtctgga atgacttaac 138720
tattaggggt gaaaatatca aagtgagaga actataaagg gtttttaaaa aggaattagg 138780
tatgttgggt tagtcgcatt ggagagtgca aattcaccat cgacctgata cctgaaattt 138840
cctccttacc atctagaggc aagttgggaa tgctgccagg ctcctgtggt aaaggaagct 138900
cctctcttga ctggtgcttt atggctacac gttcctgctc agaatggatc tcatttagtc 138960
ttcaccaaaa aaaaaaatct catgagatga tttaagtgtt ttatggacaa gatgtctaaa 139020
actcagaaaa atttcacagt gtgcctagct tttatgttta tgttgaagtt gggcattaga 139080
agttagaatg aatgggttta cttcagagaa aattaaatcc atcacccact ccttgtacta 139140
tgaattccaa atacatatta aatacatata ataaaatatt taatatatat gtaagtgcca 139200
gaaggaaaca taaatatgaa tattttgtaa tatcaagttg aagaaaagcc aaaatctgac 139260
atcataaaag aaaactttca agtaaaatat gttaatggct accaggaaaa tattgtgcaa 139320
tgtctgattg ccatgaagag ggttaatatc cttgctatat cactctgtga agtcatcttt 139380
aaaagactaa gaaaaagatg aatctcttaa taaaaacctg gcccagaaca tgagcagcct 139440
ctctctctca ctctcactgt ctctctttct gtcacacaca cacacgcaca catacacaca 139500
cacacacaaa tatggccaag aaataaagta aaatgttatt tctaatgtaa taagtaggtc 139560
aaaatagaaa aagaaagcat cacaccttcc tttgcaaagt atttgggttc cttttgcttt 139620
taaacacctg ggtcagctgg ggtgtcgaga aacagaaatt ctcacgttct gcttgtgggc 139680
atatatgtta ataaaaccaa gcttggcaat atgcctgcaa tatgtatcta aagcttcaaa 139740
gtatgtatag ctttgaccaa tcaatatcac atttcggaat aagagaaaaa gaaataatga 139800
aagtgaaaat cataagagat gtagaaacat attcttatac aagaattcct tgcagcctta 139860
tttataataa attttgtgaa caaattatat atctaaaaat aagagattgg ttgaaaaaat 139920
tatgcagcag ccatgctatt gataatcatg ttagatagaa gcatatttaa aggcatggaa 139980
aaattgccat gttttatatg ggtttttaag gttataacac aatgtatagt gggattccaa 140040
ttcctgtata tacatagact tatatgtcta tattgattaa ctctggatga gtctcatgtc 140100
ttctttttgc tttcttctat tatccatatt ttatacgatg tgcctgcatt tctttttttgt 140160 aacagatggt caatactaga atcataaaca gatcttgttt gtttattggc aaatgtttcc 140220
cgttagaaaa agatgcattt ttcttttaaa tatttttatt ttatacaatg attacaagct 140280
tataatagaa atttgaaaat tatatgtgag tacagggtaa aaagttgaaa gaatgggatt 140340
gcacgctaca gatctagctg cttttagcac gcctgcgtag gaccttgctt tctctagacc 140400
tctgttgcag tctctctgcc tacctcctca caacgtccat cccccgcggt cactgtcgtg 140460
atgccagcct ccccggcctt catgtctcta aggagcacca gcgcggcaat tagcgcccctt 140520 tgccttggtg gtattctggc ttcacagtca catgggagat caatcgtcag cttttctgtt 140580
tgaaatctaa attcttcctg actgcagggg acctcgggac ccatgaacac ctctagttta 140640
ctatgtcttc acagtaaaag atatctgcat gactggactc tttaacaaat ttggtggtta 140700
acctactctt tctatataga tatagcactt cgaccttcag acttctcaat actgataaaa 140760
agaaaacacg acagatgaca ggaaaacctt tgcagctata atttgtaatc ggccaattat 140820
aaaaactgca aaaattgacc agatagctaa ggttttacac agtcatgaaa gtgatctgca 140880
ctgttaacat ttcaccctct gtgcaccatt ctgtgcttct ctctggtttg gagtctagaa 140940
ggttttattt acaggctatg acttaacaat cccagaacgg ctgacacatg cagtcactca 141000
agactggaca cagcaaggaa gtagtgggtc catgccaaag gctcagccag acgagacact 141060
ctagctgtgg caggagatgc cagggaatgc tccaagccta agcagattgt aaacaaggaa 141120
cctcaaattc atgaaaaatt cttgcttatg tggcccatgt cagtaattac tctctgcctc 141180
agtttccgca gctgacatgt aaataaaagc agttcatggt tcatcttctt ttcttatcgg 141240
ggtctcaagt gattctacaa accagccagc caaacaatca gagaataagt tgaaaagatt 141300
gtcttcattt attgaatgtg cttaactcag gcccgggaaa gggcgtcatc agtttctcat 141360
catttcactg agatatgcat ctattacttt tacatttcag gccaaaagtg tgatccaagc 141420
tgtcccaatg ggagctgctg gggtgcagga gaggagaact gccagaaacg taagtcagtg 141480
aacagcctca gacccatgtg tgaccgcccc tctcttcctt cacttgctta ggtgattgga 141540
tttgttttcc ctctgaagac tccaaagagt tactttatta cagggtcaga tgtgaaccag 141600
taggtgaagg acagtcttgc aaatctcacc gcatgcagtt aatccagggt gggctatttt 141660
gggagcttca gcctatcaca aataagtgaa catcagcagg ggctgggcgc ggtggctcac 141720
ccctataatc ccagcacttt gggaggcgga ggcggtcgga tcacgaggtc aggagatcga 141780
gccattctgg ttaacacagt gaaacctcgt ctctactaaa aatacaaaaa attagccggg 141840
cgtggtggcg ggcgcctgta gtcccagcta ctcgggaggc tgaggcagga gaatggcatg 141900
aacctgggag gcggagcttg cagtgagccg agattgtgcc actgcattcc agcctgggcg 141960
acagagcgag actccgtctc aaaacaacaa caacaacaac aacaacaata agtgaacatc 142020
agcaagtacc ccagccctgt cctctgaaca cagcacactt tcccaggaat ggaagacttg 142080
ctcctgttga cagcagtcac cagacttctt gtttcctctc cctccctggc tttctttggt 142140
acccacctac acagaagcct gagcacgggt tctcatgggg acttttccat gtggaccctg 142200
ctttacgatg gagagggcca ttctcctagg tatggttgtc tggctcagcc tctcagtggc 142260
caaggaacct ggggacatga gctcaaaaac ggacactatg tccttaagct gaattgtggg 142320
ggggctgtta ggcccttcta aacactactt cccagcaggt atttttgttc tttgtatgtg 142380
ctttctgcat tgcccaagat gcatctaatt atttagcagg tctcaaagtc tagacttgat 142440
ctcatgagtt ctcttaagtg attaaaaata aatcaggaga aaaaagaggc aatcagaaaa 142500
gggcatggtt tgacttagtt tgaatgtggt ttcgttggaa gcaaatgtgt cttcactttt 142560
tcatgaaaaa gtctgcaagt gctctgcgac atccctggga aatgatccta ccctcactct 142620
tcagctcaca gggaaccttt gctctttttc agtgaccaaa atcatctgtg cccagcagtg 142680
ctccgggcgc tgccgtggca agtcccccag tgactgctgc cacaaccagt gtgctgcagg 142740
ctgcacaggc ccccgggaga gcgactgcct ggtaagatgc cctccagca gcctccctgg 142800
agcaggctgg ggctgcaccc gccccaccca caccaggaca gaagacttcc tgtgggggag 142860
ctgtcaatta gcatttgtca taacagacag gatattgccc tctgcctggt gacaaagtat 142920
ctttagtatc ctgcctccac cactcactga gaccttggga aaatgatggg actaccatgc 142980
ctccatttcc ttacctgaca atgatgcata acaaagtctc tcccagttga atgcttaaat 143040
gatgagatgc ctgtgatgtc cgtcattagg acctgggcac agaacaagca ctaaatacta 143100
catgcaagta tttgtcatga atgtgccttg ttgccagcag cacactctct ttattgtttg 143160
acttcggcta tacctctaga gacttgacac tgtgaggtcc ctaagagacc catggagagc 143220
cacacaggtc ttgctggctg gggctgggtt agggcctcct gacacggatc cctcggctcc 143280
tccaccactg ctcaggcacc tcctgagctg caccctgccc tcaaggggtc ctgaagtact 143340
cactgtcgcc ccattgctcc agaaagtgcc agcagaagcc ttgctgcccc agcgggctct 143400
gagcagcact ggagggtaca ggtcagaagc gtcttggaag tcctggagac gccaaggctg 143460
gtggatgtga ctcctggagt gggagctggt gtgacgaagc ccttcctaag actaaatcca 143520
gagcactctg tggtttcaga gaagattcct aaattccaga gtttggaccc agacccagga 143580
attgtgactt ggttggcctg agctgtttct aatgtgagcc ccagggagaa gactgtgcgt 143640
ggggttggtc ctaggaaaag ccctcgctgt attgggtctg gctcctttac acggcattgt 143700
tctagcaagg ctttctgcca ttcagcaata cattataaaa tataccctca attgtacttt 143760
ataagggaag cccaatgtcc tttataaggg aaattaaaca taatttcatt ccatagtcac 143820
cgctataatg tgtgaactcc atcatctata cgttagtaaa cagacgtatt tttatcataa 143880
tccataaatt atgataggtg ggacagtgca cctaagaaaa aaatggactt tttagagaag 143940
ggtctttctg actctgcaga gggcgccagc tgggttttcc cacactagtg gaacactagg 144000
ctgcaaagac agtaacttgg gctttctgac gggagtcaac accgtgctgc gcttcctccg 144060
tgtgtggcgc tgagtgtact tacctcactt gcccagcgtg tcctctctcc tccataggtc 144120
tgccgcaaat tccgagacga agccacgtgc aaggacacct gccccccact catgctctac 144180
aaccccacca cgtaccagat ggatgtgaac cccgagggca aatacagctt tggtgccacc 144240
tgcgtgaaga agtgtccccg tgagtcctcc tctgtgggcc ctctaactgg tcaggcatcc 144300
ttgtcccgct ctgtctcctg ctgagccctg gagtatccca tcttggagag tctttgggtg 144360
gatgtgtttg ccttgcttgg aggaggcgac cctgtgcccg tccaggcaca caggcgaggg 144420
gaggggctgg cttgctaccg aggagcgggc aggtggtggc catctccacc catgggggct 144480
gctcagtgca cagggcagat ctgggtggcc aggccacctc acaggagaaa cacctgctgc 144540
tcagccctca ccactcatcc agcagccaca gccgtgggta ttcagttgtc tgctgggcac 144600
aaagccgtgg gcatgccact gtttagtgct tgtgccaagc aggtatttaa tacaccgaaa 144660
tcagagagtc tatcagaaga cctgccttct tgagtggtta aaattctagt gaaagttatg 144720
cctcttagga gtattgcaga ggttttgttt ttgtttttat tttgttttgt tttaatggtt 144780
tgggtttgag ttttgcttgt ttgtacttac atttgtactg gtggctccag ggtttaggga 144840
aattgtgaca taaaataatt cctgacagag aaagcaaaac tttgtctaat gaaagagttt 144900
tagaagccac tcttgatctc tagaagggga gattaactga gaaaaaaaat tgaaagaaca 144960
attatgaggg ggagatttta ccctgccaga tttgtgtaca tgaaaaattt tacattccgt 145020
atggaaaaaa aaaacacaaa ataataagcc attataaggt aaatgacaaa caaagctaaa 145080
gaaaaatgtg ccacagtgat gacacagata tatctttgag atagggctta acagagcttt 145140
aaaatccata ggaaaacact tcgagcctga gataccaaga gcagatggtt cacagaagaa 145200
tcatcaatgt cctataaata tttttgagga tcttcttggg gaacttaaaa caggaacagg 145260
ccaggcacag tggctcattg gctcatgcct ttaatcccag cactttggga gactgaaggg 145320
gctggattgt ctgaggtcag gagtttggga ccagcctggc caacagggtg aaacctcgtc 145380
tctactaaaa atacaaaaat tagccgggcg tggtggcgca cgcctgtaat cacagccgct 145440
caggaggctg aggcaggaga attgctttaa cccaggaggc ggaggttgca gtgagctgag 145500
atcacaccac tgcactccag cctgggtgac agagcaagac tccatctcag acaaacaaaa 145560
aaggaagaca tagagctcct aaaaataacg cagaagtctg ctattaatac aaatgaatta 145620
ctttaaaggt gagagcaggt ggaggagagg gctgaggtgc ctgctgggac gcaaaacagc 145680
tggcccctca agggacccag tgtttcctgc catgatgaaa cacctgtatt gtccacattg 145740
cggcctagaa tgttattaaa ctcttgaacg ggattccttc tctatttgca acctttcatt 145800
ctttgtcctt aaagtaaata aagccaaagg aggatggagc ctttccatca cccctcaaga 145860
ggacctggac cgcctgtgtg aggcccgagc acctggtgcc accgtcatca ccttcctttc 145920
atgctctctt ccccaggtaa ttatgtggtg acagatcacg gctcgtgcgt ccgagcctgt 145980
ggggccgaca gctatgagat ggaggaagac ggcgtccgca agtgtaagaa gtgcgaaggg 146040
ccttgccgca aaggtaggaa gcccgccggt gtgcggacga ggcttgttct cggctgctga 146100
ggctgggctc tcatgccacc tccaaaggaa cacatcttcc tcttctcatt aaaaaacaac 146160
tatacatatc gtttctttaa aacagaagat aaagctgtaa agctaggtta ggcaatggga 146220
aggcactgaa ggttgtgacg gggtgggggg ctctgatgag aacagtcaca gagccagccc 146280
cgctcagcag ctgccaggtg cccagccctg gggagaatcc agggaaggca gagctggaag 146340
cagtgcagct ccaagcggcc catgggaaat aatgaggaga acgcaaggtc agtgtgaggt 146400
gacagggatg gcatctccta caccgccgta gccccaaagt gtactatagg tcctggtgtc 146460 ccccccttccc gcctgcactc tccccagccc cttcagtgtt tgttgagtga atgaaggatg 146520
atgtggcagt ggcggttccg gtgaccggaa ttccttcctg cttccctctg cctgtggatc 146580
cctagctatt cttaatccaa caaatgtgaa cggaatacac gtctctctta tctctgcagt 146640
gtgtaacgga ataggtattg gtgaatttaa agactcactc tccataaatg ctacgaatat 146700
taaacacttc aaaaactgca cctccatcag tggcgatctc cacatcctgc cggtggcatt 146760
tagggggtga gtcacaggtt cagttgcttg tataaagaaa aacaaaatct gccttttttaa 146820 ctggtagaga ttggtgatca ataatcaccc tgttgtttgt ttcagtgact ccttcacaca 146880
tactcctcct ctggatccac aggaactgga tattctgaaa accgtaaagg aaatcacagg 146940
tttgagctga attatcacat gaatataaat gggaaatcag tgttttagag agagaacttt 147000
tcgacatatt tcctgttccc ttggaataaa aacatttctt ctgaaatttt accgttaatg 147060
gctgatgttt tgatattttt caaaagtgca gtttctcctg caggcaaaag gggacacgtt 147120
aagtccaggc ttgggtcatt cactgcggtg taaacacgct ttctccctcc cgcccggccc 147180
cagccagctg ccttggtggc ccataacccc tgagggtaga gggaggggac aggggtaggt 147240
gacaggcagc ctgggcctca ggcttttgaa actggacgcc agagccttgt ggggccacgg 147300
gcaagcctcg ggtctatgac tgccgcctga gctccgcttc cttcctctct aaaatgggaa 147360
gattagacca aaataacaag actgttttaa ggttggaatc aaataaggaa aatttgtaaa 147420
gctccttgta tgtgatacca gatccacaat tggcagataa tcgcagcagg agcctcttcg 147480
gggtaatcag atacgcggcg cagcaggggt ctcagggcca cagccagggg ggcggcggga 147540
gacatgcgga atcgcagcgg aaggcgggag gcagctgtga actgtggctc ggcctgcgtc 147600
cgccctgcgc atgtacactc agagaagatg ataatgaaaa agaaagcaaa tccaattttc 147660
ccacttactg ttcatataat acagagtccc tgagagtcta gagtaatgtc tcatacaaaa 147720
aagaaactcc tacgtggtgt gtgtctgaag tctttcatct gccttacagg gtttttgctg 147780
attcaggctt ggcctgaaaa caggacggac ctccatgcct ttgagaacct agaaatcata 147840
cgcggcagga ccaagcaaca gtaagttgac cacagccaaa gcctggtaga ttacatttgc 147900
ctttttagtt ggaaattagg cttaacagga gagttgctaa gatagggcac agagctcctg 147960
catctctcgc cggcattccc aaatgctatc tcacatgagc aggcacaggg agcaagactg 148020
cacgaccact ggcacaggct gtccgctaaa ccacagactt ctcagcgctc gccagtgctt 148080
ctgcttctgt gtccactcca gatcccacat tgcacttagt tgtcaaatct tttcagtcca 148140
tttctaacct atattagctc ctgtgtcttt ccttgtcttt cacggccttg acacttacaa 148200
aacgtgtggg tcaggtactt tgcacactgt ctaaccatgt ctgttcagct ggtgttttct 148260
caggatgcaa ttgaggttat gcacatctta tcacagggac cagagagact ttttagcacc 148320
actcttcaag aatttccact ttttcagctt tgacagtgga atagacatgc aggtgctcac 148380
acacaagcat ctttaatatg gtaatggtaa tcatcagttt agtggtgtgg aggaggagat 148440
gggaatctct tagtgaaacc cgccttggaa gcagcctcgt tatgagaact gctgccccta 148500
cttgactctt aaagcactag ataatactgt gcaacattaa agagaataag agtgcgtgaa 148560
atatgcattg cctcccataa actcccttgg ctctgaatct ctgatactaa atatgtggct 148620
accgttgctt cccagaaagg ccttttttgct ctgaattctc tggaatgctt tctttgacca 148680
agattcttat aaaaataaga gatttagagc aattttcttg gatggctggt atgagccagt 148740
tggcttagtt gtagggattt aaacaagata agggttactt acttttcaca tttaatgaga 148800
agtctggtga ttccagctcc tactgagaca gggtggccac acgttccagg gtgtgactca 148860
ctgaggcccc agacctgccc tgcaaggaaa acctggctct gccctggtgt cctggcctcc 148920
ctgggcatat gtgggggaga attcctaatg gtattggtta caggctccta tgcgagacca 148980
ctcatctgtg taggagaaag gaaaaagatg ggggaaagaa gagcagcagg gagaggagaa 149040
gcctctggat gatactctaa ccccctgcca tccaacacct gaacatcagt ctcttcatcc 149100
agtgctctca gctggcccag cccccagcct ggggtcagat gagagcttcc tgcaaatgca 149160
gatctctttc ctgtggctcc ttctcaatta cagacagctc ctccacaagg tgcactctgg 149220
ccttgtgctc cctccccaaa ccagcccagc cctcccagcc tgcatcatcg tggtcctgta 149280
ggggctagag gttctcacac ccatcgtggt ctggcagagg ctggtggttc tcacacccat 149340
cgtggtccgg caggggctta gtggttctta tacccatcgt ggttcaggag gggctagtgg 149400
ttctcacacc catcgtggtc tggctggggc tagtggttct catgtccacc gcgtgctttc 149460

```
ctgctcctcc aggtggctga ggacatcccc ccttcggtct gaatgacttc catccagtca 149520
tctgatatac acattggacc acccaatagc atcctagtgt catgttggat ggtgaagaaa 149580
atgccacagt tactgctttc agggcctcac aaccttgggc atagcttttt ggaggaaggc 149640
cccacttccc aggcatccct cccagacctg gtcagaggcc cctgctcttt gcttccatgt 149700
tgcccacact cactgtgctc ttcacaccgg ctcaaaatga tctgcttacg gggttgtgtc 149760
accaccagat caagcgtcct ggagaggagg aaacatattt aacctgcaca gaatttggga 149820
cagagaacct ctagtgtttg ttcaataaat atatgaatgg atagagggac aggttgggtg 149880
gtggatagat ggatgaaccc acacctttga agtgtatttg gctgtttgag aggttagaat 149940
atgttctcaa tttccaggca aaatgaaaat ggagaaaata taatgacatt aaggcatttt 150000
attcatcctc cccatctgcc actgggttaa agatactaaa taaacaagga actatctttt 150060
gcctggagga actttaaaaa cacctgcagt tttcaaaagg tgcagtgtgt gcctcccaca 150120
gcatgaccta ccatcattgg aaagcagttt gtagtcaatc aaaggtggtc tggagaaaca 150180
aagttttcag ggatacattg tttttataat ttttcaccac atgatttttc ttctctccaa 150240
tgtagtggtc agttttctct tgcagtcgtc agcctgaaca taacatcctt gggattacgc 150300
tccctcaagg agataagtga tggagatgtg ataatttcag gaaacaaaaa tttgtgctat 150360
gcaaatacaa taaactggaa aaaactgttt gggacctccg gtcagaaaac caaaattata 150420
agcaacagag gtgaaaacag ctgcagtaag tcaccgcttt ctgtttagtt tatggagttg 150480
gttctaatgg gtcctttatt tgtatttaga atattgaagg gctattccca tttaaattac 150540
ttttttcagt tccttaagaa gcaaattaaa atcttaagat tcctaactgt gaaattacca 150600
tgtgaattcc attaaaactt tttccagatc attaccattc aatgggatga atttaccctg 150660
aggtttaggc taccaattat ttgtaatgta agtaactaaa tttagtatta gttatattac 150720
cttttagttg taggtcactc tctgctcatt tcagcctgta aagactacag ctacacacat 150780
acacacacag aggaatggaa tgagcacttt acatcaacac ttcctgttct ggctctagag 150840
cctcagcttt tgaagctggt gagagcctgg cctgtgctgg gccttggcca cgggcagcgt 150900
cagctttgag tcaagtgctg gtctggcctc cctagctttg agcctctgtc aattccctta 150960
atctgtttag gctttggctt cctcatccat agaatggaga tatgaatgat tcctacgccg 151020
tagtgctttg agagaattca gtgaaattcc tgtgtgtaaa acccttccat ggtgcctagc 151080
acacagcaca cagccaatgg cccaatggct cctatcagct gtgggatttg tcatcagaac 151140
accaccagct ctgctccagg ctgccctggg taccatcaaa acacaccctg tgcccagcag 151200
cacctgctcc tctgcacacc tggttccttc agcaggggca gtggccgtgg gagcacagaa 151260
aacatggagt cccatctggt ttaattgatg ccattgccaa aggggaggac tcacggcacc 151320
ccctctcggg tgccagggtg cctggctccc accaggagga agacctgtcc tccactgtca 151380
ggcacatttc agtcttccca gcagccagca caactacttt gtccttccag tcacggtcgg 151440
cctctgggaa gcccagtctg tgtcctcctc cttcaggggt agccagcatg tctgtgtcac 151500
ccaaggtcat ggagcacagg gcccctcccg ggaaggtgcc gtctcctccg gcccctcggg 151560
tccctgctct gtcactgact gctgtgaccc actctgtctc cgcagaggcc acaggccagg 151620
tctgccatgc cttgtgctcc cccgagggct gctggggccc ggagcccagg gactgcgtct 151680
cttgccggaa tgtcagccga ggcagggaat gcgtggacaa gtgcaacctt ctggaggggt 151740
aggaggttat ttctttaatc cccttgcgtt gatcaaaaat aaggctccag gttgttgtta 151800
```

```
tagctttaca ggcattctgt ttgattttct cttcctttta ttctttgccc ttggcttttg 151860

gaggttttgg gttttctgtg gggagacggg aagttgtttg attgcgttat ttttggcaaa 151920

tttaagcaca ataggaaata agcaagtatt attgcctaat ataatccaat aatttataga 151980

atctcttttc ctggaagtat cttaaatttt tctaagctac aaaaagttcc taagacaaat 152040

gagacagtca tcaatggttc atctagccaa caccgtggcc atttgggctt ttctttgtag 152100

tgcccgattc ctggtgtgtg aaaataaatt aacacaaatt atattgccaa gttaatatct 152160

gttttatgtg cccccagcat gtgttgaaca tcaaacagta ccagggactt taaatatacc 152220

cacggacaaa gaaataattc ataatgatgt ttgttgaatt tagttgcaat caataaaaag 152280

tgcagtttgt gaatgctctg aggttcttga tattgatgta aggctttgaa cgacaaatga 152340

ggacaaaaca taaataggaa agtaaaactg aaggatagag gccaaggcca tgttttagaa 152400

gatttaaaga aaaagggaaa tttggtgagc accataggaa ttacagatgg ctgtaggaat 152460

tcttcctgtt ttactctctg ggcatggacc acagcttgga tccagaaata tttaggagca 152520

ggataagagg accaagttca attctatagg aatcctttag ctgataggct cagaacaaat 152580

cacataattg atagtgctgc ttcaacttca agtaaggaat attgatgcaa tccttacagc 152640

tacaaatgga cagtggtctc atgttttcag ttttcaagtg tttcttaaga ggcaaggtga 152700

tgaaaacgcc cacgtgggga gccccatgtc cttccattag tgtagagaaa cctggtgtcc 152760

agcagcacct gctccctctg caagcccagc ccccttcagc aagggcagtg acccagagaa 152820

gaagcacaga agacacaacc ctgtatcaca ttttgtttaa tggtgccatt gaccaaaggg 152880

gaggatgaaa ggcacacact tttttgttgt tttttgagac agagtctcac gccatcaccc 152940

aggctggagt gcagtgatgt gatctcaact cactgcaacc tctgccccct gagttcaggt 153000

gattctcctg cctcagcctc ccaactagct ggaattacag gtgtgcacca ccatgtccag 153060

ctaatttttt gtagttttag tagagacggg gtttcaccac gttggccagg ctggtctcaa 153120

actcctgacc tcaagtgatc tgcccgcctc ggcctcccaa agtgttggga ttataggcat 153180

aagccactgc acctagccaa ggcacacact ttggagaata aacactcctt gttcgctgct 153240

ggagggtaga actatgcttg actactaggc agagtccagt cttactgaca aacagccgta 153300

catctgttct gtcttttcaa tcaaacatca gcttcttgct taacattgat gtgtacatct 153360

tgagggatgt caaaatattg taagctaagt tttcatacc tgtgttccac actcaccatt 153420

tttagtaata accattgagc gagttcattc tccctccttc ctttttctat cacttaatct 153480

aaaattatca tttttccagc ttaattttga taaccatgaa tctggtatta gaggcaggga 153540

acacctcctc aggactatct tttcttttat catttggctt gcttacccaa tatgcaaaaa 153600

ctatgctgta gaaaaagcag aaaagatatc ttgattatga atgaagctcc tgtgtttact 153660

cagagagaag atgacccagg attcagttaa caaaatcagc tgattatatt actatatagt 153720

cctggagtcc caactccttg accattacct caagttattt ggaattttga agaggtgatt 153780

tgtgttcctg caataatgtc tcaggggtgg gctgacgggt ttcctcttcc tcctctcagt 153840

gagccaaggg agtttgtgga gaactctgag tgcatacagt gccacccaga gtgcctgcct 153900

caggccatga acatcacctg cacaggacgg gtaagagccc cttgctgcta tccacgtcca 153960

tttcatggga agggccttca cagaagccga acagtgatga tggcccaggg catcctgtgt 154020

gggcaggacg gccatcagag ccacttccca gaggagacgg caggcgctga cagcgctgtc 154080

cgggcagggt gtcggtgaca ttagcacaca cattagcctg cgatgaacat tcactctttc 154140

tgctgacacc cccaacctta tctaagctta tcaaatcctc acatttaacg gaggctgttt 154200
```

tcacctggtt tcccccatcc ctgacctagt cagcattgct ttatcgcttt catcaaacat 154260
cctcaaattc ttaacattag cttgtaatta attgaagaat ttttaaagaa attgctagca 154320
aaacttttta aactgcacaa ctttgtatct atatgttcaa taacatatag atacaatatt 154380
ctttacaata atcttttaaa gaatatgagt gagaattcgg gcccctctca caccaaatgt 154440
cctgatgttg ttaattctca atgttattat atagggagct ctgttttctt gtgagcttca 154500
acagccagtt ctaaatctac taactgaaaa catttttag acattctcta aattgggcag 154560
aagatgacag gactgtgttt tgagggatag gctgccagcg tggctgctta caaagtaaag 154620
acttggttta taggtttgca tggtgttggg ttaaatttct gtcattaaaa taattggcga 154680
tattgacata gtcatctaat tatgctggct ctgggcacac acagcccttg agtggacaaa 154740
accaacatga gagaacttag ccaaggggaa agcctttccc tgctggtttt atttctgcta 154800
cttctgaagt gtggggcaca caacctgagc agtgctttta tttgagtccc aatgctttta 154860
tttgagtttt gcaaggttat tccaagtttt acaaatagaa ggtagcgtat gactcagtcc 154920
ttgatatgcc aaccactgca cagagacttg ccaccttcct gtcactggag aaacactcat 154980
gtgggttttc ttaaatttgc ctccctctga gcttcccttt aacttcaact ataatatgca 155040
agaaagacta tctgaccata aatacacatt tgggccaatc aagatggttt tgccaaggaa 155100
agatgcccac aatggttaag cagaatgcaa taatgtagag aatatcattt ctttcatgct 155160
ggtgtatatc atatgcattc aaaaacaggg agaacttcta agcaactaac agtgaccata 155220
tcaagcaggt gcaatcacag aataactggt tttctccttt aagaattttt ctatcatttg 155280
gctttcccca ctcacacaca ctaaatattt taagtaaaaa gttacttcca ttttgaaaga 155340
gaaaagaaag agacatgcat gaacattttt ctccaccttg gtgcagggac cagacaactg 155400
tatccagtgt gcccactaca ttgacggccc ccactgcgtc aagacctgcc cggcaggagt 155460
catgggagaa aacaacaccc tggtctggaa gtacgcagac gccggccatg tgtgccacct 155520
gtgccatcca aactgcacct acgggtgagt ggaaagtgaa ggagaacaga acatttcctc 155580
tcttgcaaat tcagagatca aaaatgtctc ccaagttttc cggcaacaaa ttgccgaggt 155640
ttgtatttga gtcagttact taaggtgttt tggtccccac agccatgcca gtagcaactt 155700
gcttgtgagc aggcctcagt gcagtgggaa tgactctgcc atgcaccgtg tccccggccg 155760
ggcctgtgtt gtgcaatgct gcacatcaca acaggagggt agggggacaa aagagcacag 155820
gtcctggcag ctgccacagt ctccaggggc ttttgcgttt ctctccagat ttctaaggtt 155880
aacatgggga ttagctgttt tgcaatgaat aaaaggtaac attgcctgga atgttgctta 155940
aagacacttt tttaaagcta gttgattgtt aagctgttgc tacttaaatt aaaactactt 156000
tgggccagac gcagtggctc acgcctgtaa ttccagcact ttgggattcc aaggcaggca 156060
gatcacttga ggtcaggagc ttgagaccag gctggccaac atggtgaaac cccacctcta 156120
ctaaaaatac acctgtagtc ccagctactc aggaggctga ggcaggagaa ttgcttgaac 156180
ccgggaggca gaggttgcag tgagccaaga tctcgccact gcactccagc ctgagcacca 156240
agagcgaaac tctgtcgcaa aaaacaaaaa caaaaaaaaa agctactttg actggaatta 156300
gcagaagcac tctgattgtg tgtatcttat ttactggaat aataaagctg tcaatcaaac 156360
tggatcccac tcaacaatca gaaagagaag ttgagctgtc atatagtagt tcacacttac 156420
ttctgtttct caaaatcctc agctttgttt ggaactgtta ctcattcttt ctctgaatcc 156480
atctgtatga gttgtgtgcc cttgggcaag ggtcttacct tctctgtgcc tcactttctt 156540
ttctgtaaat tgggataata atgctgcata gctcacagga tttttatgac catgagttaa 156600
gatatgtcat atacttaaaa tggtgcctgg aaaatggtga atactgagtc aatgatagca 156660
tcattgatgg tgggatggtg atgaggaggt gggagtcaca atggtggtgt tgatggtggt 156720
gatggtggtg aggaggtggg agtcacagtg gtggtggtgt tgatggtggt gaggaggtgg 156780
gagtcacaat ggtggtggtg atggtgttga tggtggtgag gaggtgggag tcacaatggt 156840
ggtagtgatg atggtgttga tggtggtgag gaggtgagag tcacaatgtt ggtggtgttg 156900
gtggtggtgg tggtgaggag gtgggagtca caatggtggc agtgttggtg gtgaggaggt 156960
gggagtcaca atggtggtag tgatgatggt gttgatggtg gtgaggaggt gagagtcaca 157020
atgttggtgg tgttgatggt ggtgatggtg atgaggaggt gggagtcaca atggtggtga 157080
tgagggtggt gatgatgatg aggaggtggg agtcacaatg gtgtcagtgt tgatggtccg 157140
atggtgatga ggaggtggga gtcacaatgt tggtggtgtt gatggtggtg atgatgatga 157200
ggaggtggga gtcacaatgg tgtcagtgtt gatggtggcg atggtgatga ggaggtggga 157260
gtcacaatgg tggtggtgat gacggtgttg acagtggtga cgaggcggga gtcacaatgg 157320
tgtcggtggt gatggtggtg aggaggtggg agtcacaatg gtggtggtgg tgatggtggt 157380
gatggtggtg aggaggtggg agtcacaatg gtggtggtgt tgatggtggt gatggtggtg 157440
aggaggtggg agtcacaatg gtggtggtgt tgatggtggt gatggtggtg aggaggtggg 157500
agtcacagtg gtggtggtga tgagggtggt gatggtgatg aggaggtggg agtcacaacg 157560
ttggtggtga tgatggtgtt actggtggtg acgaggtggg agtcacaatg gtggtggtgg 157620
tgatggtggt gaggaggtgg gagtcacagt ggtggtggtg ttgatggtgg tgatggtggt 157680
gaggaggtgg gagtcacagt ggtggtggtg ttgatggtgg tgatggtggt gaggaggtga 157740
gagtcacaat ggtagtggcg atgatggtgt tggtggtgag gaggtggaag tcacggtggt 157800
ggcgatgatg gtggtgagga cgtgggagta acaacagtgg cagtgacggt gattgagaca 157860
tgatgatgat ttgtcaactt tctaggaaaa caatcatata atctccaaca gtgatatctt 157920
aatatctttt ccaaaagtat cagatcatat tataagggcc aagtttccag aataatatca 157980
gacataatga cagtggacat cagagcttgg catctaaagg taatgggaat agctctaatg 158040
tctcagcgtg aaaaacaaca tttgctatta gtctgagata ctaattatct agttaaggaa 158100
gtactcacct atacctagtt tttaactgtt ttttaaaatc tggaattgat tttgaatttt 158160
aacaaatatt tccctgggaa caatgtaaga ttcttcatat tttcgccttt gggtatacca 158220
acatgccagc tctgttggcc actttgtgag ctcgatgaag catggtataa aagatgcttt 158280
gctagtgttt cacgtaatct atttctataa gcaattttgg agctaagcct ctgaaacaga 158340
attatattat ctgtatagaa taaatgtttt atcttccccc ttttctttct tctggaatag 158400
atgtgcatca gtatctctgc atcaatatct ctatatcagt atctctgtgt cagtgagcat 158460
atgttgctgg gcttagggga ggtccagaaa gtgattgggt tttggcattt tcaatacact 158520
tactttgtat aagaaatagt ttgccaaata tagaaagagg ggatttagtc aagatttaaa 158580
ttaaaaatgt tagtggtcat ttttctaatg tctttctatt ttttcccagg tcctaataaa 158640
tcttcactgt ctgactttag tctcccacta aaactgcatt tcctttctac aatttcaatt 158700
tctccctttg cttcaaataa agtcctgaca ctattcattt gacatatgga attttataaa 158760
tattttcttt agtatgtgtg attacattcc tgattctgag cctttttaga tgagtatata 158820
gtttgatata atcttgttat tgccacctgt gtcttctccc aaagccatta attatatagg 158880
aattacacga tagaaatggg tttaattttt aaaatacggc caagtgttga tgagagggaa 158940
aattttttta atttctttca ctgagtattt atgacgtgca caacattcct gaatatattg 159000
tctctctcat ttctcagatg ggatgtattg ccttctccat ttctattgtt aaagaaacac 159060
ttacaggggt ttctttaaca acttgtgaac agcagcatca gagcccagac tacagcataa 159120
gcagctgctg attccaaaag ccctaccttc caaccgggca ggtgcagcca cccagacgag 159180
ggggaggaac cctggaggaa tagctatttc tttttttttt ttgtcgagac ggagtcttgt 159240
tctgtcaccc tggctggagt gcagtgccgt gatcttggct cactgcaacc tccacctccc 159300
aggttcaagc aattctcctg cttcagcctc ccgagtagct gggattacag acacctgcca 159360
ccacgcctgg ctaatttttg tatttttagt acagacaggg tttcaccatg ttggccaggc 159420
ttgtcttgat ctcctgacaa gtgatccaca caccttggcc tcccaaagtg ctgagattac 159480
aggcgtgagc cactgcgccc agcaggaata tctattttta aatggaactg tgttttcata 159540
gtacacggtg aggagaaagt tgctttgaaa tctttatcct aataaaccaa ataatatgaa 159600
aatttgccta ttttaattat atgtaacaaa gtttagttac tgctataatt gcaaatatgt 159660
ataaattcct taccaaaaaa aaaagaatca agtgggagcc agagaataat ttttctgaca 159720
gaattaaata acatgctata gctgcttgag ttcatactca atagtcattt ctgcagagtt 159780
accgagggcc tcatcagcgt cagcaggagc ccctcgcctt ctgacgctct cacatccttc 159840
tctcctgcag ccccgtcctg ccactgtcct tgtccagctt ctcttcaagg gtcaactggt 159900
ctacctttcc ctacaagtct gtcacagctt cttgttagca atccctatgg ttgcccaaaa 159960
gcattttcag agcctgcata agactgcatc ttgtagaaaa tttgcagttt caatctgccc 160020
tccctctgcc gggtgttccc attgtattgc attcagcagg cagggagaga ctgctattag 160080
gtctgttcct gagtgactgc tttctgtctc agactgtttg gtgtctgtag gaggtagtgg 160140
ggtgggcagt aacgaggtct cctgtatatt ccacccctac gaagcctgtg tgtttggttt 160200
atgaactaag ctcaaaagca ccacaggggt aagactgcag tacatgacac catggaaaag 160260
agggagcacc cagaccccca aattaagaag agcagtgtag agaacagaga cctggagagc 160320
agagatagaa actgttagga tcagattata gtgttacacc agggctcccc aggcctctca 160380
catattgaaa tgtacttgtc catctttctc caggccagga aatgagagtc tcaaagccat 160440
gttattctgc ctttttaaac tatcatcctg taatcaaagt aatgatggca gcgtgtccca 160500
ccagagcggg agcccagctg ctcaggagtc atgcttagga tggatccctt ctcttctgcc 160560
gtcagagttt cagctgggtt ggggtggatg cagccacctc catgcctggc cttctgcatc 160620
tgtgatcatc acggcctcct cctgccactg agcctcatgc cttcacgtgt ctgttccccc 160680
cgcttttcct ttctgccacc cctgcacgtg ggccgccagg ttcccaagag tatcctaccc 160740
atttccttcc ttccactccc tttgccagtg cctctcaccc caactagtag ctaaccatca 160800
cccccaggac tgacctcttc ctcctcgctg ccagatgatt gttcaaagca cagaatttgt 160860
cagaaacctg cagggactcc atgctgccag ccttctccgt aattagcatg gccccagtcc 160920
atgcttctag ccttggttcc ttctgcccct ctgtttgaaa ttctagagcc agctgtggga 160980
caattatctg tgtcaaaagc cagatgtgaa aacatctcaa taacaaactg gctgctttgt 161040
tcaatgctag aacaacgcct gtcacagagt agaaactcaa aaatatttgc tgagtgaatg 161100
aacaaatgaa taaatgcata ataaataatt aaccaccaat ccaacatcca gacacatagt 161160
gattttaatt atttaagagt agtttagcat atattgcttt atgatttaat taaaaatctc 161220
caaaatatat gccaaagaag tagaatgaga aaaatgtata tttctctttc acttcctaca 161280

-continued

```
gatgcactgg gccaggtctt gaaggctgtc caacgaatgg gtaagtgttc acagctctgt 161340
gtcacatgga cctcgtcaag aatgaccaca ctgctgtggg tgaagatgct ttcctgcatt 161400
tctgactgtc ctctgtcctg atcaagtttc tatggctctg ggccagccta ccctcagcca 161460
gggtttctgc agagactgcc cagctggttc cacgtggctc cacgtgccaa ctttgtcctc 161520
agtggaggga aagttggaca cacagtgctg gggctgctcc ctgctccgcc gttgctcgat 161580
gcatggcctg cctctgaatt ccttggttcc actggttttg ctgggtcctt ctgtgcctct 161640
agctcctctt tttttctgtc cacttacccc attggtccca tcacaagcct gtgtgtgagt 161700
ggcctttctg ttcgatgaca acctccagca taggggagtg tttctccttg ctttctttcc 161760
cagacacact gcccagcaaa ggcaaaaggg cttccttcaa catcagctct ggccagtttg 161820
ccagagcaaa gccctgagaa aagcaaggtt gaaaagtctt attcaaactc accaggaaag 161880
agtggtgtta ctctcgatgg cgtctagcca ggaatcatgg aattatacac cgagcacctg 161940
tttgccattt tggatgtttc caaacatgaa ccaaacttcc aggcccctct gccatctctg 162000
gtaacattta caaagtccct tcctcaccac tgcccttcct tcattttggc atgctcctcc 162060
gcccccgagt tgacagccat agctctctct cctgccacca gtgtcacatg atcgaggaag 162120
aaggcaactt caaaaagact gggtcccctt ccactcccat ctcttcagtg agctgctagg 162180
acacccagca gaacttcccc actccacact gcaatctcag ggatcttagt cacggggctt 162240
tccaccatgt ctccacctgg aaaccagtca tggccattcc ttcttacatc tgctcttttc 162300
catctttttc ttctcctcct gttcacccgc ccttactctt gtggcgccct atggatatgc 162360
gctccatagc aaatgattct ttatatctta cggtattcta gtgagctggc acatgtggct 162420
tctggtttcc tctctctgga actagacatg acctctgtgg gagggaggat taaatgcacc 162480
ctacagtctg aggctgcatg atgacatcac tcatcacaat gatgctttct atgtctgaat 162540
cctattcctt tataacccct ttcaagctcg ttcagagagt atttcacaca atccatgtgc 162600
tcatcttaaa agccaaggac ccagaggagt ctcagcattg ccaaaaagtc ccttcaccca 162660
gcctggccag aggcagtgcc tggtccatgt gtatggacta tggcacttca attgcatgga 162720
aatactcttg gaatgaacaa aataccaatc catgaaaaag cattattgaa gtctaagtta 162780
ttttttgaat catattttgt taatcaacaa attgaaaaat actcattata tggagaggtc 162840
cagataaagc ctcaatttta aaaaatgagg aaaagtgtgc ctggtagggg actggggaga 162900
gcttgagaaa gttggaaacg ttgccttaga agcctgtttt ttctcctttt agaagctaca 162960
tagtgtctca ctttccaaga tcattctaca agatgtcagt gcactgaaac atgcaggggc 163020
gtgttgagtg ccaaggccat ggaatctgtc agcaacctca cccttccttg ttcctccacc 163080
tcattccagg cctaagatcc cgtccatcgc cactgggatg gtgggggccc tcctcttgct 163140
gctggtggtg gccctgggga tcggcctctt catgcgaagg cgccacatcg ttcggaagcg 163200
cacgctgcgg aggctgctgc aggagaggga ggtgagtgcc agtcctgggt gggctcagga 163260
gccctcgcac cccgacagga acaagggcca gccccgagaa cgggccatta gcagttgtgt 163320
atgttagata cataattgta ttatgatgca gaaagaatct ctgaatgtgc agttataccc 163380
agttggtgac atgttggtac atccatccga ggaaatggca atgtttctag gctgcaccct 163440
tcaatgtcca caaagctgtg tggcatctgc ttaggacccg gtgcctgtgt gtgcatagga 163500
gggaggccag gaagcctggc tgttgatccc atgctggcac tgtggcgaag gcgagagatt 163560
cctgctttgg aaaacaccat tgtccacaca gtggctttgt ccatgatgga cttcgccaca 163620
gcccagtcct gtgctggaag ccatgttctc tggaaagagc aacccagcgg ctcataagca 163680
```

taagcgcgtg tgatgtgccc caaccaaacg accgccatgc acaacttccc taccggagtt 163740
ttcaatccag ttaataggcg tggaaacaga catagaaatt gtgtttgttg aaaggtagct 163800
gttcagttaa agaacacctg tatcagagcc tgtgtttcta ccaacttctg tcaagctctg 163860
tagagaaggc gtacatttgt ccttccaaat gagctggcaa gtgccgtgtc ctggcaccca 163920
agcccatgcc gtggctgctg gtccccctgc tgggccatgt ctggcactgc tttccagcat 163980
ggtgagggct gaggtgaccc ttgtctctgt gttcttgtcc cccccagctt gtggagcctc 164040
ttacacccag tggagaagct cccaaccaag ctctcttgag gatcttgaag gaaactgaat 164100
tcaaaaagat caaagtgctg ggctccggtg cgttcggcac ggtgtataag gtaaggtccc 164160
tggcacaggc ctctgggctg ggccgcaggg cctctcatgg tctggtgggg agcccagagt 164220
ccttgcaagc tgtatatttc catcatctac tttactcttt gtttcactga gtgtttggga 164280
aactccagtg tttttcccaa gttattgaga ggaaatcttt tataaccaca gtaatcagtg 164340
gtcctgtgag accaattcac agaccaaagg catttttatg aaaggggcca ttgaccttgc 164400
catggggtgc agcacagggc gggaggaggg ccgcctctca ccgcacggca tcagaatgca 164460
gcccagctga aatgggctca tcttcgtttg cttcttctag atcctctttg catgaaatct 164520
gatttcagtt aggcctagac gcagcatcat taaattctgg atgaaatgat ccacacggac 164580
tttataacag gctttacaag cttgagattc ttttatctaa ataatcagtg tgattcgtgg 164640
agcccaacag ctgcagggct gcgggggcgt cacagccccc agcaatatca gccttaggtg 164700
cggctccaca gccccagtgt ccctcacctt cggggtgcat cgctggtaac atccacccag 164760
atcactgggc agcatgtggc accatctcac aattgccagt taacgtcttc cttctctctc 164820
tgtcataggg actctggatc ccagaaggtg agaaagttaa aattcccgtc gctatcaagg 164880
aattaagaga agcaacatct ccgaaagcca acaaggaaat cctcgatgtg agtttctgct 164940
ttgctgtgtg gggtccatg gctctgaacc tcaggcccac cttttctcat gtctggcagc 165000
tgctctgctc tagaccctgc tcatctccac atcctaaatg ttcactttct atgtctttcc 165060
ctttctagct ctagtgggta taactccctc cccttagaga cagcactggc ctctcccatg 165120
ctggtatcca ccccaaaagg ctggaaacag gcaattactg gcatctaccc agcactagtt 165180
tcttgacacg catgatgagt gagtgctctt ggtgagcctg gagcatgggt attgtttttg 165240 gtatttttg gatgaagaaa tggaggcata aagaaattgg ctgaccctta tatggctggg 165300
atagggttta agccccttgt tatttctgac tctgaaactt gcattcaatt cactccacca 165360
agttatctca tctttgaaat ggcttttttt aaaggtgcct agaatatgat ggcgtgcagt 165420
ctataaactg ttgcccacct tctgtacttt ctctcagaat aattcacatt cttctccagt 165480
gtctgttgat tgttactttg tggaataagt tcttggaaaa ttccacaaga ttattgttat 165540
cttcttacta ccaattctat tgaactttct ccaccttctc tgggccttcc ccagccagtg 165600
gtgggaagat gctggctgga gtctgacaga gcctcttcta cactggcctg ggcttgctgt 165660
gagttggtgg aaacctttgc tcttgtccca acacagagca agtgaaagag gaggtcaagg 165720
ggctcaggca gcggactagg gaagcagaat cgaggaaaag gaaaaatggc tgacttatta 165780
cctcaaaact ctagagaatt tagttgatct tacagccaag aaggacaaaa gccagagagt 165840
aatatcctcc gcctcatgtc taacccacag aatacatagc aagtaaagag aacatgggcc 165900
tttataaaaa tgtcttaaga tacaattttt taattggagg aaatctacag tttaattttc 165960
tctgggcagc ttttcttcct tttattatag taggggaaat cccatgttga tatacttcta 166020
aatgaaagat gatgaattga tataatacaa taaaaaatct gtaaaattga tgatatactt 166080
atcaagaaaa attagctttc attttaacgg tttacaaatt gagtcaagtc ctagtaacaa 166140
aatgttaagt ctattaacat aaccacaaga aatacaggaa gacgggcaat ctgtgaagcc 166200
tttcacttac aatctctggc ccctcacctg tgctgtgtag gaaaatcttt gtgcacaatt 166260
tgcttcctta attcattttt tattcattca acacattcta ataaattata caaaatcatg 166320
ttgaaatgtg aatttcagtg gtatttataa atgcagtgtg aggagggttt ggatgtattc 166380
taagacaata gttgtgcttt gggaaggaag cagtgttcac tgaaaagtgc ccccaggacc 166440
ttttaattgg aggaaatatg cttctgtgga gttggaaatg gggtagaaga tagataaggt 166500
caaggcttaa aagttaagtg cacccaacat ctgaagcgtc catgggcctg gcatggtggc 166560
tttcgcctgt aatcccagca ctttgggagg ctgaggcagg aggatccctt gagcttagga 166620
gtttgagacc agcctgggca acatactgag acccagtctc tacaaaaaat aaaaaattag 166680
ctgggtgtgg tgtctcatgc ctgtagtccc agccactcag gagatgggaa gatggcttga 166740
gtccaggaga tctaggctgc agtgagctaa aatctcacca ctgcactcca gcctgggtga 166800
caaagcaaga ccctgctcaa aaaaatagtt agatataaat attaatatag atacctatat 166860
atatctgaat atagatatct atatatactc tgtatatagt tatttagata tataaatata 166920
tatgatatat atttagagag atatatattt agagagatat atatttagag atttatatat 166980
attttatata tatttagaga tatatatctc taaatatata tctctctcta aatatatata 167040
tatctctctc taaatatata tatatcccta aatatattaa ataaataaaa gaaataaaag 167100
aaagctcagt ttggcctcct gcttgtcctg tctcctcatc ccctcttccc cctccatcat 167160
tttatttcct tgccccatgt ttcttcactg cggccatgtc ccccctcctc tccaatgatg 167220
gatgtcatgt ctgctgcagt cagagggcga caagcctgga gtgttccctg aagcctgtgg 167280
tttgtggttt gtcctgcagc tcaggctgcc caggcctcac cagcaatcct ggcgggcagg 167340
gcaccacact gggatggaga gggggaagct ggaggaggca ctttctggta aagaaagcaa 167400
aagccagcag tgcccaggcc aatttcaaca gggagttaaa tagcacctta atcctgtggc 167460
aggacagctc atggggccat gtgtgctctt agaaagactc acatgcacgc atgcacggca 167520
gcaatgactc catactcacg ttcccctgca gacaccaggc ccccacagcc ggcacacaca 167580
ctgcagcccc agttccatgt tgctagcagt ggcttagtga atgagtaaag ttcttaaaat 167640
gcaggggaca cctgcccttc attcataagg ctggacgtac acctctcctt aaggagttca 167700
agagctagtg gaatcccaat tcatacggta gagccattca cagatgagag agacaagcca 167760
gaaggaagga accaaaagtc atgtcagcag ttaggacaaa ataacaggct ttcaaggtca 167820
caaagcctca gggacactcc tgcggtggga ctgggctagg agccatgggg gctccaactg 167880
tgcgctctgc ctgccagcct gtgggtgctg gggctccacg aagattgttg tggaatacca 167940
agcatgcttg ctgtaggtca cggtgcacgt ttactacttc caagacaaac agccgagaac 168000
aaagctcgct ttagcttctg cgtacaccga acgggacaca cgactgaaca gcgttcccat 168060
tgtgcctgct gggtggggag gaagtgatgg cccagtgggt ctatcagatg ttagtaggat 168120
ggggcctggc ggggctccag gctctgtgtg gccgacaccc acgccccccg ctctgctccc 168180
cattcccagc cccaggtcag ccctgcgagg ccctgcagca gatgggctgc tcaaactgct 168240
ctggtttgca gattttcttt ccctctcaaa tgaatacaat atgttttcaa gtctcaacca 168300
gatcttgaga aaataggaag agccagaggg tttctttggt gttatggttg tacagcttcc 168360
cagactccgg gggagagatg tgatttgtgc tttctggcaa tcccatggcg tattaaattt 168420

```
tcataggctt tccagtttaa atttagggta ggcaatggaa gggaacgcaa aacagatttc 168480
taggtgtact gtgtgtgtgt ctcccacgtc taaagtctgt taactggagc acccaacagg 168540
ccccacaggc tgccttcaca cagaggacct ggggcgcctc cgacccattg ggtgagcag 168600
tgggccatgg agggagccag ggtcaggaga cctggttgtg ggcctgacct gaccctgctc 168660
agggtggcct caggtgggcc gttcacctcg tcagcctcag cttaccctct gactacagtg 168720
acctcagaca aaatacgctt cctggccctg tccagttctg actttttata aacaagcact 168780
tatccaagtt aaagggatat tttcaatatc tactgagtcc acagatatta aatatctcct 168840
ctcttcttta aaattgtggc attatcttta gaatataaaa ggaaaataac acacactctc 168900
cttgaaaata gagagcctaa acactctgca ggaaatattt aaagctatag tttttgtttg 168960
tttgtcttga atgcaagtgg cctggacttt gacttgcttt gagtctttga ccttcatgac 169020
ttcagtacag ttcaaccctg acagttttga agtaggtatg tgcctagatc tgccctagtc 169080
cctgctggaa tgttgaagaa gcaaaggtcc aggccctcag agcacttgcc acgtacttgc 169140
caacagatac ggggcggaga cttgagtcaa cgtaagagca agtgtgtgcc gggtgatccg 169200
acactgcaga gcgccagcta gaccctaagc gtgtgctagg ggctgaccaa gccgttcttt 169260
cctcaaaaac ttggtgggga gggtattttt aaaatcacac aaatatttaa gtacagatta 169320
tgatgactgc ctcaaagcag tggctcttca gcttcatcaa gcttcagagt ccagagggtt 169380
tgttcatatg gaaggctagg cctgtctcct gcatttcacc ctcttggcct gggggcggga 169440
cccaagaatg tgtggctcta aaaggttccc aggcaatgct gaggctgctt tctgaaggaa 169500
aaactgcaag ataccaggag agtttcattt agattgaaga gtcgaggaag gctcctctga 169560
gaaagagtct gctaaggaag gaggaggtgg gttctgggga cagaggttct cccgtgggta 169620
agggtggagg gaagctctcc tggggagaag gtgggcagga ggaccagagg ctggagggag 169680
gagggcagtc agcctcgggg cttcccagga acagggacgg ccagggcagg gtttagggca 169740
aggaaagcgt gtgagcatat ttgtatttta gtaaatattt acagtttgcc ctccatgtct 169800
gcagtttcat atccatggat tcaatcaacc acaatgaaaa acgttgggga aaaaaattgc 169860
atcggtactg aacatatacg gacttttttt cttgtcatta ttccctaaac aatacagcat 169920
aacaattatt cacatagcat ttgcactgta ttaggtacta taggtaatca ggagatgctg 169980
tagatgggag gatgtctgta ggttacacac aaatgctgtg ccactttata tcaggggctt 170040
gagcatcctc acattttgat atttaaggga ggtcctggaa ccaattcccc agatactgag 170100
ggtccactgt ctgtgtcccc tcgccccacc ttgcctttgt ctcctgtctc ctatctccac 170160
cctgcctccc gccagcctgt tgctcctgac ctgcccgggc accctggagc agcaccctat 170220
ctcagagcct ggctcagtgt gttcacttct gcagagaaac taacttgccc aagtccacac 170280
tcaaaacata ggcattgctg agatgtgaaa agcagctgtg gatgctttct gctacagtct 170340
gtgtgttctt ttccatatct gaataaaagg tcaccaccat ttgtatttta aagagaaaga 170400
gaatttatgg gtggaaattg gggattccct cattctcagt cagacagaaa agagggcccc 170460
attgtgtgcc tgattgcaaa taaatttagc ttcctcagcc caagaatagc agaagggtta 170520
aaataaagtc tgtatttatg gctctgtcaa aggaaggccc ctgccttggc agccagccgg 170580
aattagcagg gcagcagatg cctgactcag tgcagcatgg atttcccata gggagcctgg 170640
gggcacagca cagagagacc acttctcttt agaaatgggt cccgggcagc caggcagcct 170700
ttagtcactg tagattgaat gctctgtcca tttcaaaacc tgggactggt ctattgaaag 170760
```

-continued agcttatcca gctactcttt gcagaggtgc tgtgggcagg gtccccagcc caaatgccca 170820
cccatttccc agagcacagt cagggccaag cctggcctgt ggggaaggga ggcctttctc 170880
cctgctggct cggtgctccc cggatgcctt ctccatcgct tgtcctctgc agcacccaca 170940
gccagcgttc ctgatgtgca gggtcagtca ttacccaggg tgttccggac cccacacaga 171000
ttcctacagg ccctcatgat attttaaaac acagcatcct caaccttgag gcggaggtct 171060
tcataacaaa gatactatca gttcccaaac tcagagatca ggtgactccg actcctcctt 171120
tatccaatgt gctcctcatg gccactgttg cctgggcctc tctgtcatgg ggaatcccca 171180
gatgcaccca ggaggggccc tctcccactg catctgtcac ttcacagccc tgcgtaaacg 171240
tccctgtgct aggtcttttg caggcacagc ttttcctcca tgagtacgta ttttgaaact 171300
caagatcgca ttcatgcgtc ttcacctgga aggggtccat gtgcccctcc ttctggccac 171360
catgcgaagc cacactgacg tgcctctccc tccctccagg aagcctacgt gatggccagc 171420
gtggacaacc cccacgtgtg ccgcctgctg ggcatctgcc tcacctccac cgtgcagctc 171480
atcacgcagc tcatgccctt cggctgcctc ctggactatg tccgggaaca caaagacaat 171540
attggctccc agtacctgct caactggtgt gtgcagatcg caaaggtaat cagggaaggg 171600
agatacgggg aggggagata aggagccagg atcctcacat gcggtctgcg ctcctgggat 171660
agcaagagtt tgccatgggg atatgtgtgt gcgtgcatgc agcacacaca cattccttta 171720
ttttggattc aatcaagttg atcttcttgt gcacaaatca gtgcctgtcc catctgcatg 171780
tggaaactct catcaatcag ctacctttga agaattttct ctttattgag tgctcagtgt 171840
ggtctgatgt ctctgttctt atttctctgg aattctttgt gaatactgtg gtgatttgta 171900
gtggagaagg aatattgctt cccccattca ggacttgata acaaggtaag caagccaggc 171960
caaggccagg aggacccagg tgatagtggt ggagtggagc aggtgccttg caggaggccc 172020
agtgaggagg tgcaaggagc tgacagaggg cgcagctgct gctgctatgt ggctggggcc 172080
ttggctaagt gtcccccttt ccacaggctc gctccagagc cagggcgggg ctgagagagc 172140
agagtggtca ggtagccctg cctgggtgct ggagacaggc acagaacaac aagccaggta 172200
tttcacagct ggtgcggacc cagaaagact tctgcttttg ccccaaaccc ctcccatctc 172260
catcccagtc ttgcatcagt tatttgcact caacttgcta agtcctattt ttttctaaca 172320
atgggtatac atttcatccc attgacttta aaggatttgc aggcaggccc tgtctctgag 172380
aatacgccgt tgcccgtcat ctctctccga cagcagggca gggggtccag agatgtgcca 172440
gggaccagag ggagggagca gacacccacc cggcctgggc aggtcctcct cattgcttgc 172500
atccgcctgg ttagcagtgg cagtcagtcc tgccgagtca ttcgtgaggc gctcacccaa 172560
ctccaggcag atgtaaaagg tgacctacaa gaagacaaac aaaaacatct ggagcgctct 172620
tatgccagca tctgcccttg acaccaccag gcaggctgtt gctgggagcc gtggtgcttg 172680
ggtaagctcc ttcccatggc agagctcctg ggacgcattg tagaagcagg gaccacctcc 172740
caggataacc agatagcagc acaccctgca cagccccttt tactccagca tcatcgggca 172800
ttgatatctc agctgcagcc acaggcggcc cccagcaccc caggaagtgg ggagcgctca 172860
tgcttctctg agcacaaaaa tcactgaata tttttgccat tctcatggtc ataacccggg 172920
ccacagagta gaacactcct atcactgttg ttagacagtg gtcctgggag agggtcttgt 172980
gtgcctcgga tgccagggcc tctttttatt gggaggtgct tgttatttct gtgtgtggct 173040
gcatttgttt cccaagactg ccacaacaaa tcatcaccaa cttggtagct caacatagca 173100
cagctttatt ccctcctggc tctggaggcc aggtgtctaa aaggccatgc tcccacaatg 173160
gttctgagga ggatccttcc tgcctctctg gcttctggtg gctccagcat ccctgggctg 173220
tggctgcacc tccccatgtc aacctccgtc ttcacaaggc cttttcctgt gtctctgcaa 173280
ccacaggccc ctctcctttc tcttaataaa gataccagtc attgagtttg aaaattgcta 173340
agagagtctg ttgtaaatct tcttagcaca aaaaaaaatg acagatatgt gaagtggtag 173400
atatattaat tagtttgatt tgatcactcc gctatgtgta taaatgtcaa aacaaacatt 173460
gcactccata aatatatata ttaaaaaaga tcccagtcat tgcatttagg acccacccta 173520
aatccaggat gatttcattt caagactttt aactagattt gcaaaacccc atttccaaat 173580
aaggtcacat tctgcagttt tgggtagacg tgaaatgtgg agacactgtg caacccactg 173640
tcttggggag ggggtggtca gcctggggca gatgttgctg ggtgtggagc tacatccact 173700
catgccctga cctggaaccc agacctgctt ccccagctct cctcctggtt atctgaagca 173760
gggaatggag agcactgccc tccttgccca ggcagtctct atcacctggt tttagtttct 173820
tcttagcaca tattgcccca gaatatctgg ttggtttatg gcttacttga gtttgtgcct 173880
acctgtccca accgggaggt gagccctggc tattccccaa acccggccct gcatgtggga 173940
gctgcccttc ctccgttcat cagagggggc caacagtcca cagctgttct taatcatctc 174000
ccagtaaccc ccagctccac aaaggtgact ccttacatgg tggagaggtg gtcgggccat 174060
ccgtgtgaaa tgtgtatgtg accgttttcc ttaaggggca cgtagtcttg gcaggtttcg 174120
ctcaatatag gatgagctca ggactccagt ggactgtgga ttcagatctg gattctggcg 174180
cattcgccgt gtgaacgggg gcacgttgct ggcctgtctg cgcctcgtct cccgactgtg 174240
gagtgtgttc tgccccttgt ctttctggga ggtagggagg gcagtgagcc ccttcgcatc 174300
gcccaccaca ggcccagcac atggctgatc cccactgagt gttcttttcc tcctttgatc 174360
ccctttggct gacctaggtt ggagcagcca ctaaaatata cccagaaaca tcttcctaat 174420
ctacatctgt gccaaccctc attccctggc gcagcatgac catcacatgc ccgccattgt 174480
tcctgatctc tgctgctcat gacctgctct ccagcgctcc ttctcatgct cacattccag 174540
ttggcctgac ctagataagt ggaggtttat ttgaccccaa aaattagcct tctacaaacg 174600
aatataatag tgtccattac agagaataaa cttagtgcgt gtcccattta agcagaagtt 174660
actgaaagcc tgagtttaag tttccagggc ctgaaagttt tccatgacag ttttctgcat 174720
aatattacct acaatttcaa tctgttattt aaagccattc ttgtgtttgt tgtactttga 174780
ttagctttat tttgatttga agtcctttta cattacgggc agttaacgct ttgtctctgt 174840
tagatttgct ttttagttca caagagaaac ctcattcctc tgtatttgaa tagttgcaat 174900
gatggaacag ctgtccctgg agggaaatga aaacagtgat tccccaaatt gtgacaatag 174960
aaatttgctc ttgggttact tacaatgtat ctgagtatta aaaaattttc tttttaaacg 175020
tttgaagtaa aactacccag aaacacttag tggctgacca gaaactaaac tcctggcatc 175080
ctcaaaatgg gatttattgg cttataaatg tcctgtgttg actcacaaag gcacaaacta 175140
tctaggtaag ttttcttcta aatgttgatg ggagagctgg ccactgttat gcaagtttca 175200
ttgtcctgac taaactgcca aagagattac ataaaattat atcaactaga caaaaggaaa 175260
aaggaaaaaa aacagaggtg tcttgggagg aatccatatg agaccagtag accatgagag 175320
agacatccct tgccatctac aaggaaaatg gattttgttc tccatatgca aaaccatctc 175380
aggagcttgc ggagacacca cttgcttact agccagaaag agcaggtgcc tcctaaattc 175440
cccacacagg agctcacagt ggctttcatg cactgggatt aagttagact taagaaagcc 175500
tgtctactct tcctgggatt tacaagccag ctagtaaatc ccagaataaa tcacacggca 175560
cagtcatcca aagatcccgt catccgtgcc gtttggaaag ccctgctcct gtgccaccct 175620
ctccccgtgg agcctcccat gcccaggact gcagagtcct gccattcaga ctgcaactca 175680
tctcacattc ttccaaacta tttggacaac agagctttct catcacctaa tgcagattac 175740
agtctcacag aattgagtgt tcaggcagac actgatgtgg ttctgtagta cagcaaacaa 175800
tatcagttta cagtcctgag gccaggcctg gtgaacaacg cacggtagcg gtggggcagg 175860
gttctcagaa tgaaactggc ttacacatgg cactctctga ccacaactgt ataagcacca 175920
aactacactt agttccatct atgaggtaaa atttaatgca gatgaacatc aaagaaaacg 175980
tcaaaggctc ctttttacaa gtacgtgggc tacttaattt ggtccaagtc cattttaaaa 176040
agccctaggt gctttcacgg ctctgctact gacaagaagc cccagtgcct gtgagctgct 176100
aatgggaggg agaggaagat gagctgagtg ggccgggcta tcccgtccac accgggagac 176160
agggaaggag actccaagct ggtggtgcca gcacattcca ggccactcag gcctattcct 176220
aggtgccagg tcacgaaaac cacgctgaca gatcgtgctg tgtgcgtgtc atagcacaca 176280
agcaggactg tgagagagtg aaagtgacac tgggtggagc actgaggaag ggccacagtg 176340
tgttggtgga gataggctgt catggagaag agaccctggc ttgctctaca ttgcttccaa 176400
tgcaactgca aggcaggtcc cagagggctc cggccttcgt catccaggtt tgctccctcc 176460
cctcatggct ttcccatcct cagatgagga ctcggcagag cctacccctg ctgactaact 176520
gtggccccag ggtggtgact cagccctgca cctcctgatc ccgtctgcac tgggccagag 176580
aggatgactt acccagcacg ttcacatcac acagctttgt ggattcctag gtccaaggac 176640
cagagatttc agttatgtga gttatttttt ttatttgttc ttgcgtattc cacaaagggt 176700
cgcagctaaa cttaacctaa tgatcacttt agtatatcac taaaaagaca aagctcacag 176760
tgctgttgaa gcacattcat catctttaga cattttgact agttatttct taagcattta 176820
cctgctagtg ttaagcatca catgaaatac atatagaagt aagacaaaat ttcttatctc 176880
cccaagtttg ccaacaaata cagagcagga agggaagcag gtcagagcag gaggcgcagc 176940
tatagtgagg ccaccatgca aggcacaggg agggtgagct ccaagtttga atggaatggg 177000
tctgtcagcc aagccccctg gctctgggaa gatagcagtg aacaagccag atggcccctc 177060
accctccaga gccgtgagtc ctgcagacca aacagcgtga caggtccttt ccctgtccag 177120
gaggcctctg tgggtgagag ttggctgcgg acagggcgtg aaggcacttg agggtgggga 177180
agtgactctg actgggagat gctgaggaca gggaggaaac caccagataa gggacactgg 177240
ggaggagggg tggacccctc agggccaagc acatggagcc tcatcacaaa ggcaagatgg 177300
tggccaaatt caaggtcgct gcaaaaggaa tggagaagag agaatagatt tggcatttgg 177360
aggaaatggt gacaatcatg agcacctacc cgggactctc catgggtgct atctctacat 177420
aaactcattc caccctctga ttaatccatt ctacatatgg ggaaacaaag gcatgcggtg 177480
tttacgtcac ttgccaagat ctcaggattt gatccaggtg gcctggttcc atggtgcagc 177540
ctctcagcct gcatggatgc cccagctcag agcatgactc tcaggacagg ggtcccagca 177600
gccctccctc cctgagcagc agggtgcccg tgctgcacca cttctgtcta ggaataggac 177660
attctgacac tttcctgcct cttccgaggt ctagcactta ctctatgcct gcctgggaag 177720
gtggcaagct ggcctgagga acagactctt ccattttttta gggagctcaa ggccacagat 177780
gctctgagat ctggagtcca gagacaggag cggaggcttc tcctggtgac cactctgctt 177840
aaaaacttca tcagatccgt agtttcagag cccccctgaa ccccatccct tacctctacc 177900
agttgcaggt gggtctctgg ggtggggctg ccctccccac cagcacccca agggctaaaa 177960
ggttgagggg agaacaccat catttgtaca gggggatc 177998

<210> SEQ ID NO 27
<211> LENGTH: 21
<212> TYPE: DNA
<213> ORGANISM: Homo sapiens
<220> FEATURE:
<221> NAME/KEY: misc_feature
<223> OTHER INFORMATION: EGFR exon 1 forward primer

<400> SEQUENCE: 27
ctcctcgggg agcagcgatg c 21

<210> SEQ ID NO 28
<211> LENGTH: 20
<212> TYPE: DNA
<213> ORGANISM: Homo sapiens
<220> FEATURE:
<221> NAME/KEY: misc_feature
<223> OTHER INFORMATION: EGFR exon 9 reverse primer

<400> SEQUENCE: 28
ccacacagca aagcagaaac 20

<210> SEQ ID NO 29
<211> LENGTH: 26
<212> TYPE: DNA
<213> ORGANISM: Homo sapiens
<220> FEATURE:
<221> NAME/KEY: misc_feature
<223> OTHER INFORMATION: EGFR patient 1 breakpoint forward primer

<400> SEQUENCE: 29
catgatgttt aattattaga ggactc 26

<210> SEQ ID NO 30
<211> LENGTH: 18
<212> TYPE: DNA
<213> ORGANISM: Homo sapiens
<220> FEATURE:
<221> NAME/KEY: misc_feature
<223> OTHER INFORMATION: EGFR patient 1 breakpoint reverse primer

<400> SEQUENCE: 30
aagcaaggca aacacatc 18

<210> SEQ ID NO 31
<211> LENGTH: 24
<212> TYPE: DNA
<213> ORGANISM: Homo sapiens
<220> FEATURE:
<221> NAME/KEY: misc_feature
<223> OTHER INFORMATION: EGFR patient 7 breakpoint forward primer

<400> SEQUENCE: 31
tctaggccgc aatgtggaca atac 24

<210> SEQ ID NO 32
<211> LENGTH: 24
<212> TYPE: DNA
<213> ORGANISM: Homo sapiens
<220> FEATURE:
<221> NAME/KEY: misc_feature
<223> OTHER INFORMATION: EGFR patient 7 breakpoint reverse primer

```
<400> SEQUENCE: 32

acagtggctc atgcctgtaa tctc                                          24


<210> SEQ ID NO 33
<211> LENGTH: 26
<212> TYPE: DNA
<213> ORGANISM: Homo sapiens
<220> FEATURE:
<221> NAME/KEY: misc_feature
<223> OTHER INFORMATION: Fusion of exon 1 and exon 2 in WT EGFR

<400> SEQUENCE: 33

ggaggaaaga agtttgccaa ggcacg                                        26


<210> SEQ ID NO 34
<211> LENGTH: 29
<212> TYPE: DNA
<213> ORGANISM: Homo sapiens
<220> FEATURE:
<221> NAME/KEY: misc_feature
<223> OTHER INFORMATION: Fusion of exon 7 and exon 8 in WT EGFR

<400> SEQUENCE: 34

tgaagaagtg tccccgtaat tatgtggtg                                     29


<210> SEQ ID NO 35
<211> LENGTH: 28
<212> TYPE: DNA
<213> ORGANISM: Homo sapiens
<220> FEATURE:
<221> NAME/KEY: misc_feature
<223> OTHER INFORMATION: Exemplary fusion of exon 2 and exon 8 in
      patient with EGFRvIII mutant gene

<400> SEQUENCE: 35

ggaggaaaag aaaggtaatt atgtggtg                                      28
```

METHODS FOR DETECTION AND QUANTIFICATION OF EGFRVIII IN THE PERIPHERAL BLOOD OF GBM PATIENTS

RELATED APPLICATION

This application is a divisional of U.S. application Ser. No. 14/675,400, filed Mar. 31, 2015, and claims priority under 35 U.S.C. § 119(e) to U.S. Provisional Application Ser. No. 61/972,461, filed Mar. 31, 2014, which applications are hereby incorporated by reference in their entirety.

TECHNICAL FIELD

The presently disclosed subject matter relates to methods and kits for monitoring the therapy of a patient suffering from glioblastoma multiforme (GBM). More specifically, the presently disclosed subject matter relates to methods and kits for monitoring the therapy of a GBM patient that is positive for the epithelial growth factor receptor vIII (EGFRvIII) gene.

BACKGROUND OF THE INVENTION

Glioblastoma multiforme (GBM) is the most aggressive brain tumor in adults and remains incurable despite multimodal intensive treatment regimens. Brain tumors can be difficult to biopsy due to their high-risk location relative to vital structures of the brain or patient related co-morbidity. A very limited number of patients are re-biopsied or re-resected when they relapse after the initial therapy. The management of these patients also poses many problems as follow up of patients with brain tumor is limited to radiological techniques such as magnetic resonance imaging (MRI). Even with the addition of the last generation of imaging studies (spectro-MRI, PET-CT), clinical assessment of tumor progression versus pseudo-progression remains difficult. This can pose serious delays in treatment decision and result in harm to the patient. Management of patients with brain tumor is problematic as it is limited to radiological techniques and clinical assessment of tumor progression versus pseudo-progression remains difficult.

The use of tumor-specific rearrangements to monitor the status of the disease may improve the clinical management of brain tumor patients. EGFRvIII is a truncated extracellular mutant of the epithelial growth factor receptor (EGFR) commonly found in GBMs that confers enhanced tumorigenic behavior. GBM patients testing positive for EGFRvIII have a bleaker prognosis than those who don't. Virtually no EGFRvIII-positive patient survives two years, versus about 15% of those who are EGFRvIII-negative. EGFRvIII is tumor specific and is present in about one third of brain tumor cases. Thus, it potentially represents an ideal mutation to follow and quantify in the peripheral blood of patients on treatment. However, detecting this mutation in the genomic DNA is challenging as the deletion breakpoint is different from one patient to another. Thus, the need exists for new methods and kits that allow for the detection and monitoring of EGFRvIII in patients suffering from GBM.

SUMMARY

Accordingly, it is an object of the present invention to provide method for monitoring the therapy of a patient suffering from GBM, comprising: (a) subjecting a sample from the patient comprising genomic DNA to long range polymerase chain reaction amplification of epithelial growth factor receptor vIII (EGFRvIII) gene, wherein the long range polymerase chain reaction amplification utilizes a plurality of forward primers corresponding to a DNA sequence in intron 1 of an epithelial growth factor receptor (EGFR) gene and a reverse primer that corresponds to a DNA sequence in exon 8 of an EGFR gene, such that if the sample comprises genomic DNA comprising EGFRvIII, a PCR product is formed, and if the test sample does not comprise genomic DNA comprising EGFRvIII, a PCR product is not formed, wherein the plurality of forward primers are comprised within the base pairs defining intron 1 of the EGFR, each primer being separated by at least 5 kb from each other, and wherein the presence of PCR product is indicative of a presence of EGFRvIII in the test sample, and the absence of PCR product is indicative of an absence of EGFRvIII in the test sample; (b) identifying deletion breakpoints in the PCR product and designing amplification primers that hybridize to priming sites that flank the breakpoints, wherein the amplification primers are designed to yield a PCR fragment of about 300 base pairs; and (c) amplifying DNA from body fluid samples of said patient using the amplification primers to form an amplified DNA fragment of EGFRvIII.

In another embodiment, a kit is provided, the kit comprising a plurality of forward primers corresponding to a DNA sequence in intron 1 of an EGFR gene and a reverse primer that corresponds to a DNA sequence in exon 8 of an EGFR gene, wherein the plurality of forward primers are comprised within the base pairs defining intron 1 of the EGFR gene, each primer being separated by at least 5 kb from each other.

In another embodiment, a kit is provided, the kit comprising one or more amplification primers that hybridize to priming sites that flank breakpoints in EGFRvIII, wherein the one or more amplification primers are designed to yield a PCR fragment of about 300 base pairs.

These and other objects, features, embodiments, and advantages will become apparent to those of ordinary skill in the art from a reading of the following detailed description and the appended claims.

BRIEF DESCRIPTION OF THE DRAWINGS

FIG. 1 depicts the data analysis pipeline used that allows detection of structural variations, single nucleotide polymorphisms, as well as copy number variations.

FIG. 2A depicts that genomic DNA structure of EGFRvIII mutant gene compared to wild type EGFR gene. FIG. 2B depicts EGFRvIII protein showing the ligand binding domain deletion. FIG. 2C depicts sequencing result of wild type and mutant genes showing the fusion of exon 1 and exon 2 in WT cDNA (SEQ ID NO 33), the fusion of exon 7 and exon 8 in WT cDNA (SEQ ID NO 34), and the fusion of exon 1 to exon 8 in the EGFRvIII cDNA (SEQ ID NO 35). FIG. 2D. depicts detection of EGFRvIII patients using RT-PCR.

FIG. 3A depicts a schematic representation of the EGFRvIII genomic DNA showing the loss of exons 2 through 7, the location of Alu sites in introns 1 and 7 involved in recombination, and a schematic of the forward primers used in the long-range PCR-based strategy that span the whole intron 1 and a reverse primer in exon 8. FIG. 3B and FIG. 3C depict the result of long range PCR amplifications showing specific bands in patients 1 and 7, respectively, but not in WBCs. The desired bands produced using Set B of primers are shown. Asterisk indicates a nonspecific band. FIG. 3D shows Sanger sequencing demonstrating that EGFRvIII deletion can also involve intergenic recombinations.

FIG. 4A & FIG. 4B depict two EGFRvIII deletions, starting at two different locations in intron 1, that were detected in patient 7. FIG. 4C depicts that both deletions in patient 7 end at one site in intron 7. FIG. 4D and FIG. 4E depict that one of the deletions in patient 7 involved an intragenic recombination with SEPT14 and Sec61G genes, two genes adjacent to EGFR.

FIG. 5A depicts the detection strategy of the EGFRvIII deletion by PCR. FIG. 5B depict PCR amplification of the deletion from genomic DNA using primers adjacent to the breakpoint. FIG. 5C depicts detection of the EGFRvIII deletion in the plasma of patient 7 before and after surgery. FIG. 5D depicts detection of the EGFRvIII deletion in the plasma of patient 1 before and after surgery. The quality of the circulating tumor DNA is variable between patients due to a difference in time between the blood draw and DNA extraction.

DETAILED DESCRIPTION

Figure 1:
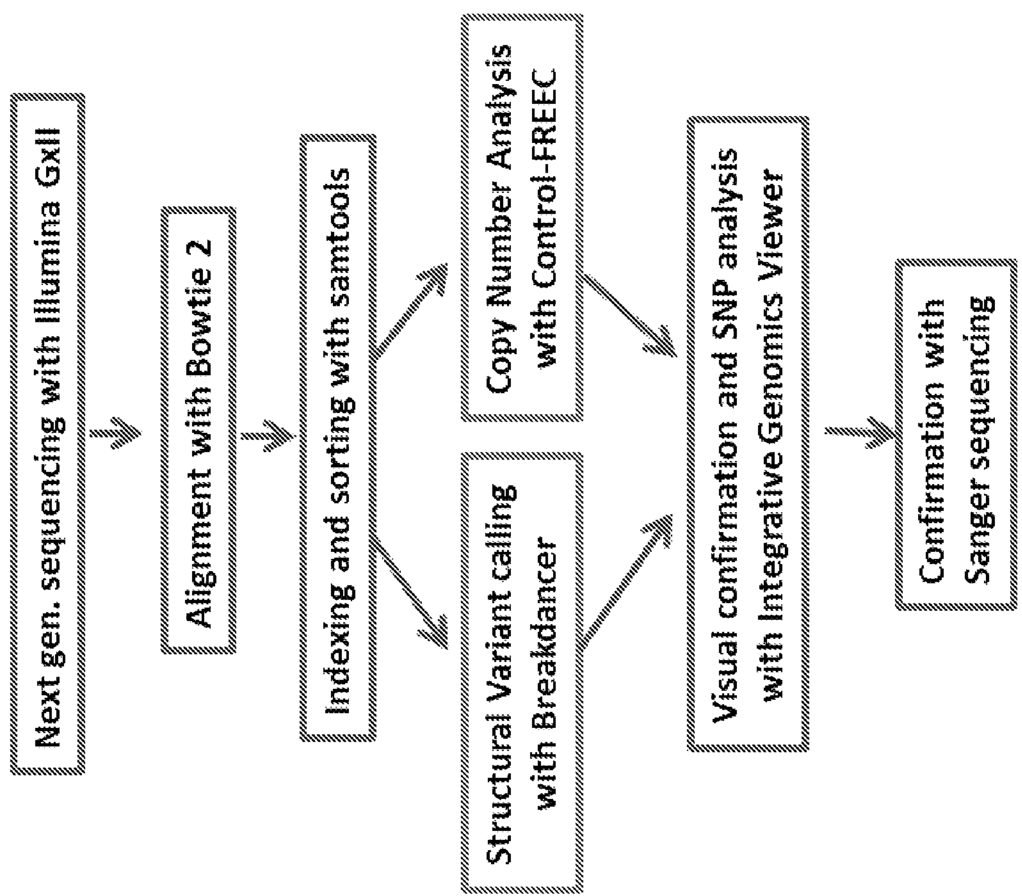
FIG. 1. Whole genome sequencing data analysis pipeline.

Particular details of various embodiments of the invention are set forth to illustrate certain aspects and not to limit the scope of the invention. It will be apparent to one of ordinary skill in the art that modifications and variations are possible without departing from the scope of the embodiments defined in the appended claims. More specifically, although some aspects of embodiments of the present invention may be identified herein as preferred or particularly advantageous, it is contemplated that the embodiments of the present invention are not necessarily limited to these preferred aspects.

Unless defined otherwise, all technical and scientific terms used herein have the same meaning as commonly understood by one of ordinary skill in the art to which the presently-disclosed subject matter belongs.

There is an urgent need for sensitive personalized biomarkers to accurately monitor residual and recurrent tumors and enhance the clinical management of GBM patients. No biomarkers are currently available to follow brain tumor patients on treatment. There is a strong interest in exploiting somatic mutations, which occur exclusively in the tumor, to develop such biomarker. One such mutation is the EGFRvIII deletion. Approximately 33% of all high-grade gliomas express EGFRvIII, and it is a bona fide tumor-specific antigen with potent oncogenic properties (20). It results from an in-frame deletion of 801 bp spanning exons 2 to 7 of the coding region of EGFR and leads to ligand-independent tyrosine kinase activity that activates persistent downstream phosphatidylinositol 3-kinase (PI3-K) pathway. The use of genomic DNA to detect the EGFRvIII mutation is complex due to the presence of several recombination sites in intron I (123 kB) and in intron 7 of EGFR gene. These sites are involved in DNA recombination events that generate genomic deletions of varying sizes leading to structural differences between GBM patients. Thus, detecting this mutation in the genomic DNA is challenging as the deletion breakpoint is different from one patient to another, although the mRNA is similarly spliced in every patient and the resulting truncated protein is the same in every patient.

To address this problem, we used a long range PCR amplification strategy that allows detection of all possible EGFRvIII deletions. The presently disclosed data demonstrates that our long range PCR strategy can be successful in detecting EGFRvIII deletion without the need to sequence the whole genome of the patient, which can be costly and time consuming. These deletions were confirmed using next generation sequencing in one of the EGFRvIII patients. Additionally, we developed a strategy to detect EGFRvIII mutation in the circulating tumor DNA and investigated the utility of tracking the tumor-derived EGFRvIII mutation in the peripheral blood as a way to monitor GBM tumor dynamics in patients on treatment. The presently-disclosed data also demonstrates that quantification of the EGFRvIII mutation in the plasma can be a useful tool to monitor brain tumor dynamics in patients on treatment. We collected blood just before surgery and 3 weeks after surgery. The blood was used to isolate both plasma for circulating DNA extraction and white blood cells (WBC) for extracting the constitutional DNA control. Genomic DNA (gDNA) from the tumor was extracted, and together with gDNA from WBC, was used to determine the location of the EGFRvIII deletion. The deleted area was confirmed using next generation, paired end sequencing. Sanger sequencing was used to determine the breakpoints and primers spanning the breakpoints were used to PCR amplify through the deleted fragment in the gDNA from both tumor and plasma. The data suggest that the amount of circulating mutant EGFRvIII DNA correlates with the status of the tumor and could be used as a noninvasive biomarker to monitor disease status in patients on treatment.

In some embodiments of the presently-disclosed subject matter, a method for monitoring the therapy of a patient suffering from glioblastoma multiforme (GBM) is provided. In certain embodiments, the method comprises subjecting a sample from the patient comprising genomic DNA to long range polymerase chain reaction amplification of epithelial growth factor receptor vIII (EGFRvIII) gene. A "patient" refers to an individual that is suffering, or suspected to be suffering, with cancer. In specific embodiments, the individual is suffering, or suspected to be suffering, from GBM. The term "samples" refers to any biological material collected from an individual, and can include whole blood, plasma, serum, lymph, spinal fluid, tissue, and in particular, tumor containing tissue, such as tissue derived from a biopsy or obtained after surgery.

PCR amplification is a well-known tool in the art for amplification of nucleotide sequences. In certain embodiments, the PCR is real time PCR technique allowing simultaneous detection of the amplified product. Real time PCR techniques are well known in the art. The primers used in PCR are designed to anneal to the denatured target DNA sequence strands in a position and orientation such that the extended primers are complementary copies of the target DNA sequences. On subsequent amplification cycles, the extended primers can also serve as targets for amplification. Long range PCR is also well-known in the art, and utilizes amplification conditions which improve target strand denaturation (e.g., higher denaturation temperatures, addition of cosolvents), and which protect DNA from degradation; utilizes longer extension times; and minimize incorporation of erroneous nucleotides by utilizing polymerases having exonuclease activity to reduce mismatches, thereby enabling amplification of extended strands of DNA. Long range PCR has been used for the sequencing and analysis of EGFRvIII deletions (Frederick. L, Eley. G, Yang-Wang. X, James. C. (2000); "Analysis of genomic rearrangements associated with EGFRvIII expression suggests involvement of Alu repeat elements". *Neuro Oncology;* 2000; 2:159-169), the entire teachings of which are incorporated herein by reference.

In some embodiments of a method for monitoring the therapy of a patient suffering from glioblastoma multiforme (GBM), the long range polymerase chain reaction amplification utilizes a plurality of forward primers corresponding to a DNA sequence in intron 1 of an epithelial growth factor receptor (EGFR) gene and a reverse primer that corresponds to a DNA sequence in exon 8 of an EGFR gene. DNA/RNA is within the scope of our recitations if they are within 98, 95, 90, or 80% sequence homogeneity with the sequences set forth as SEQ ID NO 26 (*Homo sapiens* EGFR sequence, GenBank Accession #AC006977), as well as the sequence for intron 1, exon 1, intron 7, and exon 8 of human EGFR, as is known in the art (see for e.g., Reiter, J. L. et al (2001); "Comparative Genomic Sequence Analysis and Isolation of Human and Mouse Alternative EGFR Transcripts Encoding Truncated Receptor Isoforms". Genomics; 2001; 71: 1-20), the entire teachings of which are incorporated herein by reference).

In certain embodiments, the plurality of forward primers is comprised within the base pairs defining intron 1 of the EGFR, with each primer being separated by at least 5 kb from each other (as is schematically depicted in FIG. 3A). As is known in the art, a primer refers to an oligonucleotide that is capable of serving as an initiation point for nucleic acid synthesis during PCR or long-range PCR, under appropriate conditions. Primers can be prepared by a variety of methods that are well known in the art, including chemical synthesis. As is known in the art, a forward primer is a primer that hybridizes to the non-coding strand of the target DNA and forms the 5' end of the amplified product of the coding strand), and a reverse primer is a primer that hybridizes to the coding strand of the target DNA and forms the 5' end of the amplified product of the non-coding strand. A primer "corresponding to" a DNA sequence is a primer that has the same nucleotide sequence as the DNA sequence, or that is sufficiently complementary to the DNA sequence that it hybridizes under PCR (including long-range PCR, real time PCR, etc.) conditions to the DNA sequence.

In certain embodiments of a method for monitoring the therapy of a patient suffering from glioblastoma multiforme (GBM), if the sample comprises genomic DNA comprising EGFRvIII, a PCR product is formed, and if the sample does not comprise genomic DNA comprising EGFRvIII, a PCR product is not formed. In some embodiments, the presence of PCR product is indicative of a presence of EGFRvIII in the test sample, and the absence of PCR product is indicative of an absence of EGFRvIII in the sample. Thus, in certain embodiments, the primers are designed such that no PCR products are produced in the absence of EGFRvIII. For example, the primers will yield PCR products of a certain size in the presence of the EGFRvIII, and will yield no PCR products in the absence of EGFRvIII. Alternatively, the primers can be designed such that the PCR products obtained from the primers will differ in size, depending on the presence or absence of EGFRvIII. That is, in the presence of EGFRvIII, the primers will yield PCR products of a certain (first) size, and in the absence of the EGFRvIII, the same primers will yield PCR products of a (second) size that is detectably different from the size of the PCR products in the presence of EGFRvIII (the first size). The detection of EGFRvIII is indicative of the presence of precancerous or cancerous lesions.

The term, "PCR products," refers to copies of the target DNA sequences that are produced during PCR amplification (i.e., DNA which has been amplified during the PCR process). If no DNA has been amplified during PCR, no PCR products will be generated. Analysis of the PCR products includes detecting the presence (or absence) of detectable PCR products; in a preferred embodiment, analysis of the PCR products includes determining the size of any detectable PCR products. A detectably different size indicates that the differences in the sizes of the products can be identified, using standard techniques as known in the art. The PCR products can be detected by a variety of methods that are well known in the art. For example, gel electrophoresis (e.g., agarose or acrylamide gel electrophoresis), or HPLC, can be used to separate PCR products based on the size of the DNA, and can followed by detection of the size fractionated DNA by methods such as staining (e.g., with ethidium bromide), or hybridization of labeled probes. Detection can also be conducted directly during amplification, such as with real-time PCR and melt curve analysis using cyber green as a labeling agent.

In some embodiments of a method for monitoring the therapy of a patient suffering from glioblastoma multiforme (GBM), the plurality of forward primers comprise one or more primers for detecting breakpoints in EGFRvIII selected from the primers set forth in Table 1. "Breakpoints" are one or more boundaries of a somatic rearrangement, and such breakpoints can be specific markers for the tumor. Identifying a boundary can be accomplished by a number of techniques known in the art. For example, one technique involves sequencing and/or analyzing two different portions or ends of a single fragment of genomic DNA from a tumor. The two portions or ends may be separated by any distance, from immediately adjacent up to 1 kb, 1.5 kb, 2 kb, or 3 kb, for example. The ends may not be the literal ends of a fragment, but may be close to the ends or merely two non-overlapping portions. The sequence of the two ends may be determined separately, for example from either end, or the sequence can be determined in one direction and analyzed for separate, non-overlapping segments of differing copy numbers.

In some embodiments of a method for monitoring the therapy of a patient suffering from glioblastoma multiforme (GBM), the method further comprises identifying deletion breakpoints in the PCR product and designing amplification primers that hybridize to priming sites that flank the breakpoints. The amplification primers are designed to yield a PCR fragment of about 300 base pairs. The identification and design of amplification primers that hybridize to priming sites that flank breakpoints is described in detail, for example in U.S. Pub. No. 2013/0210645, the entire teachings of which are incorporated by reference herein.

In certain embodiments, the method further comprises amplifying DNA from body fluid samples of said patient using the amplification primers to form an amplified DNA fragment of EGFRvIII. The term "body fluid" can include whole blood, plasma, serum, and spinal fluid. In more particular embodiments, the method further comprises determining the amount or proportion of the amplified DNA fragment of EGFRvIII in the body fluid samples of said patient. Thus, the methods can be used to obtain qualitative or quantitative results. The quantitative results can be absolute amounts or relative amounts, for example, compared to a non-rearranged sequence on the same or a different chromosome. In particular embodiments, the DNA is circulating DNA, plasma DNA, or serum DNA.

In further embodiments of a method for monitoring the therapy of a patient suffering from glioblastoma multiforme (GBM), the method comprises a streamlined assay based on high-throughput real-time q-PCR. For example, a glass microfluidic chip can be used to carry out continuous-flow, droplet-based PCR reactions. To generate droplets, a syringe pump is used to infuse the aqueous sample into a channel on the chip. To carry out PCR, the chip is mounted on two static heaters that divide it into two thermal zones, a 95° C. zone and a 67° C. zone. The droplets are conveyed through the chip by the flow of oil, and the static thermal zones provide hot start activation and 35 cycles of two-step PCR. The PCR microchip is stationed above an optical system that combines a video camera with a two-wavelength laser excitation and detection system. Using this optical system, droplets are interrogated at specific neckdowns, 100-μm-long regions of the chip where the channel width and depth decrease, forcing droplets into a single file. Since the diameter of the droplets is the same as the width and depth of the neckdowns, only a single droplet can fit through a neckdown at one time, and no droplets can be missed by the lasers. A fluorescent dye, such as Alexa Fluor 594, provides a constant signal in each droplet that is used for droplet detection. In addition to the Alexa dye, a FAM-labeled Taqman probe that is specific to a region of the amplified EGFRvIII sequence is added to the reaction mix. Fluorescence of the FAM dye on the probe is detected under the fluorescence resonance energy-transfer process when released from its proximity to a quencher by the exonuclease activity of the DNA polymerase, providing a fluorescence intensity increase proportional to the EGFRvIII DNA concentration in the droplet, allowing quantification of the EGFRvIII mutant.

The methods can be used for a variety of purposes. For example, patients can be monitored over time to see if a tumor is in remission or is progressing, the methods can be used before, during, and/or after a therapy regimen, the methods can be used to assess surgical efficacy, and the methods can be used to monitor for relapse or recurrence. In some embodiments, the presence of an amount of amplified DNA fragment indicates residual GBM. In certain embodiments, the step of determining is performed with bodily fluid samples obtained from the patient at a plurality of times. In additional embodiments, the plurality of times is during anti-tumor therapy, before and after surgery, during patient treatment to monitor a patient undergoing anti-EGFRvIII therapy, or the plurality of times are to monitor a patient in remission or relapse of GBM. "Therapy" is defined to include a patient undergoing diagnosis for detection of EGFRvIII, as well as patients undergoing surgical tumor resection, and novel anti-EGFRvIII treatments, including but not limited to, vaccines, antibody-toxin conjugates, EGFRvIII-specific tyrosine kinase inhibitors, as well as other treatments that target EGFRvIII or EGFRvIII protein. Therapy also includes patients being monitored over time to see if a tumor is in remission or is progressing. The methods can be used before, during, and/or after a therapy regimen.

Other deletions commonly present in brain tumors can be used the same way we used the EGFRvIII deletion. One such deletion is the CDKN2A in the 9p21.3 region which occurs in approximately 31% to 50% of GBMs and the ERRFI deletion in the 1p36.23 region which occurs in about 35% of GBM tumors. Besides large deletions, single nucleotide mutations in genes such as IDH1, Tp53, and PIK3CA are also common in brain tumors and can be quantified in the plasma.

In further embodiments of the presently-disclosed subject matter, a kit is provided. In certain embodiments, the kit comprises a plurality of forward primers corresponding to a DNA sequence in intron 1 of an EGFR gene and a reverse primer that corresponds to a DNA sequence in exon 8 of an EGFR gene. The plurality of forward primers are comprised within the base pairs defining intron 1 of the EGFR gene, each primer being separated by at least 5 kb from each other. In certain embodiments, the kit further comprises a forward primer for exon 1 of EGFR. In more particular embodiments, the forward primer for exon 1 has the nucleotide sequence (5'-GTCCGCTCTCGAGGAAAGAAA-3') (SEQ ID NO 1). In other particular embodiments of the kit, the reverse primer that corresponds to a DNA sequence in exon 8 of EGFR has the nucleotide sequence (5'-CTTCCTCCATCTCATAGCTGTCGG-3') (SEQ ID NO 2). In certain embodiments of the kit, the plurality of forward primers are selected from primers set forth in Table 1.

In further embodiments of the presently-disclosed subject matter, a kit is provided that comprises one or more amplification primers that hybridize to priming sites that flank breakpoints in EGFRvIII, wherein the one or more amplification primers are designed to yield a PCR fragment of about 300 base pairs. Thus, the primers to be used in plasma are typically designed within 150 base pairs from each side of the breakpoint.

Preferably, the kits further contain nucleic acid polymerase (including long range high fidelity polymerase), dNTP, buffer, and any other reagents necessary to perform PCR, long range PCR, and RT-PCR, as is known in the art. If required, the kits can further contain a sample containing EGFRvIII as a positive control and/or instructions to use the kit, how to prepare the samples, what kind of samples to use, how to analyze and interpret the results, etc. especially, the test kit can comprise instructions, how to use the test kit for detection of the presence or absence of cancer cells expressing EGFRvIII.

Thus, the test kits according to the present invention, allow determining the absolute concentration or the relative concentration or the presence or absence the amplified DNA fragment of EGFRvIII. The test kit can be used to diagnose the absence or presence of cells expressing EGFRvIII. Further, the test kit can be used to predict the occurrence or to predict the grade or stage of the cancer and/or to predict and/or monitor the success of an anti-therapy EGFRvIII for said cancer and/or predict and/or monitor a relapse of said cancer.

EXAMPLES

The following examples are given by way of illustration and are in no way intended to limit the scope of the present invention.

Example 1

Materials and Methods

Patients and Tumor Samples

Eleven patients newly diagnosed with GBM and planned for surgery, consented to obtain tumor tissue as well as immediate pre-operative blood and 3 weeks delayed post-operative blood. Blood samples were processed immediately for plasma separation and white blood cell (WBC) isolation. Plasma, WBCs and tumor tissue snap-frozen in OCT were stored at −85° C. until used.

RNA Extraction and RT-PCR Amplification

Total RNA was extracted from about 3 $mm^2$ sections using "illustra triplePrep Kit" (GE Healthcare Bio-Sciences Corp). Complementary DNA (cDNA) was reverse transcribed from RNA in 20 μL volume reactions using the "iScript cDNA Synthesis Kit" (Bio-Rad Laboratories, Inc, Hercules, Calif.) according to the manufacture's protocol. The resulting cDNA was used in PCR amplifications in 50 μL volume reactions using "GoTaq Green Master Mix" from Promega Corporation (Madison, Wis.) to determine the EGFRvIII status for each tumor tissue. A forward primer from exon 1 (5'-CTCTTCGGGGAGCAGCGATGC-3') (SEQ ID NO 27) and a reverse primer from exon 9 (5'-CCACACAGCAAAGCAGAAAC-3') (SEQ ID NO 28) of EGFR gene were used in the reaction (IDT Integrated DNA Technologies", Coralville, Iowa). Approximately, 30 ng of cDNA and 130 ng of primers were used in the PCR reaction. Reaction profiles consisted of a 5-minute sample denaturation at 94° C., followed by 35 cycles of 30-second denaturation at 94° C., 30-second annealing at 59° C., and 50-second extension at 72° C., followed by a final 7 minutes synthesis step at 72° C. Products of the reaction were then electrophoresed in 1% agarose gel and stained with ethidium bromide. The resulting gel bands were excised, purified using "Wizard SV Gel and PCR Clean-Up System from Promega Corporation (Madison, Wis.) and were subject to Sanger sequencing using the same forward and reverse primers that yielded the band to validate the EGFRvIII status.

Genomic DNA Extraction and Long Range PCR Amplification

Genomic DNA (gDNA) was extracted from frozen tumor tissue using "illustra triplePrep Kit" (GE Healthcare Bio-Sciences Corp). For long range PCR amplification, two sets of forward primers: set A containing 13 primers and set B containing 12 primers were designed to be 5 kb apart from each other and spanning the length of intron 1 of EGFR gene, as depicted in FIG. 3A. Table 1 lists all the primers used and their location in the genome. Exon 1 forward primer, 5'-GTCGGGCTCTCGAGGAAAAGAAAG-3' (SEQ ID NO 1), is included in both set A and set B. Sequence numbering is based upon GenBank Accession #AC006977 (SEQ ID NO 26). The reverse primer was placed in exon 8. PCR reactions on gDNA were carried out using "GoTaq Green Master Mix" from Promega Corporation (Madison, Wis.) supplemented with 0.5 μL of Crimson LongAmp Taq DNA polymerase (2,500 U/ml) from New England BioLabs Inc. The following PCR steps were used: 5-minute sample denaturation at 94° C.; followed by 45 cycles of 30-second denaturation at 94° C., 45-second annealing at 57° C., and 6 minute extension at 68° C.; followed by a final 10-minutes synthesis step at 68° C. Approximately 10.5-12 ng of gDNA and 0.1 μg/μL of primers were used in each reaction. The PCR products gel were purified using "Wizard SV Gel and PCR Clean-Up System" and were subject to Sanger sequencing to determine the deletion breakpoint.

TABLE 1

| |
|---|
| **Exon 1 forward primer:** |
| 1. GTC GGG CTC TGG AGG AAA AGA AAG (exon 1) (9449-9472) (SEQ ID NO 1) |
| **Set A Primers** |
| 1. GAG TCG AAT TCC CAA CTG AGG GAG (12737-12396) (SEQ ID NO 3) |
| 2. GTG GAG GCT AAA TGG GCC TAA AGG (22361-22484) (SEQ ID NO 4) |
| 3. CTG ATT GAA CCT TCC CAG AGC TGG (32458-32481) (SEQ ID NO 5) |
| 4. GTA TCT GCC CAG AAA GCT CTA CCG (39336-39359) (SEQ ID NO 6) |
| 5. CTG CCT TGC ATG AGA CAC ACA TCC (42376-42399) (SEQ ID NO 7) |
| 6. CCC CCA TGT ACC CCT TTC TTA ACC (52517-52540) (SEQ ID NO 8) |
| 7. CTA CAT GCC CCT CCC TTT CCT TTC (72411-72434) (SEQ ID NO 9) |
| 8. GTA TTT GAG AAG CCC AGG AGT GCC (82388-82411) (SEQ ID NO 10) |
| 9. GAC CCC TAC TGG AAA GAT TCC CAC (92309-692332) (SEQ ID NO 11) |
| 10. CCA GCT TAG ACA GCA GTT CTG CAG (102263-102286) (SEQ ID NO 12) |
| 11. GCC TCA CAT CGT TAG TGT TCC CTC (112426-112449) (SEQ ID NO 13) |
| 12. CAT CTT GGG CTA GGG GTG GAT ATG (122310-122333) (SEQ ID NO 14) |
| **Set B Primers** |
| 1. CCT TAA GGA CAG GCA AAG GTG TCC (18526-18549) (SEQ ID NO 15) |
| 2. CTG ACC CCT AAG GAG CCT GTA ATC (27420-27443) (SEQ ID NO 16) |
| 3. CCC TGC TCA GAA TGT AGG CCT TAC (38416-38439) (SEQ ID NO 17) |
| 4. GAA GAT TGC TTG TGT CTG CGT GTC (58623-58646) (SEQ ID NO 18) |
| 5. GTG TTC CTG TCC TGG GGT ATT TGG (68243-68266) (SEQ ID NO 19) |
| 6. CCC ATG AAA GAG TGC ACA GTC CAG (78406-78429) (SEQ ID NO 20) |
| 7. CCT CTC ATA CAG ACC CCA GAG TTG (88182-88205) (SEQ ID NO 21) |
| 8. TGT TCG GAA CTG TCC ATG TTC ACG (98393-98416) (SEQ ID NO 22) |
| 9. TGA TGC TGG GAA GAC TGG AGT TAG (108003-108026) (SEQ ID NO 23) |
| 10. TAC GAC GTG TGT TCT GTG ACT CAC (118642-118665) (SEQ ID NO 24) |
| 11. GAA GTC CTA AGT CAT AGG GCC TGC (128343-128366) (SEQ ID NO 25) |
| **Exon 8 reverse primer** |
| 5'-CTT CCT CCA TCT CAT AGC TGT CGG-3' (145958-146008) (SEQ ID NO 2) |

Circulating DNA Extraction and PCR Amplification Through the EGFRvIII Deletion

Circulating DNA was extracted from plasma (including exosomes) using NucleoSpin Plasma XS kit from Macherey-Nagel GmbH&Co. Bethlehem, Pa. About 0.4 to 0.5 μg of DNA was constantly obtained from 1 mL of plasma and 24 ng of circulating DNA was sufficient to detect the deletion by PCR. For deletion detection, primers flanking the breakpoints were designed to yield a fragment of about 300 bp. Thus, the primers to be used in plasma are designed within about 150 base pairs from each side of the breakpoint. The following primers were used to amplify through the breakpoint for patient 1: forward: 5'-CAT GAT GTT TAA TTA TTA GAG GAC TC-3' (SEQ ID NO 29) and reverse: 5'-AAG CAA GGC AAA CAC ATC-3' (SEQ ID NO 30) and for patient 7: forward: 5'-TCT AGG CCG CAA TGT GGA CAA TAC-3' (SEQ ID NO 31) and reverse: 5'-ACA GTG GCT CAT GCC TGT AAT CTC-3' (SEQ ID NO 32). These primers were used to detect the deletion in the genomic DNA extracted from both the tumor and the plasma.

Whole Genome Sequencing

Randomly fragmented gDNA (~500 bp) was size-selected for the construction of the paired end tagged (PET) libraries (Quail, M. A., Swerdlow, H. & Turner, D. J. Improved protocols for the illumina genome analyzer sequencing system. *Curr Protoc Hum Genet* 2009; Chapter 18, Unit 18 12). The libraries were paired-end sequenced using an Illumina HiSeq platform with a readout length of 100 bp (Axeq Technologies, Macrogen Inc. Rockville, Md.). About 34-37 gigabases (Gb) of sequence were mapped to the human reference sequence (RefSeq), with an average mapping coverage of 22-25 fold. The raw sequence data were aligned to a human RefSeq (hg19) using the Bowtie 2 Aligner (Langmead, B., Trapnell, C., Pop, M., & Salzberg, S. L. Ultrafast and memory-efficient alignment of short DNA sequences to the human genome. Genome biology 2009; 10: R25). Four different types of tumor-specific genomic structural variations (SVs), i.e. deletion (DEL), inversion (INV), intra- and interchromosomal translocation (ITX and CTX), were detected using Control-FREEC software (Boeva, V., Popova, T., Bleakley, K., et al. Control-FREEC: a tool for assessing copy number and allelic content using next-generation sequencing data. *Bioinformatics* (Oxford, England), 2012; 28:423-5) and confirmed using the integrative genomics viewer (IGV) (Robinson, J. T. et al. Integrative genomics viewer. *Nat Biotechnol* 2011; 29, 24-26). Further Sanger sequencing was used to validate two of these SVs for each tumor. The data analysis pipeline used in this study is represented in FIG. 1.

Example 2

Detection of GBM Patients Carrying the EGFRvIII Deletion

Figures 2A, 2B:
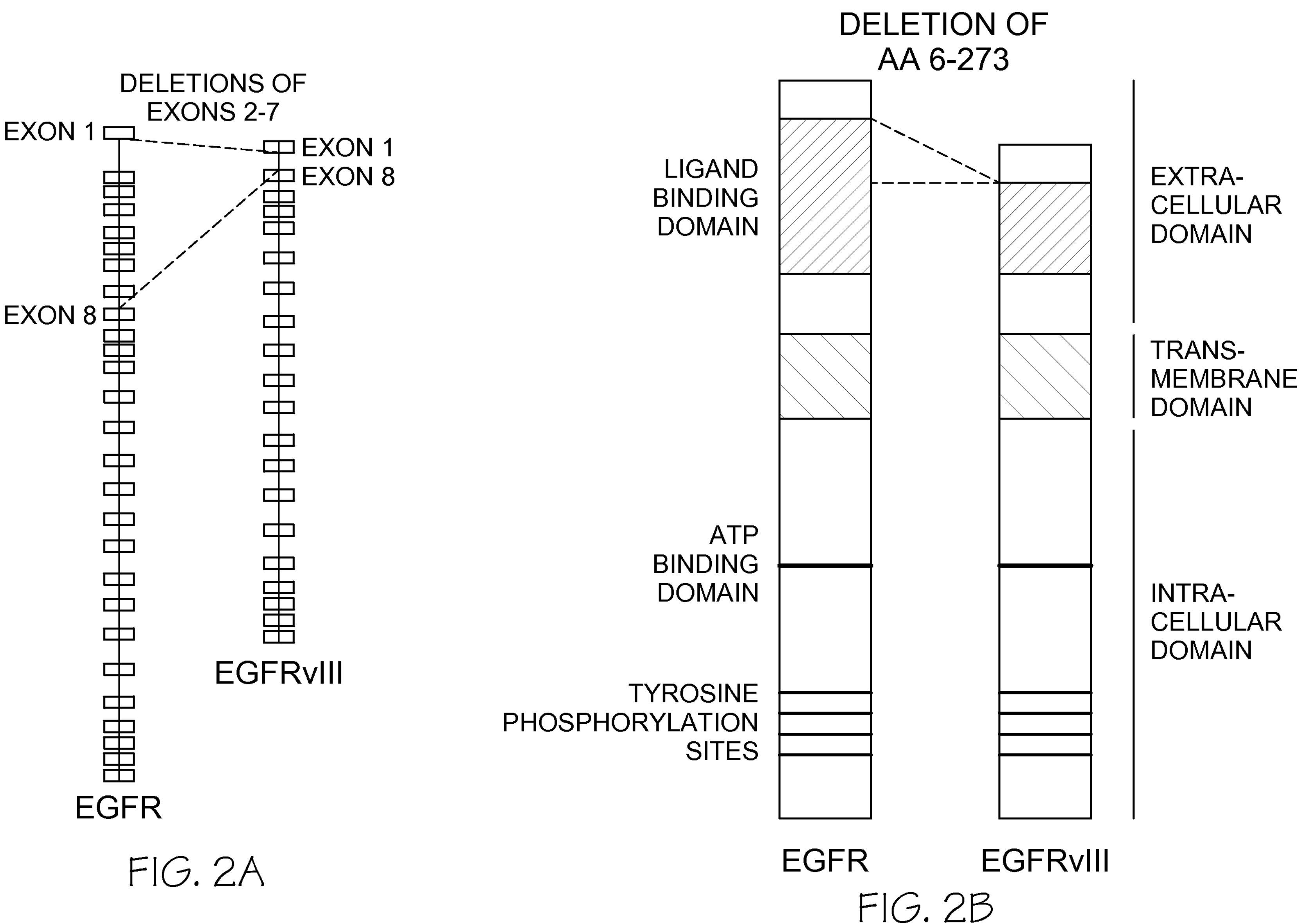
FIGS. 2A-2D. A schematic representation and detection of EGFRvIII deletion.
Figures 2C, 2D:
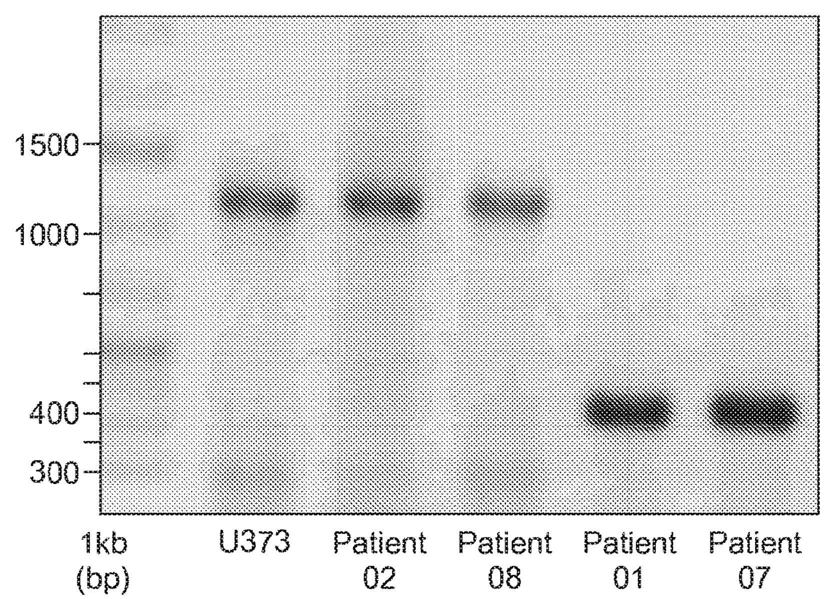

The EGFRvIII variant is the result of a deletion of exons 2 to 7 and results in a fusion of exon 1 and exon 8 (FIG. 2A). This deletion leads to the loss of 267 amino acids from the extracellular domain of the EGFR (FIG. 2B) and renders the mutant protein unable to bind to its ligand. To detect GBM patients that carry the EGFRvIII deletion, RNA was isolated from the tumors of 11 patients and was subject to a reverse transcription PCR (RT-PCR) to generate cDNA. Using a sense primer in exon 1 and an antisense primer in exon 9, PCR amplification shows that two patients (18%) carry the EGFRvIII deletion. The wild type (WT) EGFR resulted in a band of approximately 1150 bp; while the mutant variant resulted in a band of about 320 bp due to the presumed fusion of exon 1 and exon 8 (FIG. 2D). Sanger sequencing confirmed the fusion of exon 2 and exon 8 in patients 1 and 7, while the other patients are wild type, similar to the EGFR gene in the U373 GBM cell line control (FIG. 2C). Although EGFRvIII tumors are usually heterogeneous and contain EGFR wild type as well (as in tissue from patient 282 control), we only obtained the PCR band corresponding to the mutant EGFRvIII in the tumors (FIG. 2D).

Example 3

Detection of EGFRvIII Deletions in the Genomic DNA and Determination of the Breakpoints The use of genomic DNA to detect the EGFRvIII deletion is complex due to the presence of 11 Alu sites (27) in intron I (123 Kb) and one Alu site in intron 7 of EGFR gene (Reiter, J. L. et al (2001); "Comparative Genomic Sequence Analysis and Isolation of Human and Mouse Alternative EGFR Transcripts Encoding Truncated Receptor Isoforms". Genomics; 2001; 71: 1-20). These Alu sites are involved in DNA recombination events that generate genomic deletions of varying sizes leading to different EGFRvIII deletions in GBM patients. While these deletions are different at the genomic level, the mRNA is spliced the same way leading to the same truncated protein in all patients. We therefore developed a long range PCR-based strategy that uses forward primers that span the whole intron 1 and a reverse primer in exon 8 (FIG. 3A). These primers that are designed to be five kilo bases apart from each other allowed for amplification of several PCR products in the patient's genomic DNA but not in the constitutional DNA from white blood cells (WBC), indicating potential EGFRvIII deletions (FIGS. 3B and 3C). These PCR products were Sanger sequenced and their EGFRvIII status confirmed. We obtained two confirmed populations of EGFRvIII deletions for patients 1 (FIG. 3B) and 7 (FIG. 3C), and one population in patient 9 (data not shown). Surprisingly, in patient 7, one of the deletions didn't involve a direct recombination between intron 1 and intron 7 in EGFR but it involved adjacent sequences to the EGFR gene, namely the area containing SEPT14 and SEC61G genes (FIG. 3D). Patients 1 and 9, however, showed an intragenic recombination between intron 1 and intron 7 (data not shown). These recombinations and the resulting EGFRvIII deletions were confirmed using next generation sequencing of patient 7's normal and tumor DNA.

Example 4

Figure 3:
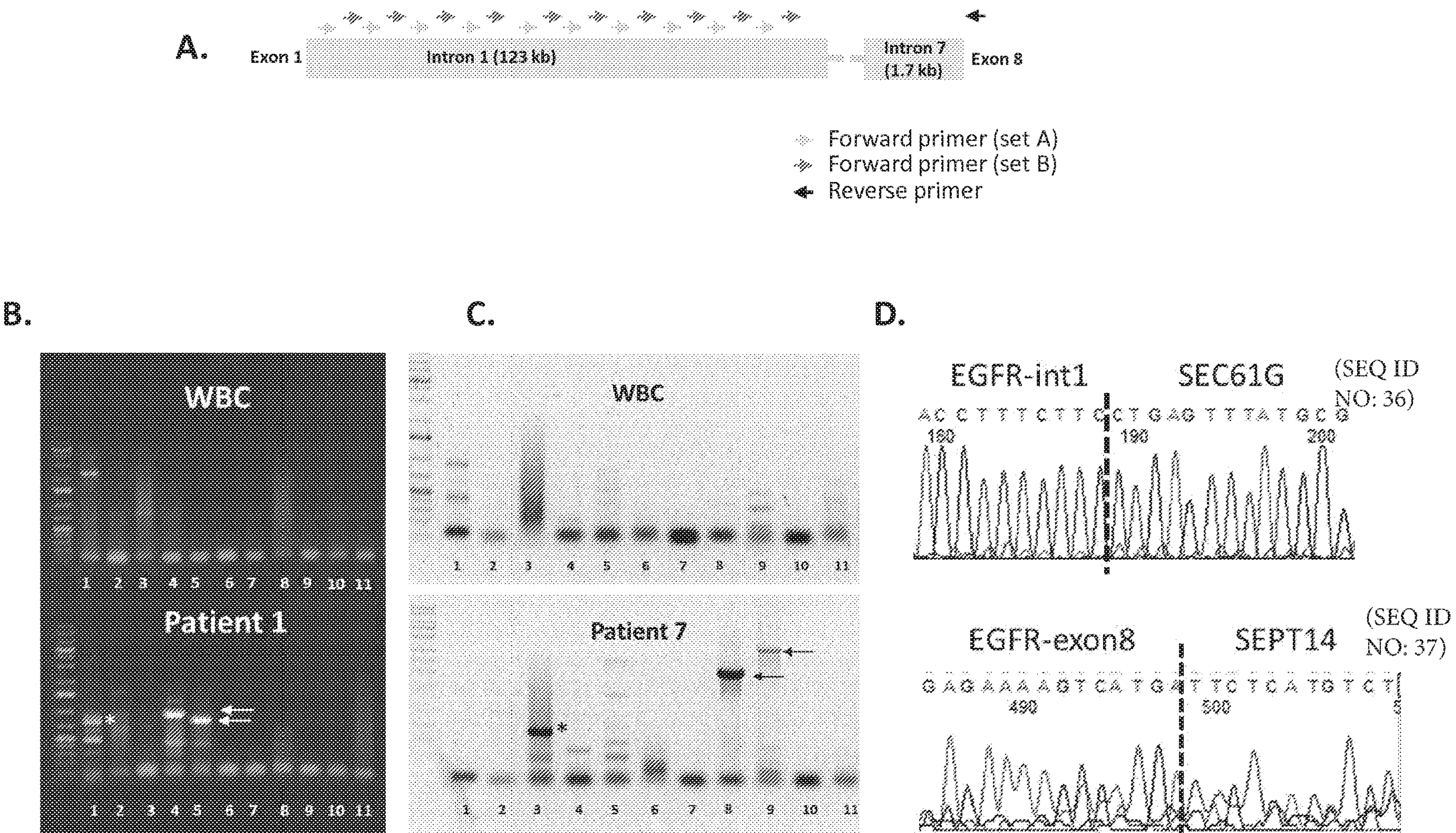
FIGS. 3A-3D. Detection of EGFRvIII genomic deletions and determination of the breakpoints.
Figure 4A:
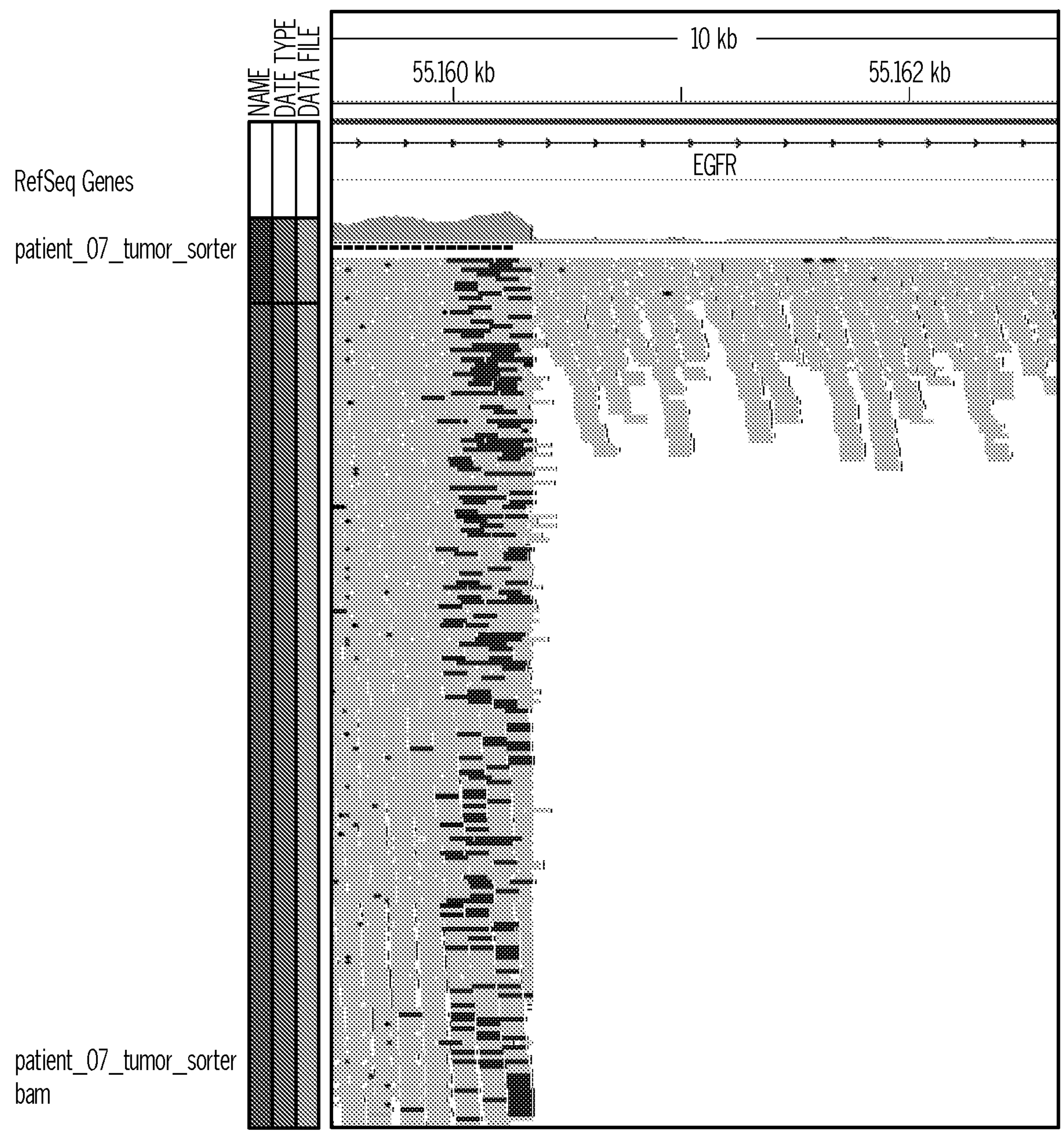
FIGS. 4A-4E. Confirmation of the EGFRvIII deletion using next generation sequencing.
Figure 4B:
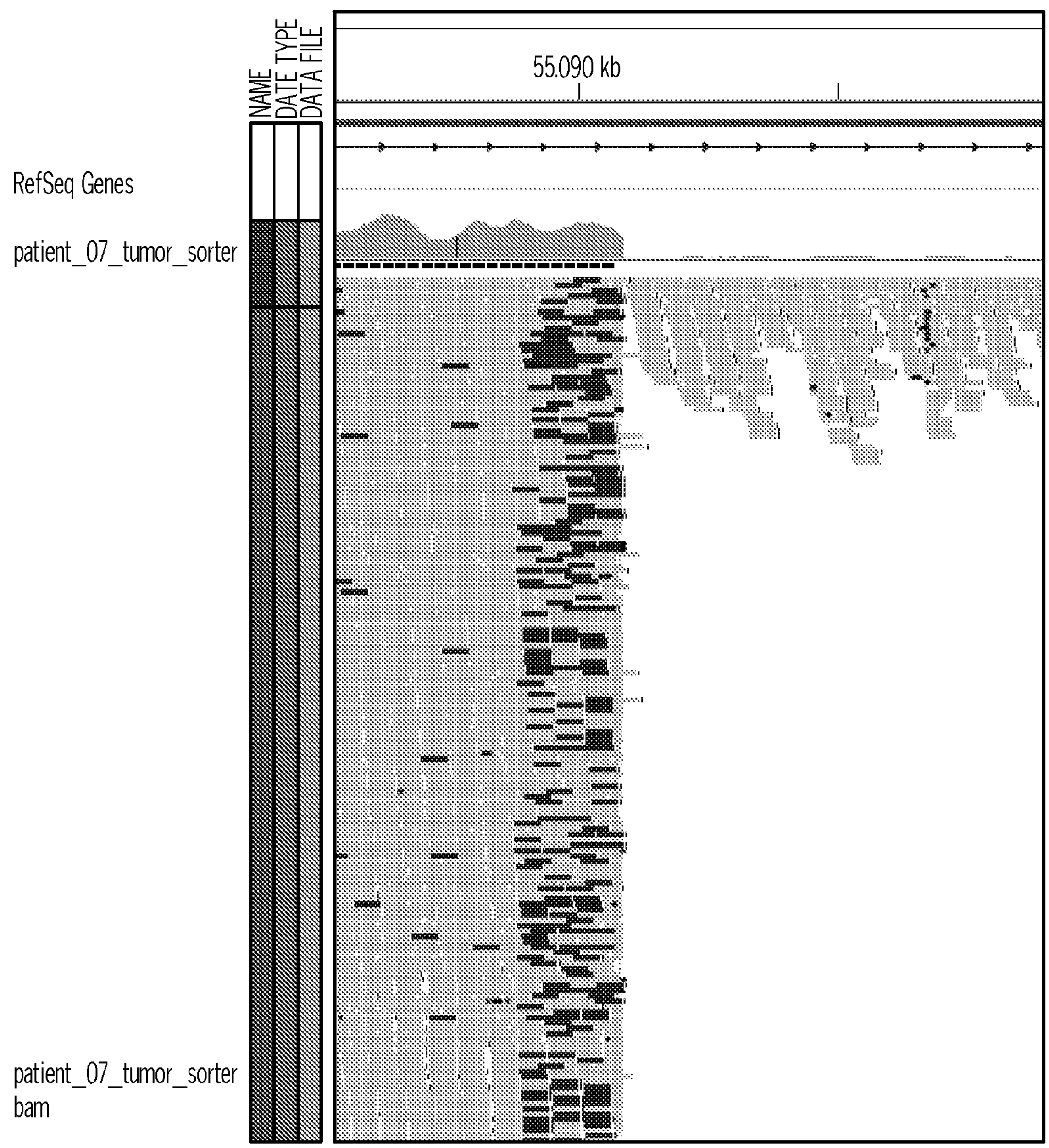
Figure 4C:
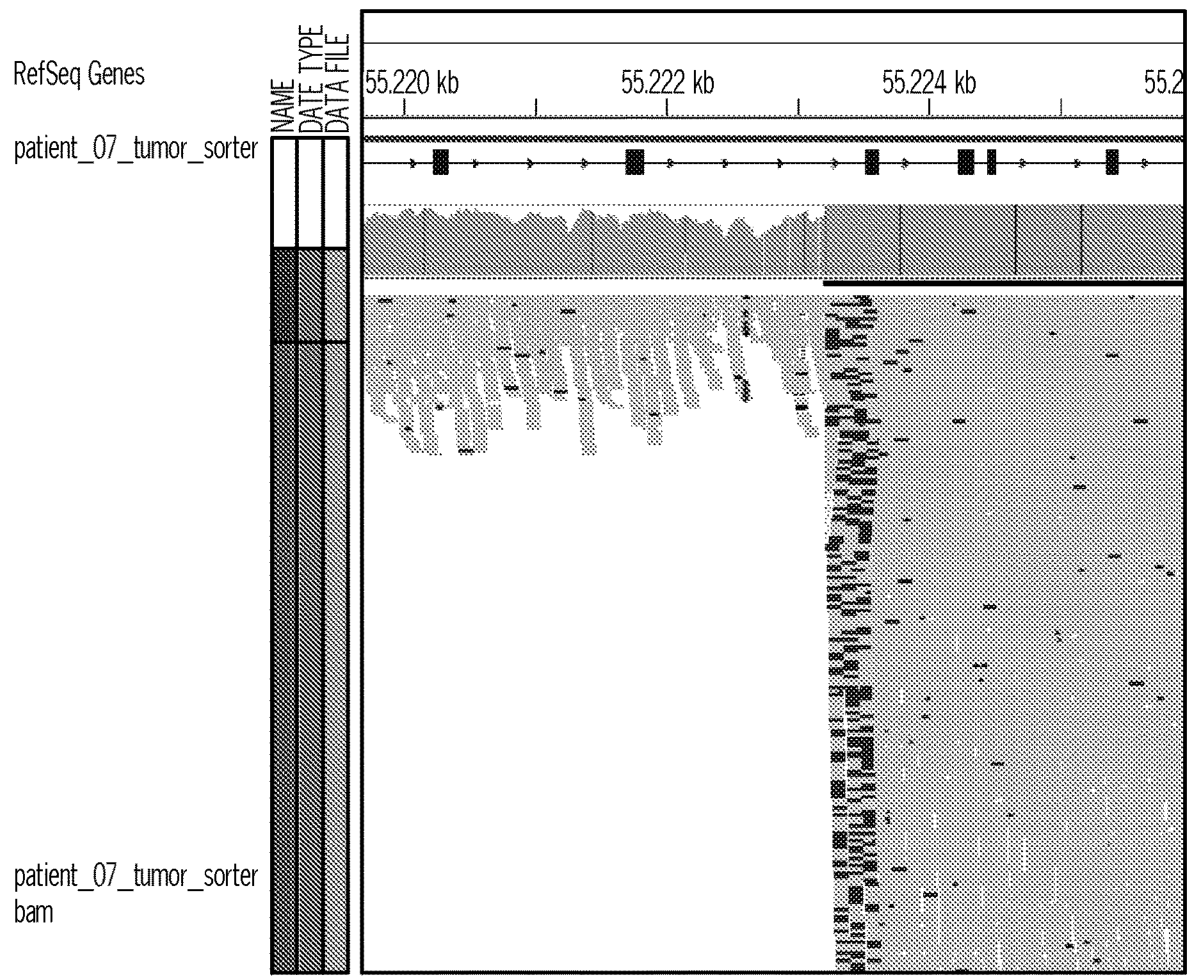
Figure 4D:
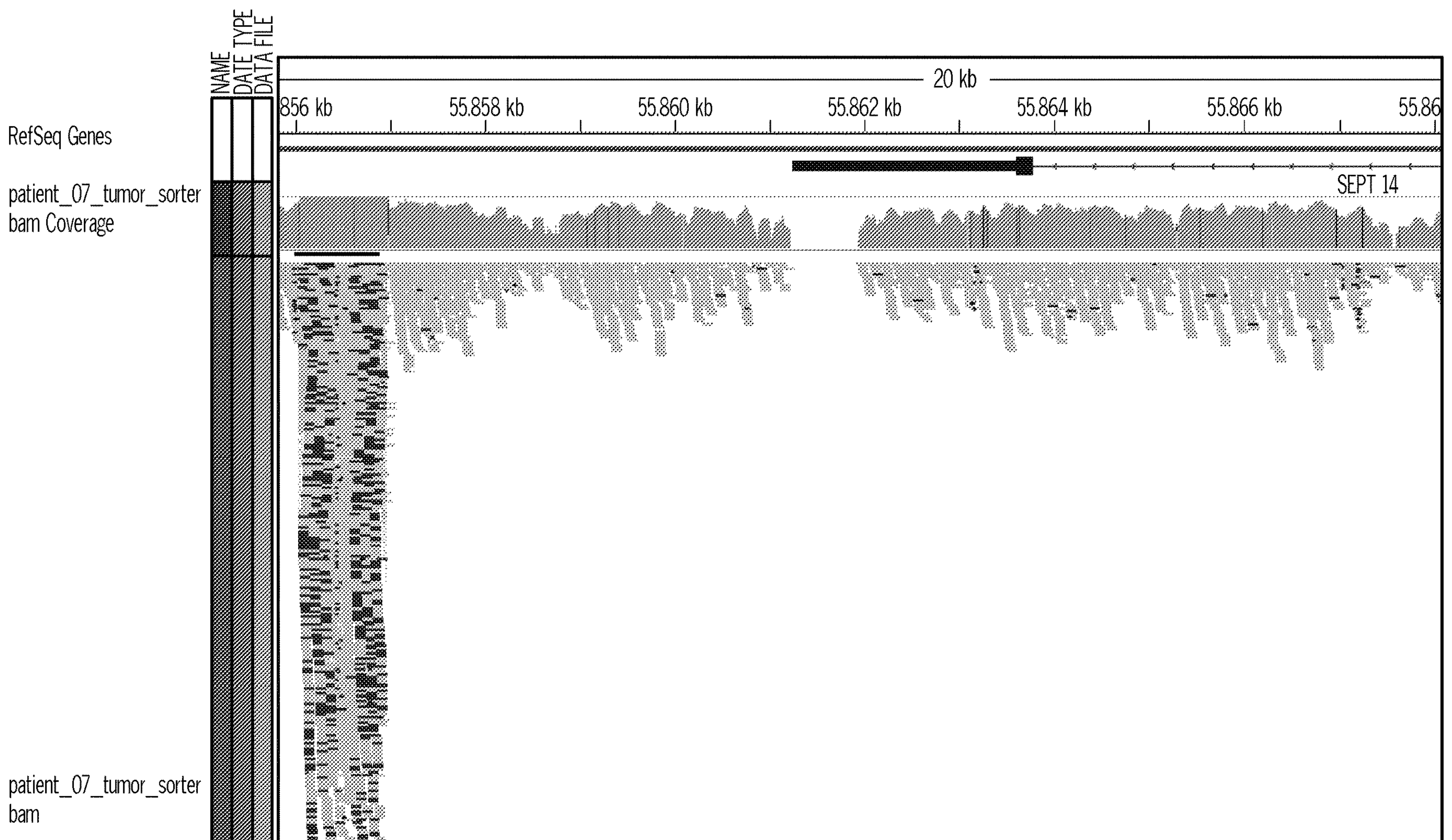
Figure 4E:
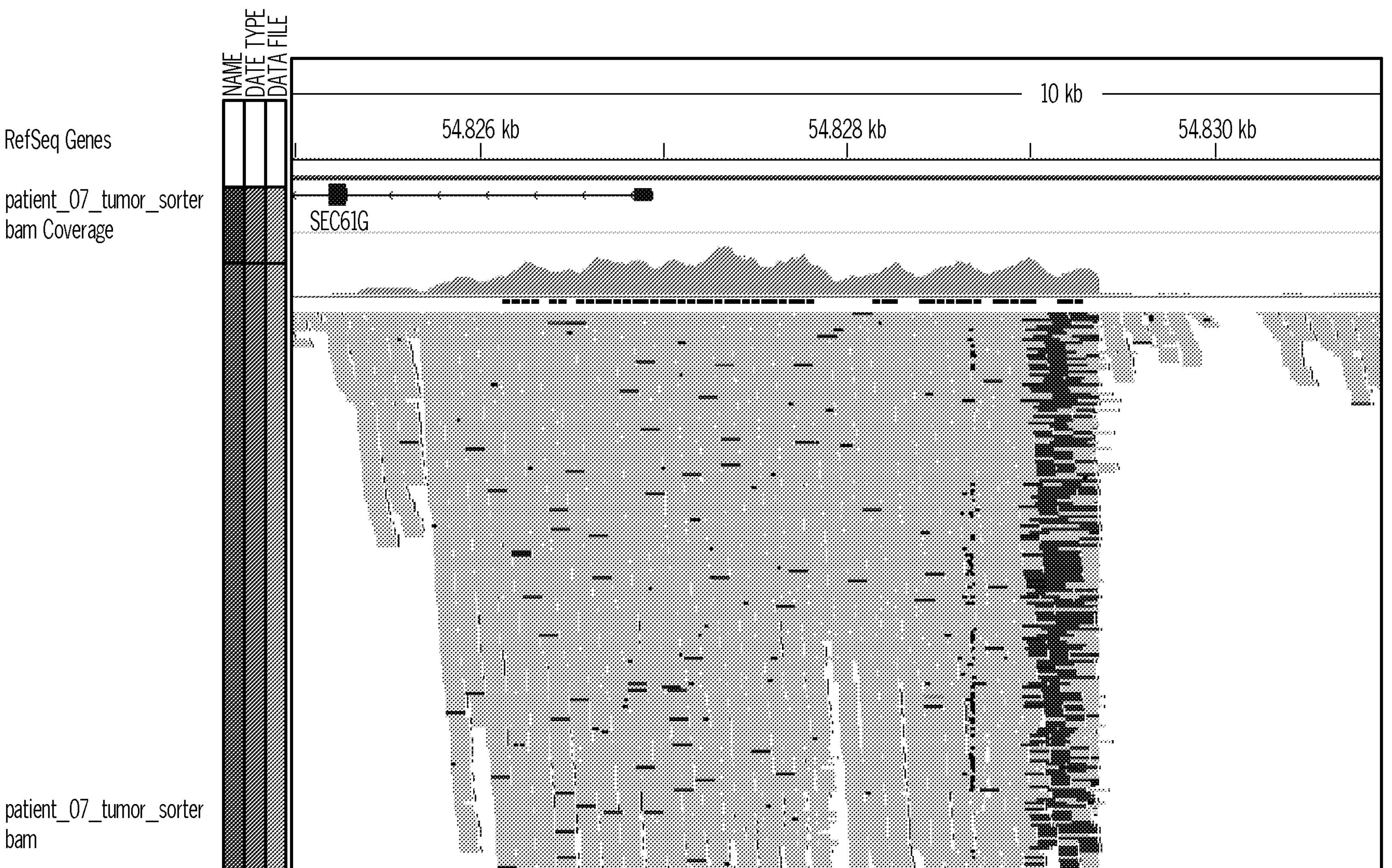

Confirmation of the EGFRvIII Deletions Using Next Generation Pair-End Sequencing To confirm the identity of EGFRvIII deletions detected by our long range PCR amplification technique, and to check whether other deletions were missed using our strategy, genomic DNA from patient 7 and the corresponding normal DNA from WBC were subjected to whole genome sequencing using the Illumina GAII platform. Four different types of tumor-specific genomic structural variations (SVs), i.e. deletion (DEL), inversion (INV), intra- and interchromosomal translocation (ITX and CTX), were detected using Control-FREEC software (Boeva, V., Popova, T., Bleakley, K., et al. Control-FREEC: a tool for assessing copy number and allelic content using next-generation sequencing data. *Bioinformatics* (Oxford, England), 2012; 28:423-5) and confirmed using the integrative genomics viewer (IGV) (Robinson, J. T. et al. Integrative genomics viewer. *Nat Biotechnol* 2011; 29, 24-26). As was seen with the long range PCR amplification, two separate deletions in intron I were detected and confirmed using IGV (FIG. 3). FIGS. 4A and 4B show the start of the deletions in intron 1, while FIG. 4C shows the end of the deletions in intron 7. Not only were we able to detect the start and end of each deletion, but we were also able to confirm the involvement of the region around SEPT14 gene and SEC61G in the recombination as indicated by the rearrangement of these two domains in this patient (FIGS. 4D and 4E). These findings confirm that our long range PCR strategy is efficient in detecting EGFRvIII deletions with very high confidence and can be used to detect the deletion in the genomic DNA without the need to sequence the whole genome, which can be costly and time consuming.

Example 5

Tracking of the EGFRvIII Deletion in the Peripheral Blood

Figure 5A:
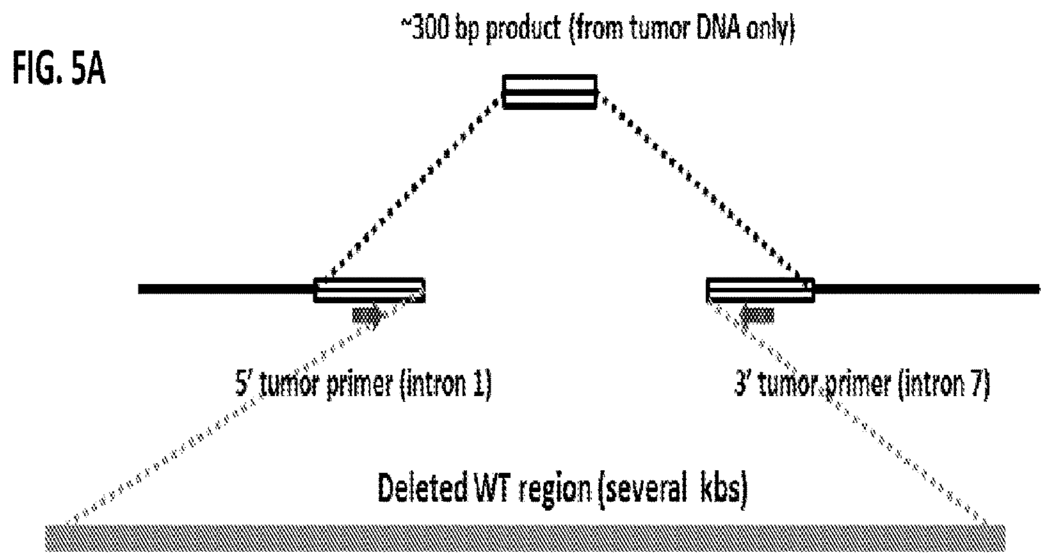
FIGS. 5A-5D. Detection and tracking of the EGFRvIII deletion in the plasma.
Figure 5B:
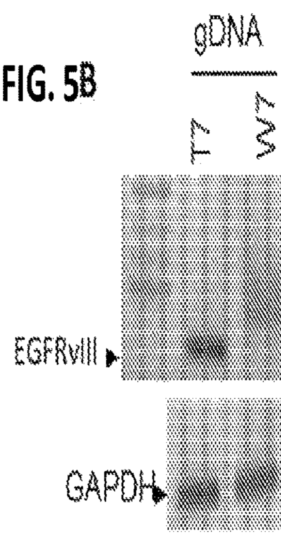
Figure 5C:
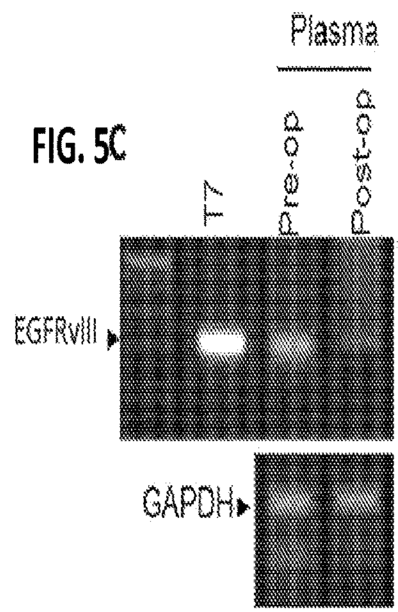
Figure 5D:
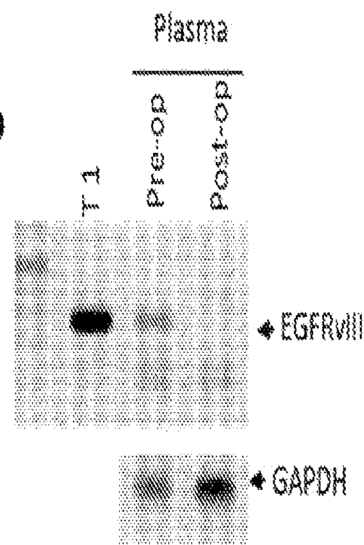

To track the EGFRvIII deletion in the peripheral blood of the patients that carry this mutation and evaluate whether the mutation can be used to monitor the status of the tumor, blood was collected from the patients shortly before surgery and at three weeks after surgery. Primers were designed around the deletions to generate a PCR fragment of about 300 bp when the deletion is present. In the wild type EGFR, the fragment is too large to be detected by conventional and therefore, no PCR product is expected (FIG. 5A). As predicted, PCR amplification from genomic tumor DNA (gDNA) produced the expected size band while the wild type DNA from WBCs didn't (FIG. 5B). GAPDH was used as control. To check whether the amount of detected mutant DNA in the plasma can reflect the status of the tumor, we amplified the mutant DNA from the plasma of patient 7 (FIG. 5C) and patient 1 (FIG. 5D). Patient 7 had an incomplete resection of the tumor while patient 1 had a complete resection. Very consistent with the tumor status in these two patients, patient 1 plasma had no circulating tumor DNA (FIG. 5D), while patient 7 showed a residual amount of tumor DNA reflecting the incomplete resection of the tumor in this patient (FIG. 5C). These data show that this strategy is promising in detecting EGFRvIII in genomic DNA and in tracking these deletions in the peripheral blood.

All documents cited are incorporated herein by reference; the citation of any document is not to be construed as an admission that it is prior art with respect to the present invention.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed:

1. A kit comprising:

a first primer set comprising forward primers corresponding to a DNA sequence in intron 1 of an EGFR gene and a reverse primer that corresponds to a DNA sequence in exon 8 of an EGFR gene;

a second primer set comprising forward primers corresponding to the DNA sequence in intron 1 of the EGFR gene that are separated by about 5 kb from the forward primers of the first primer set and the reverse primer that corresponds to a DNA sequence in exon 8 of the EGFR gene, wherein the forward primers of the first and second sets are comprised within the base pairs defining intron 1 of the EGFR gene;

one or more amplification primers that hybridize to priming sites that flank breakpoints in EGFRvIII, wherein the one or more amplification primers are designed to yield a PCR fragment of about 300 base pairs and wherein the one or more amplification primers comprise SEQ ID NO: 29, SEQ ID NO: 30, SEQ ID NO: 31, or SEQ ID NO: 32; and a dual-labeled hydrolysis probe specific to a region of EGFR sequence amplified by the plurality of forward primers and the reverse primer.

2. The kit of claim of claim 1, wherein the forward primers of the first primer set and the second primer set are selected from primers set forth in Table 1.

3. The kit of claim 1, wherein the reverse primer that corresponds to a DNA sequence in exon 8 of EGFR has the nucleotide sequence (SEQ ID NO: 2)
(5'-CTTCCTCCATCTCATAGCTGTCGG-3').

4. The kit of claim 1, wherein the kit further comprises a forward primer for exon 1 of EGFR.

5. The kit of claim 4, wherein the forward primer for exon 1 has the nucleotide sequence (SEQ ID NO: 1)
(5'-GTCCGCTCTCGAGGAAAGAAA-3').

6. The kit of claim 1, wherein the dual-labeled hydrolysis probe comprises a fluorescent label and a quencher.

7. A kit comprising:

one or more amplification primers that hybridize to priming sites that flank breakpoints in EGFRvIII, wherein the one or more amplification primers are designed to yield a PCR fragment of about 300 base pairs and wherein the one or more amplification primers comprise SEQ ID NO: 29, SEQ ID NO: 30, SEQ ID NO: 31, or SEQ ID NO: 32; and a dual-labeled hydrolysis probe specific to a region of EGFR sequence amplified by the one or more amplification primers.

8. The kit of claim 7, wherein the dual-labeled hydrolysis probe comprises a fluorescent label and a quencher.

9. The kit of claim 7, further comprising a nucleotide comprising SEQ ID NO: 35.

10. The kit of claim 7, further comprising a nucleotide comprising SEQ ID NO: 33 or 34.

11. The kit of claim 7, wherein the one or more amplification primers comprise SEQ ID NO: 29 and SEQ ID NO: 30.

12. The kit of claim 7, wherein the one or more amplification primers comprise SEQ ID NO: 31 and SEQ ID NO: 32.

* * * * *